(12) United States Patent
Limbach et al.

(10) Patent No.: US 11,635,443 B2
(45) Date of Patent: *Apr. 25, 2023

(54) AUTOMATIC ANALYZER AND METHOD FOR CARRYING OUT CHEMICAL, BIOCHEMICAL, AND/OR IMMUNOCHEMICAL ANALYSES

(71) Applicant: MEON MEDICAL SOLUTIONS GMBH & CO KG, Graz (AT)

(72) Inventors: Berthold Limbach, Lotzwil (CH); Arnold Bartel, Graz (AT); Herfried Huemer, Feldbach (AT); Reinhard Marik, Graz (AT); Patrick Kraus-Füreder, Graz (AT); Robert Scholz-Mareich, Graz (AT); Wolfgang Sprengers, Vasoldsberg (AT)

(73) Assignee: MEON MEDICAL SOLUTIONS GMBH & CO KG, Graz (AT)

( * ) Notice: Subject to any disclaimer, the term of this patent is extended or adjusted under 35 U.S.C. 154(b) by 243 days.

This patent is subject to a terminal disclaimer.

(21) Appl. No.: 16/996,703

(22) Filed: Aug. 18, 2020

(65) Prior Publication Data

US 2021/0041472 A1 Feb. 11, 2021

Related U.S. Application Data

(62) Division of application No. 16/629,539, filed as application No. PCT/AT2018/060147 on Jul. 13, 2018.

(30) Foreign Application Priority Data

Jul. 14, 2017 (AT) .................................. 50593/2017
Jul. 14, 2017 (AT) .................................. 50595/2017

(Continued)

(51) Int. Cl.
*G01N 35/10* (2006.01)
*G01N 21/59* (2006.01)
(Continued)

(52) U.S. Cl.
CPC .......... *G01N 35/1004* (2013.01); *B01L 3/021* (2013.01); *B01L 3/0286* (2013.01);
(Continued)

(58) Field of Classification Search
None
See application file for complete search history.

(56) References Cited

U.S. PATENT DOCUMENTS 4,234,539 A    11/1980   Ginsberg et al.
4,299,796 A * 11/1981   Hogen Esch .......... G01N 35/00
                                                                             422/65
(Continued)

FOREIGN PATENT DOCUMENTS

AT          510631 B1    1/2013
DE       2726498 A1   12/1978
(Continued)

*Primary Examiner* — P. Kathryn Wright
(74) *Attorney, Agent, or Firm* — Dykema Gossett PLLC

(57) ABSTRACT

Aspects of the present disclosure relate to a method and/or a device for carrying out chemical, biochemical and/or immunochemical analyses of liquid samples, which are present in a sample store of an automatic analyzer, with the aid of liquid reagents which are present in at least one reagent store of the analyzer. In one example embodiment, the automatic analyzer includes cuvettes, a first pipettor, a device with an optical measurement unit, a device for heterogenous immunoassays, a cuvette washing unit, a needle washing unit, a temperature control unit.

18 Claims, 28 Drawing Sheets

(30) Foreign Application Priority Data

Apr. 23, 2018 (AT) .................................. 50340/2018
Apr. 23, 2018 (AT) .................................. 50341/2018

(51) Int. Cl.
*G01N 21/31* (2006.01)
*G01N 21/03* (2006.01)
*G01N 33/543* (2006.01)
*B01L 3/00* (2006.01)
*B01L 3/02* (2006.01)
*B01L 7/00* (2006.01)
*G01N 35/00* (2006.01)

(52) U.S. Cl.
CPC ....... *B01L 3/50851* (2013.01); *B01L 3/50857* (2013.01); *B01L 7/00* (2013.01); *B01L 13/02* (2019.08); *G01N 21/0332* (2013.01); *G01N 21/31* (2013.01); *G01N 21/59* (2013.01); *G01N 33/54386* (2013.01); *B01L 2300/0636* (2013.01); *B01L 2300/0663* (2013.01); *B01L 2300/1805* (2013.01); *B01L 2400/0439* (2013.01); *G01N 2035/00346* (2013.01); *G01N 2035/00554* (2013.01); *G01N 2035/1076* (2013.01)

(56) References Cited

U.S. PATENT DOCUMENTS

| | | | |
|---|---|---|---|
| 4,495,149 A * | 1/1985 | Iwata | G01N 35/00 204/461 |
| 4,931,402 A | 6/1990 | Abplanalp | |
| 5,178,833 A | 1/1993 | Covain | |
| 5,592,959 A * | 1/1997 | Nagai | B08B 9/023 73/864.22 |
| 5,897,837 A | 4/1999 | Mizuno | |
| 6,333,008 B1 | 12/2001 | Leistner et al. | |
| 7,998,432 B2 | 8/2011 | Rousseau | |
| 8,064,062 B2 | 11/2011 | Ogawa | |
| 8,675,187 B2 | 3/2014 | Harada et al. | |
| 8,911,685 B2 | 12/2014 | Watanabe et al. | |
| 2006/0110287 A1 | 5/2006 | Kraemer et al. | |
| 2010/0047128 A1* | 2/2010 | Mototsu | B08B 3/102 422/63 |
| 2011/0076199 A1 | 3/2011 | Meller et al. | |
| 2011/0223066 A1 | 9/2011 | Yamazaki et al. | |
| 2013/0301051 A1 | 11/2013 | Pogosyan et al. | |
| 2014/0134620 A1* | 5/2014 | Tajima | G01N 21/6452 435/6.12 |
| 2014/0287523 A1 | 9/2014 | Donohue | |

FOREIGN PATENT DOCUMENTS

| | | |
|---|---|---|
| EP | 0601213 A1 | 6/1994 |
| EP | 0644426 A1 | 3/1995 |
| EP | 1615037 A1 | 1/2006 |
| EP | 1230553 B1 | 8/2008 |
| EP | 1995597 A1 | 11/2008 |
| EP | 2322939 A1 | 5/2011 |
| EP | 2410342 A2 | 1/2012 |
| GB | 1321754 A | 6/1993 |
| JP | 2007010345 B1 | 1/2007 |
| JP | 2007303964 A | 11/2007 |
| WO | 9946601 A1 | 9/1999 |
| WO | 2010122203 A1 | 10/2010 |

* cited by examiner

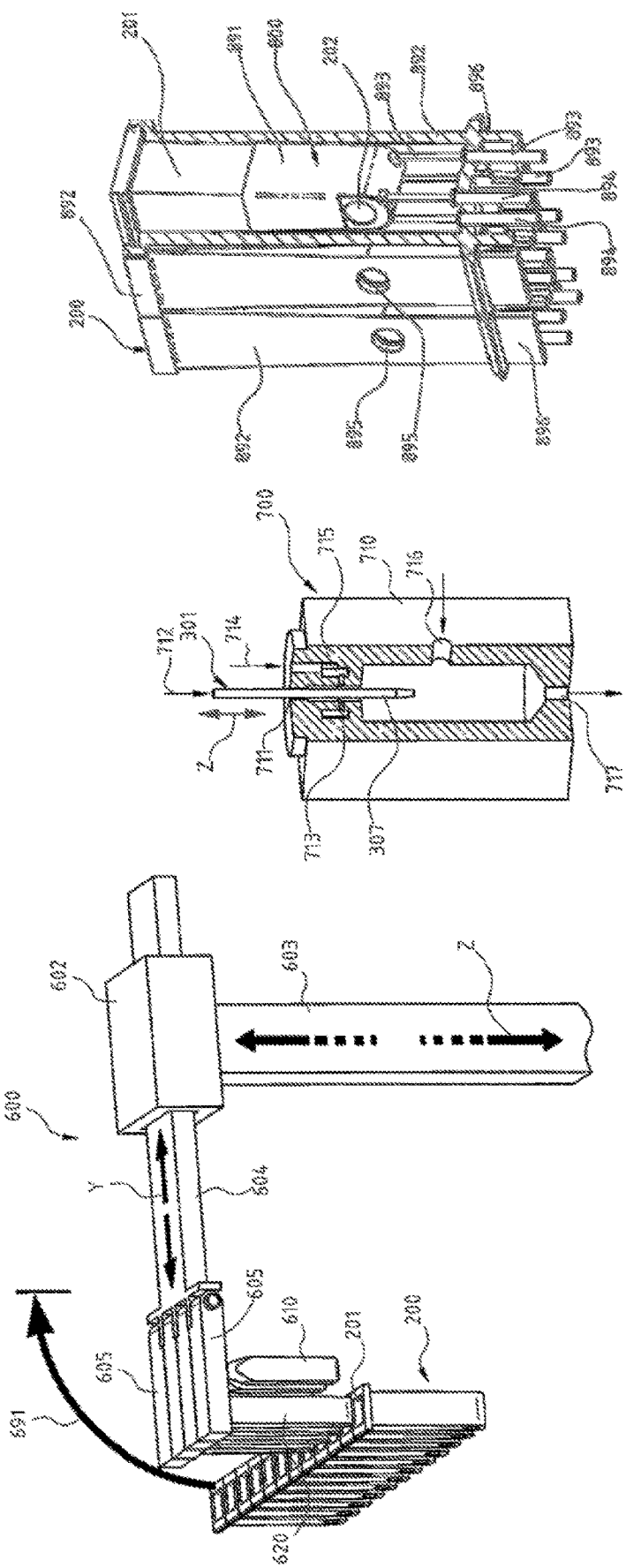

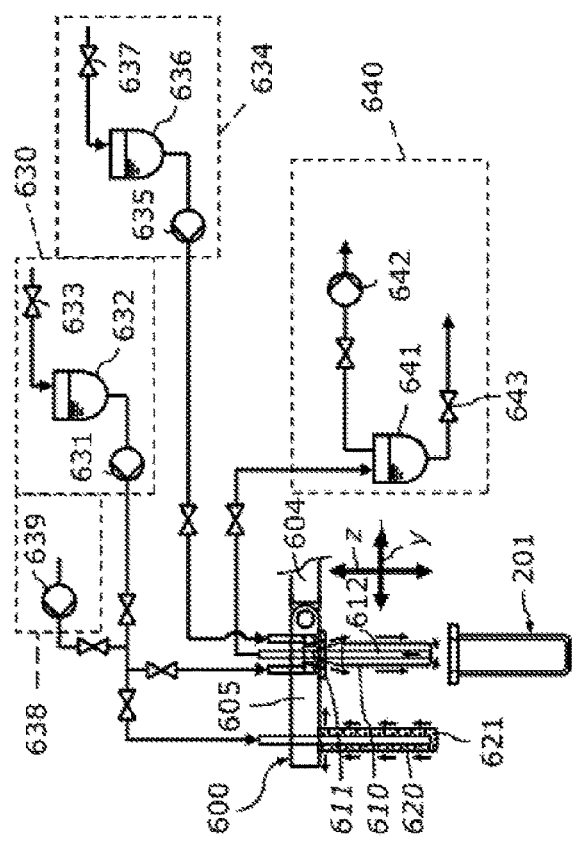
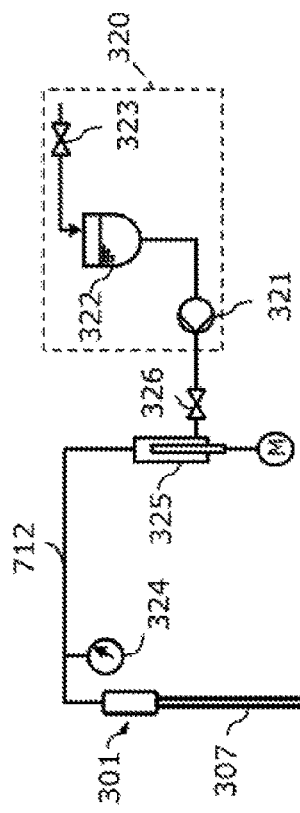
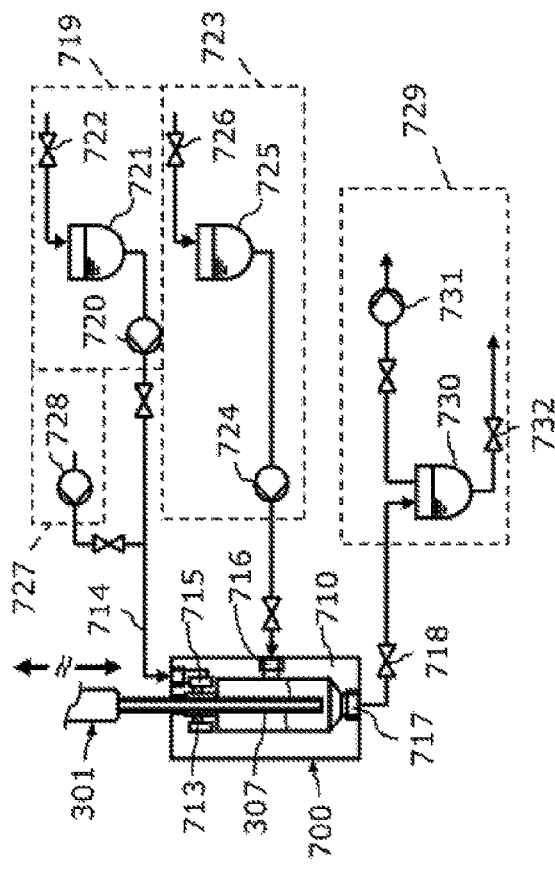
Fig. 9a
Fig. 9b
Fig. 9c

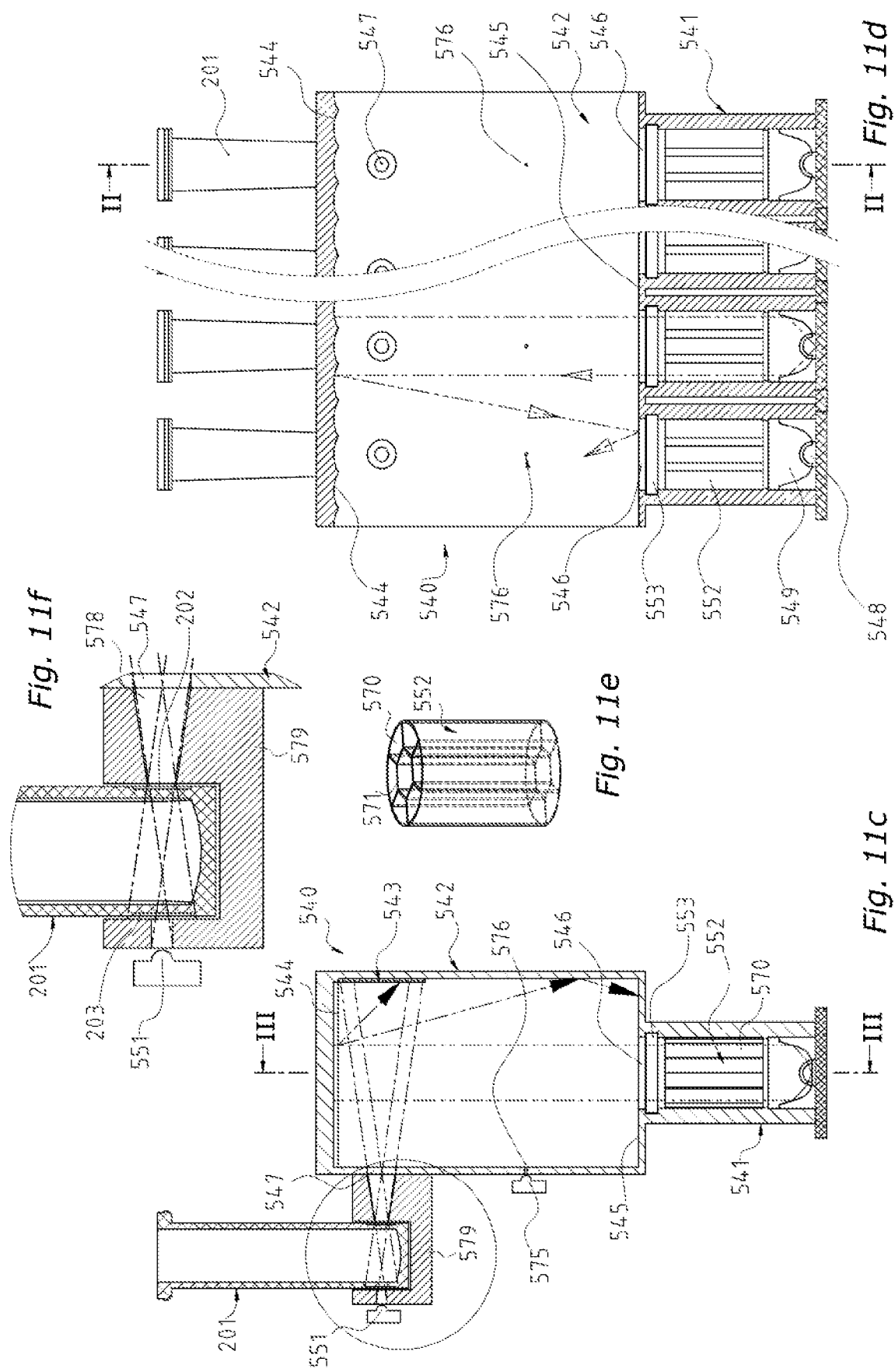

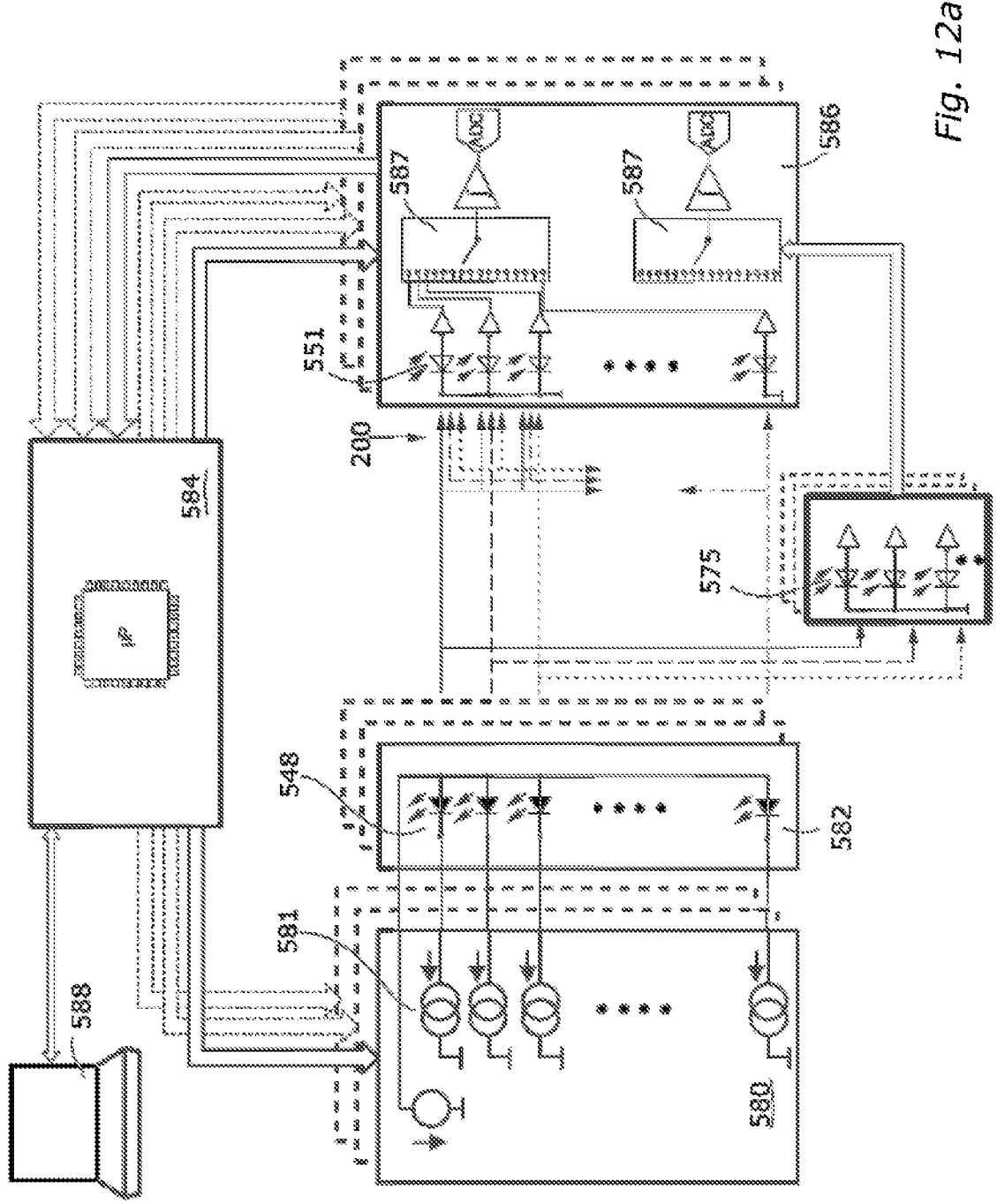

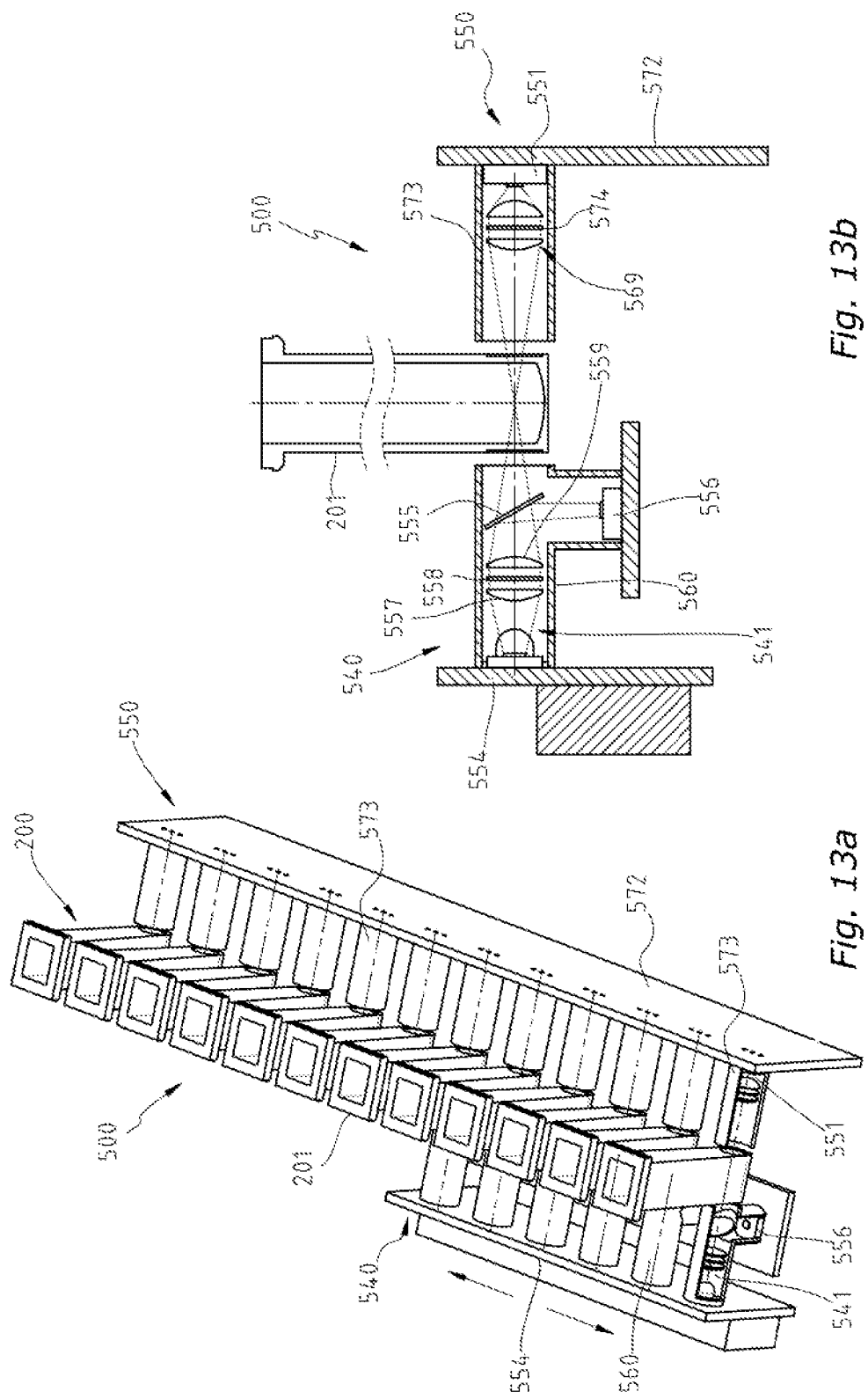

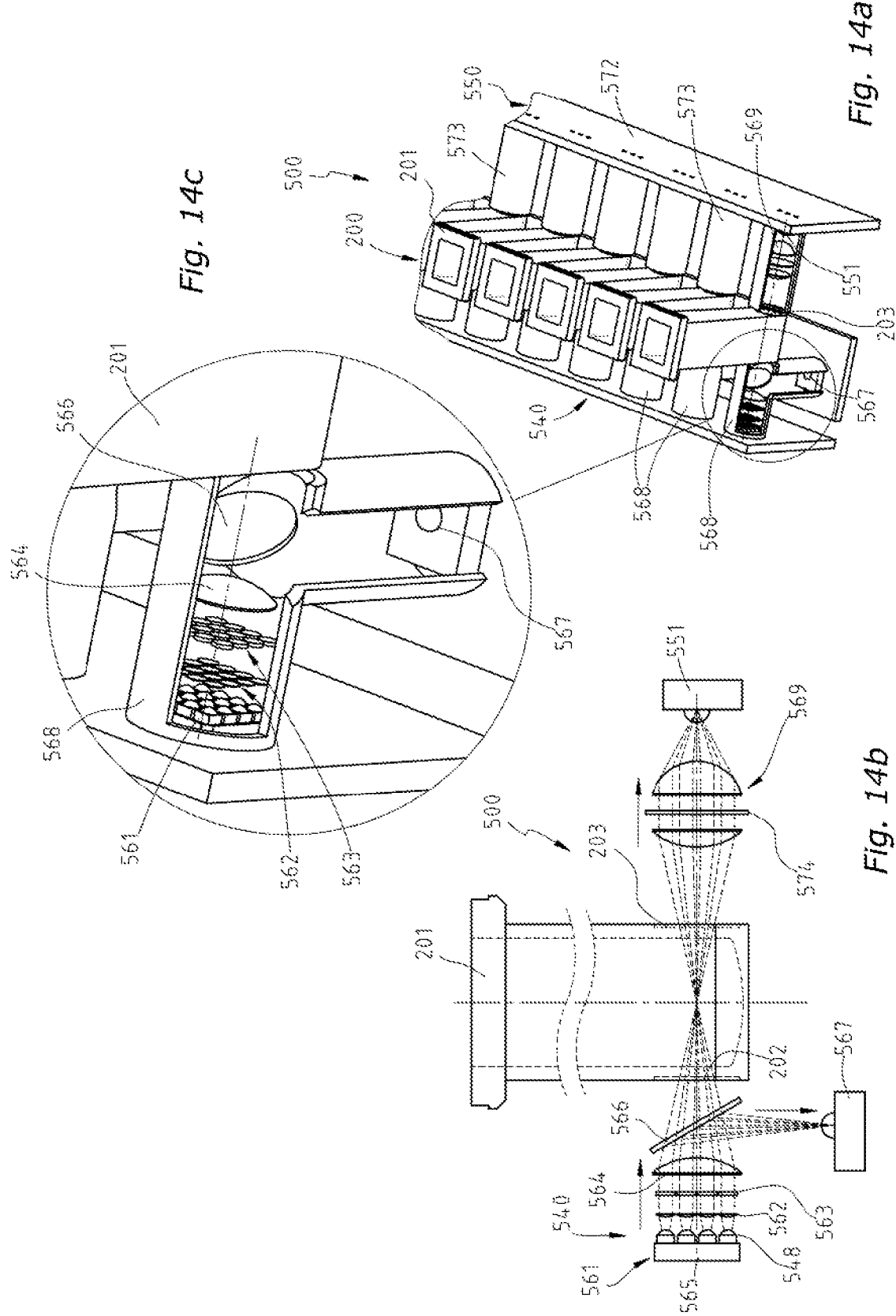

AUTOMATIC ANALYZER AND METHOD FOR CARRYING OUT CHEMICAL, BIOCHEMICAL, AND/OR IMMUNOCHEMICAL ANALYSES

CROSS-REFERENCE OF RELATED APPLICATIONS

This application is a divisional of U.S. application Ser. No. 16/629,539, filed 8 Jan. 2020, which is a national stage filing based upon International PCT Application No. PCT/AT2018/060147, filed 13 Jul. 2018, which claims the benefit of priority to Austria application No. A 50593/2017, filed 14 Jul. 2017, Austria application No. A 50595/2017, filed 14 Jul. 2017, Austria application No. 50340/2018, filed 23 Apr. 2018, and Austria application No. A 50341/2018, filed 23 Apr. 2018.

BACKGROUND

The invention relates to an automatic analyzer for carrying out chemical, biochemical and/or immunochemical analyses of liquid samples, which are present in a sample store of the analyzer, with the aid of liquid reagents, which are present in at least one reagent store of the analyzer, and to a method for automatic chemical, biochemical and/or immunochemical analysis of liquid samples.

Automated analyzers or analysis devices are routinely used, for example in clinical diagnostics, analytics and microbiology, where there is a need to determine various properties and ingredients of liquid samples quickly, accurately and reproducibly, in particular using optical methods.

Various measurement principles are used in the known analysis devices. On the one hand, use is made of devices having a stationary detection unit, for example a stationary photometer, and a disk-shaped, rotatable holder with cuvettes for holding the reaction mixtures to be measured, consisting of samples and reagents. The cuvettes are successively moved past the detection unit and measured. Consequently, the cuvette carousel has to stop whenever a new sample or a reagent is being introduced into a cuvette or the cuvette is to be washed and made available for a new test. The cycle times, which in this concept are rigidly predefined, are associated with a considerable loss of efficiency. Further details regarding this can be found in the discussion of the prior art (see point A).

Photometry

The physical effect on which photometric measurement is based is the absorption of light of particular wavelengths by particular substances present in a liquid. The resulting reduction in the intensity of the light passing through the cuvette is detected using measurement technology, and permits a quantitative determination of the concentration of a substance by taking the following equations into account:

$$T = I/I_0 \quad \text{(Eq 1)}$$

$$E = -\log T = \log(I_0/I) \quad \text{(Eq 2)}$$

$$E = \varepsilon \cdot c \cdot d \quad \text{(Eq 3) Lambert-Beer's law}$$

where T ... transmission
E ... extinction
$I_0$ ... intensity in the absence of the light-absorbing substance
I ... intensity in the presence of the light-absorbing substance
c [mol/l] ... molar concentration
d [cm] ... thickness of the absorbent liquid layer
$\varepsilon$ [1 mol$^{-1}$ cm$^{-1}$] ... molar extinction coefficient (substance-dependent variable)

The molar concentration c can thus be calculated directly from the result of an extinction or transmission measurement. This type of measurement is used in chemical and enzymatic reactions to determine the molar concentration of particular analytes present in the sample (blood plasma, urine, etc.). In this case, light-absorbing substances (dyes) appear or disappear, and the molar concentration of the analyte to be determined is then deduced from the extinction or changes in the extinction thereof.

In the field of clinical chemical analysis, numerous parameters are determined using photometric methods, for example the determination of enzymes (AP, GOT, GPT, γ-GT, amylase, CK), electrolytes ($Na^+$, $K^+$, $Ca^{2+}$, $Cl^-$, $Mg^{2+}$), organ-specific substances (heart, liver, kidney) and numerous metabolic variables (bilirubin, total cholesterol, HDL and LDL cholesterol, triglycerides, glucose, uric acid, creatinine, urea and lactate).

Turbidimetry and Nephelometry

This type of measurement is used in homogeneous immunoassays, wherein particular analytes, such as for example metabolites, enzymes, peptides or proteins, are reacted with antibodies. This results in larger structures, which cause increased light scattering or turbidity of the reaction mixture.

While in the case of transmission measurement the intensity of the light beam passing through decreases as the analyte concentration increases due to the increasing turbidity, at a detection angle of for example 90° the intensity of the scattered light beam increases as the turbidity increases.

The turbidity measurement in the form of the transmission measurement is referred to as turbidimetry. The associated measurement device is referred to as a turbidimeter. The scattered light measurement taking place at an angle of, for example, 90° to the light beam passing through is referred to as nephelometry, and the associated measurement device is referred to as a nephelometer.

Luminescence/Chemiluminescence

In the case of luminescence (for example fluorescence, phosphorescence, chemiluminescence), the light emitted by molecules is measured. In the case of chemiluminescence, the light emission takes place as a result of a chemical reaction.

Luminometric methods are highly sensitive and therefore are well-suited to detecting labels in immunoassays.

For a better understanding of the invention, a few essential technical terms used in the present application will be defined in greater detail:

Analyzer: Device for carrying out chemical, biochemical and/or immunochemical analyses of liquid samples, which are present in a sample store located in the analyzer, with the aid of liquid reagents, which are present in at least one reagent store located in the analyzer.

x-axis, y-axis and z-axis: The x-axis means the horizontally extending longitudinal axis, the y-axis means the horizontally extending width or depth axis, and the z-axis means the vertically extending height axis of the analyzer (see for example FIG. 3a).

Cuvette: A cuvette in the sense of the present invention refers to a temperature-controllable vessel, which is closed on all sides and is open at the top, for holding sample liquids and reagent liquids and the resulting reaction mixtures and is used to measure the reaction mixtures by means of photometric and/or luminescence-optical methods. A cuvette in the sense of the present invention has at least one window which is arranged in a side wall of the cuvette and which is transparent for the optical measurement method used, or is optically transparent as a whole.

Stationary cuvette array: This refers to a plurality of cuvettes lined up next to one another, which are arranged in a stationary manner in the analyzer and are not moved along any of the x-, y- and z-axes during normal measurement operation.

Linear cuvette array: This refers to a single row formed of a plurality of cuvettes arranged along a straight line.

Reagent vessel: Vessel or container for holding reagents which are required in order to carry out the analysis.

Sample vessel: Vessel or container which contains, in the analyzer, the analysis sample (the sample to be analyzed) from which multiple smaller sample quantities (aliquots) can be taken in order to analyze individual analytes or parameters. The analysis does not take place in the vessel of the analysis sample, but rather in the cuvette after the reagents have been added thereto, the cuvette in this sense serving as a reaction vessel.

Analysis sample: The material to be analyzed, which is introduced into the analyzer, is referred to as the analysis sample (usually simply called the sample or substance sample). This material is a liquid substance mixture and may be, for example, a body fluid such as blood serum, blood plasma, urine or cerebrospinal fluid. Other substance mixtures are, for example, drinking water, wastewater, wine, beer and fruit juices, and also liquids from chemical and biochemical production processes.

Analyte: Those substances which are contained in an analysis sample and about which information is to be obtained using an analyzer via a chemical analysis with the aid of liquid reagents, that is to say which are quantitatively determined with the concentration being reported, are referred to as the analyte(s) (and also as parameters).

Analysis: The qualitative and/or quantitative determinations of an analyte that is contained in the analysis sample and is to be detected, which are carried out automatically by an analyzer with the aid of liquid reagents, are referred to as an analysis or test (or also as an immunoassay in the case of immunochemical analyses).

Pipetting unit: This refers to the entire system of an automatic pipetting device for transferring liquid between different vessels, which comprises one or more movable pipettors together with all the movable and stationary components necessary for the functioning thereof, including fluidics for supply purposes (hose connections, pumps, valves, containers, etc.), sensors, controller and power supply.

Pipettor: This describes a component of the pipetting unit which is pivotable or linearly movable horizontally in at least one direction relative to the holding vessels (cuvettes, sample vessels, reagent vessels). The pipettor includes a suspended component having at least one pipetting needle which is movable on its own or together with the pipettor and is lowerable into a holding vessel.

Pipetting needle: This refers to a cannula or hollow needle, which is attached to the pipettor, together with the associated support, for aspirating samples from the sample vessels and/or for aspirating reagents from the reagent vessels and for dispensing the aspirated liquids into the cuvettes in a metered manner.

Stationary machine component: A machine component which is arranged in a stationary manner in the analyzer and which is not moved along the linear cuvette array during normal measurement operation.

Movable machine component: This refers to a machine component which is arranged in a non-stationary manner in the analyzer and which can be moved and positioned at least along the linear cuvette array by means of a controlled drive during normal measurement operation.

Optical elements for collimation: These are optical elements for creating a beam that is as parallel as possible. In principle, the light from a more or less punctiform source is transformed into a parallel beam bundle. Optical elements which align in a substantially parallel manner the light coming from an LED are, for example, converging lenses, TIR lenses, parabolic mirrors, and diaphragm arrangements.

Optical elements for filtering: These are optical components, in particular interference filters, for filtering the transmitted light in a wavelength-dependent and/or frequency-dependent manner, that is to say in a color-dependent manner for visible light. Use is made of notch filters, longpass filters, shortpass filters, bandpass filters and dichroic interference filters. Particular preference is given to bandpass filters since these have a high transmittance for a particular wavelength band while absorbing shorter or longer wavelengths.

Condenser or condenser lenses: This is an arrangement of one to two lenses which introduce the largest possible portion of the light from an LED into a cuvette, or is such an arrangement which directs the largest possible portion of the light coming from the cuvette onto a photodiode.

Controlling the temperature of liquid media: Controlling the temperature of liquid media in the sense of the invention comprises both heating a sample/reagent mixture and also particle-containing media or mixtures (suspensions), including stabilization at a target temperature that has been reached.

Analyte/Antigen: An ingredient that is to be qualitatively and/or quantitatively determined in a sample is referred to here as an analyte—also referred to as an antigen in the case of immunoassays. In immunoassays, the analyte is in a liquid phase, usually dissolved in a buffer, in dilute body fluids or other sample liquids. In addition, the analyte may also be a particulate structure with antigenic surface features which is present in a suspension and which can be detected by immunoassays, such as bacteria, viruses, cells or material particles.

Immunoassay: The term immunoassay encompasses a number of bioanalytical methods, the common basic principle of which is that of recognizing and thus detecting an analyte (antigen) in a liquid phase by the binding of an antigen to an antibody. Immunoassays are used, for example, in laboratory medicine for determining a variety of analytes in various body fluids, such as blood, serum, urine or cerebrospinal fluid.

Competitive immunoassay: A competitive immunoassay is used to determine an antigen if either only a single specific antibody is available for this or if the antigen does not have sufficient binding sites for the unhindered binding of two antibodies. By way of example, an antibody (capture antibody) is used as the recognition component and an antigen labeled with a labeling molecule is used as the competitive component.

Sandwich assay: To detect an antigen by means of a non-competitive assay, which is also referred to as a sandwich assay, two different antibodies are required which recognize the antigen and do not hinder each other in terms of their binding to the antigen. Compared to a competitive immunoassay, one particular advantage of this lies in the sensitivity, which is higher in most applications.

Heterogeneous immunoassay: In a heterogeneous immunoassay of the present invention, in contrast to a homogeneous immunoassay, a change of liquid phase takes place during the process. When using magnetic particles with capture antibodies bound thereto for selective binding of the antigen, this may be achieved for example in that the particles are deposited on the vessel wall by a magnetic field, the first liquid is replaced by a second liquid, and the particles are resuspended in the second liquid. Once the first liquid has been removed, any washing steps using the second liquid or a special washing liquid can take place on the particles. The washing steps make it possible to remove substances which have bound non-specifically to the particles, as well as interfering substances present in the first liquid, wherein, by removing interfering substances, the assay becomes much more sensitive and low detection limits and concentration ranges are achieved for the antigen to be determined.

Magnetic particles (magnetic beads): These are magnetic particles of typically a few μm in size, which are suspended in an aqueous buffer solution and which are coated with the capture antibody for immunochemical tests.

Capture antibody: These are antibodies which bind to at least one epitope of the analyte and which are bound to the solid phase—in the case of the present invention—on the surface of solid magnetic particles.

Tracer antibody (labeled antibody, conjugate): These are second antibodies to which a labeling molecule (label) is chemically bound and which binds selectively to analyte molecules by way of antigen/antibody interactions during the assay or competes therewith for binding sites on an antigen (competitive assay). The labeling molecule may be a dye which emits light after one or more chemical substances have been added (chemiluminescence).

Bound/free washing, or (B/F) washing: A process step of a heterogeneous immunoassay, in which the unbound residue of the labeled tracer antibody added in excess is removed from the surface of the magnetic particles by washing.

Dispenser (or injector): A dispenser serves to dispense defined quantities of liquid from a storage vessel, via a supply line which ends in a nozzle, dispensing opening or dispenser needle, into a vessel, for example into a cuvette.

PRIOR ART DOCUMENTS

Analysis systems having movable reaction vessels/cuvettes arranged in a circular manner on turntables (carousel arrangement)

U.S. Pat. No. 8,911,685 B2 (HITACHI) discloses a typical automatic analyzer for carrying out chemical and biochemical analyses of liquid samples by means of photometric measurement methods. Essential features of these analyzers are the reaction vessels which are arranged at the periphery of a turntable and which at the same time act as cuvettes, and also device components which are arranged in a stationary manner around the circumference of the turntable, such as for example pipettors (sample dispenser, reagent dispenser), mixing device, optical measurement device and cuvette washing unit. The temperature control of the cuvettes may be integrated in the turntable, for example in the form of a temperature-controlled water bath. The sample containers are arranged on a sample turntable, and the reagents are located on a reagent turntable.

DE 11 2009 002 702 B4 (HITACHI) discloses another automatic analyzer, the sample containers and reagent containers of which are present in a carousel arrangement. As shown in FIG. 1a of the present application, the analyzer comprises a sample disk A, on which a number of sample containers B for holding a sample can be mounted; a first reagent disk C1 and a second reagent disk C2, on each of which a number of reagent containers D1 and D2 for holding a first reagent and a second reagent can be arranged; and a reaction disk E, on which a number of cuvettes or reaction containers F are arranged in the circumferential direction.

A sample dispensing device G is provided between the reaction disk E and the sample disk A, which sample dispensing device dispenses into the reaction container F a sample that has been aspirated at the sample container B. In addition, a first reagent dispensing device H1 is provided between the reaction disk E and the first reagent disk C1, which first reagent dispensing device dispenses into the reaction container F a reagent that has been aspirated from the reagent container D1 on the first reagent disk C1. Similarly, a second reagent dispensing device H2 is provided between the reaction disk E and the second reagent disk C2, which second reagent dispensing device dispenses into the reaction container F a reagent that has been aspirated from the reagent container D2 on the second reagent disk C2. The sample dispensing device G and the two reagent dispensing devices H1 and H2 are arranged in a stationary manner at defined points around the circumference of the reaction disk E.

Two stationary stirrers J1, J2 which stir the liquid in the reaction containers F after the first reagent and the second reagent have been dispensed, a light source K which sends light through the reaction containers F, and a container cleaning mechanism L for cleaning the reaction containers F are provided at the outer circumference of the reaction disk E in this order in the direction of rotation of the reaction disk E.

A stationary spectroscopic system M is arranged in a position opposite the light source K such that the reaction disk E is located therebetween. A signal processing circuit N, which processes the signals from the spectroscopic system M, is provided in the vicinity of the spectroscopic system. The signal processing circuit N is connected to a computer (not shown). The automatic analyzer additionally also comprises a controller S which controls the operation of the analyzer.

Such analyzers are characterized in that all the processes are predefined by rigid clock cycles of the carousel and must take place in predetermined time windows. Actions such as dispensing, mixing, measuring and washing can take place only when the respective cuvettes are located at the positions of the respective device components.

For instance, a sample can be dispensed into an empty cuvette (not at any time but) only when the empty cuvette is moving past the position of the sample pipettor and the cuvette carousel stops at this position. A reagent can be dispensed into a cuvette containing the sample only when the cuvette in question is moving past the position of the reagent pipettor and the cuvette carousel stops at this position. The same applies to the stirring of reaction mixtures consisting of the sample and the reagents in the cuvettes by mechanical stirring, and to the optical measurement at the position of the optical measurement device.

For example, a particular cuvette also cannot be optically measured at any time or repeatedly at small time intervals, since it is first necessary to wait until the cuvette in question is located at the position of the optical measurement unit or is being guided past the latter "on the fly" during the measurement.

When reactions are complete, measurements cannot be carried out immediately, and in the case of kinetic measurements the time intervals between the individual measurements are relatively large (at least one revolution of the turntable). It is disadvantageous that, when measurements are complete, a cuvette cannot be immediately washed and made available for a new test. A cuvette can be washed and made available for a new test only when the cuvette in question is located at the position of the cuvette washing station and a washing stop takes place (is provided) at the position in question at a fixed point in time or for a fixed duration from the start of the test, according to the cycle times which in this concept are rigidly predefined. As a result, all the cuvettes are "blocked" for the same length of time, regardless of whether the measurement duration on the respective test is short or long.

The rotationally organized carousel arrangement with moving samples, reagents and cuvettes, but in particular the carousel concept with movable cuvettes and stationary machine components, results in relatively high throughput times for the individual tests and limits the number of tests that can be carried out per hour on a device having a particular number of cuvettes.

Analysis systems having stationary reaction vessels/cuvettes arranged in a circular manner U.S. Pat. No. 5,178,833 A (BOSEMA) discloses an automatic analyzer having measurement cuvettes and reagent vessels which are arranged in a circular manner and which are stationary relative to the device, the measurement cuvettes being arranged in an outer ring and the reagent vessels being arranged in two inner rings. The axis of rotation of a stationary pipettor is positioned in the center of the reagent vessel ring, said axis of rotation being encircled by a ring-shaped washing vessel for the lowerable pipetting needle of the pipettor. The sample vessels of the analyzer are located on a separate turntable at the periphery of the stationary cuvette ring. An optical measurement unit reaches the measurement cuvettes by means of a rotational movement about the central axis of the analyzer. The optical path leads through the liquid surface along the longitudinal axis of the individual measurement cuvettes. The pipetting needle reaches the sample vessels, the measurement cuvettes, the reagent vessels and the washing vessel by means of rotational movements of two horizontal arms of the pipettor about a first, central axis and a further axis.

It is disadvantageous that the disclosed configuration permits only one independently movable pipetting needle for samples and reagents, that the reagent store is limited to the area of the inner stationary rings, and that the optical path extends through the surface of the reaction liquid. It is particularly disadvantageous that the measurement cuvettes cannot be washed, but instead must be replaced by the outer ring in sectors after use.

Analysis systems having movable reaction vessels/cuvettes arranged in a linear manner GB 1 321 754 A discloses an automatic analyzer having reaction vessels/cuvettes which are attached to circulating endless belts that can move in a linear manner.

US 2014/0287523 A1 (ABBOTT) likewise discloses an analyzer having reaction vessels or cuvettes which are arranged in a linear manner on belts. The linear endless belts are tensioned on two pulleys, with appropriate reaction vessels being attached in the longitudinal direction, for example in a "pretreatment lane" and in a "primary process lane". By rotating the pulleys, the reaction vessels or cuvettes can be moved back and forth in the running direction of the belt and can also move around the pulleys on the underside. The arrangement amounts to a "linear variant" of the conventional carousel arrangement, in which the reaction vessels or cuvettes move on a circular path. However, one feature common to both variants is that the reaction vessels or cuvettes are still moved relative to the device and are driven toward the processing stations (machine components). Therefore, substantially the same disadvantages as already mentioned in point A) occur.

WO 99/046601 A1 (HITACHI) discloses a linear, movable cuvette array with stationary device components (dispensers for sample liquid and reagents, mechanical stirrers, photometer and cuvette washing station).

As shown in FIG. 1b of the present application, in WO 99/046601 A1 a plurality of cuvettes or reaction vessels 2 are arranged at predetermined spacings in a support frame or a transport bar 7 in a temperature-controlled chamber (water bath) 1. The cuvette contents are mixed for example by means of ultrasound. The transport bar containing the reaction vessels 2 is moved linearly in the direction of the arrow 9 by means of a drive unit 8. Also provided in addition to the temperature-controlled chamber 1 are a sample pipetting unit 3a, a reagent injection unit 3b, an optical measurement unit 4, a cuvette washing unit 5, and a first stirring mechanism 6a and a second stirring mechanism 6b for stirring the contents of the reaction vessels 2 again. The stirring mechanism 6a or 6b may also be configured as an ultrasonic generator, which acts on the reaction vessels 2 via the water bath in the chamber 1. In this embodiment variant, the water in the temperature-controlled chamber 1 is kept at a constant temperature, at which the reactions can take place and the optical measurement can be carried out.

During operation of the device, a reaction vessel 2 stops at the sample pipetting unit 3a, which dispenses the sample into the reaction vessel 2. Likewise, the reagent injection unit 3b discharges the reagent used for the analysis into the corresponding reaction vessel 2. In addition, the first stirring mechanism 6a stirs in order to mix the reaction solution, and the second stirring mechanism 6b stirs the mixture in the reaction vessel 2 again. The optical measurement unit 4 measures the absorption in the corresponding reaction vessel. Furthermore, the cuvette washing unit 5 discards the tested reaction solution and cleans the reaction vessel 2. Once these processes are complete, the drive unit 8 starts to move the reaction containers 2. As the reaction containers 2 move onward, the sample pipetting unit 3a, the reagent injection unit 3b, and the first and second stirring mechanisms 6a, 6b are washed in a cleaning unit. A number of chemical analyses are carried out by repeating the process above. As can be seen from the process above, the individual components of the device must be arranged in the stated order along the movement direction 9.

One disadvantage of this concept is that the transport bar 7 inevitably requires, to the left and to the right of the stationary device components 3a, 3b, 6a, 6b and 5, a large amount of free space for the linear movement of the reaction vessels 2. The longitudinal axis of the analyzer thus inevitably increases by at least twice the length of the transport bar 7.

The cuvettes or reaction vessels 2 of the device according to WO 99/046601 A1 are thus moved past the stationary device components, in a manner analogous to the turntable variant described above. The system is inflexible, and substantially the same disadvantages as already mentioned in point A) occur.

Systems having stationary reaction vessels/cuvettes arranged in a circular and/or linear manner EP 2 309 251 A1 (SIEMENS) discloses an automatic analyzer having stationary sample vessels or cuvettes which are present in a circular or linear arrangement, wherein the optical measurement unit is formed on a rotatable device such as to be movable along the sample vessels. According to one embodiment variant, the rotatable device, which carries the light source in the form of an LED and the photodetector in the form of a photodiode, may be arranged below the receptacle for the sample vessels, as a result of which it is possible at all times to access the sample vessels by means of a gripping arm. The rotatable device may also have a plurality of LEDs of different wavelengths and a plurality of photodiodes, so that the samples can be measured at multiple wavelengths. The photodiodes may be replaced by a CCD element.

The arrangement described in EP 2 309 251 A1 is unsuitable for clinical chemical analyzers (CC analyzers) and is directed to an analyzer for hemostatic measurements (for determining blood coagulation). This arrangement may also be part of a system composed of multiple devices (for example PCR analyzer, cooling device). The sample vessels are not reused, but instead are optionally passed on to other components of a system, for example are disposed of by means of a gripping arm or after the coagulation parameters have been determined.

Only whole blood (blood plasma with the blood cells contained therein) in a form that is as undiluted as possible is suitable as a sample in the case of coagulation measurements. In contrast, whole blood is completely unsuitable for the photometric measurements of the present CC analyzer, since the blood cells scatter the light and thus the measurement results would be distorted. Therefore, CC analyzers always use blood plasma or blood serum, which in addition is heavily diluted by the addition of reagents.

According to EP 2 309 251 A1, the vessels with the samples therein (optionally after the addition of reagents) are used directly for the optical measurement.

In a CC analyzer, measurements are always carried out using cell-free blood plasma/blood serum which is introduced into the device by means of sample vessels, after which aliquots of the samples are transferred by means of a pipettor, together with reagents, into separate cuvettes, which are then subjected to a photometric measurement.

Laboratory robots and automatic pipetting and analysis devices for preparing and/or analyzing samples using stationary reaction vessels/cuvettes in a 2D arrangement (microtiter plate)

A typical analysis device for carrying out biochemical analyses of liquid samples using microtiter plates is known for example from EP 0 259 386 B1 (TECAN). The analysis device comprises a primary rack for holding a plurality of sample vessels, a cross-table which can be positioned next to the primary rack in the x-y direction and which is designed to hold a microtiter plate, a sample distributor arm which is arranged above the primary rack and the cross-table and which can be positioned as desired in an upper horizontal plane, and a photometer which is arranged within the positioning area of the cross-table and the beam path of which passes perpendicularly through the x-y plane of the cross-table.

Another example of a machine for automatically preparing and analyzing samples in the wells of a microtiter plate is known from DE 10 2004 057 450 B4 (CYBIO).

There are many machines of this type which use microtiter plates for detecting and determining substances. Microtiter plates contain a large number of mutually isolated wells in rows and columns (2D arrays). They are used for a wide range of procedures. The pipetting takes place either manually or, in the case of high throughput screening (HTS), with the aid of pipetting robots. Photometric determinations, for example absorption measurements on microtiter plates in transmitted light using photometers, take place in such a way that the beam path passes through the well in a perpendicular direction through the liquid surface. However, for precise quantitative determinations, it is essential to guide the light beams through the measurement liquid over paths and distances which are known and which are defined as precisely as possible. Any light scattering on particles, turbidity, inlet faces, surfaces (for example liquid surface, cuvette wall) leads to light losses, which on the other hand distort the measurement result.

EP 2 410 342 A2 (HOFFMANN-LA ROCHE) discloses a pipetting device having a pipettor with multiple flat frame elements which are arranged next to one another and which, together with the pipetting needles thereof, are jointly movable on a main frame body in a horizontal x-direction that is normal to the main frame body. The pipetting device serves to transfer samples or reagents from a first row of vessels to a second row of vessels which is offset in the x-direction. The pipetting needles are first adjusted in the y-direction to the spacing of the vessels of the first row in order to take up sample liquid or reagent liquid, and then are adapted to the spacing of the second row of vessels in order to dispense the sample liquid or reagent liquid. However, an independent movement of two pipetting needles in the x- and y-direction is not provided. Movement modules for the y-direction and the z-direction (lifting and lowering of the pipetting needles) are arranged in gaps in flat, adjacent frame elements in order to keep the spacing between the individual pipetting needles small. However, an independent movement of the pipetting needles in the y-direction is possible only to a limited extent. For example, it is not possible for the frame elements on the transfer arm to move past one another, which results in a mutual restriction of the freedom of movement of the pipetting needles in the y-direction. Such pipetting devices find a useful application in connection with microtiter plates in particular.

EP 1 230 553 B (MAXMAT) discloses a chemical or biological analyzer which has a storage module for sample tubes and tubes for reagents. Also provided is an analysis module having a reaction container in the form of a microtiter plate and a sample-taking module (pipettor) which is movable on a rail and which has two pipetting needles arranged at a fixed distance from one another, which pipetting needles operate independently of one another in the z-direction in order to take samples automatically and are each equipped with a retractable aspirating pipette for transferring predetermined quantities of samples and reagents from the storage module to the analysis module. The two pipetting needles are movable only jointly in the horizontal x/y plane.

The analysis module has a heating plate for the microtiter plate, which heating plate is arranged close to the lower region of the wells of the microtiter plate in order to heat the contents of the wells by convection. The sample-taking unit further comprises a mixing device which is controlled by an electromagnet in order to bring about an alternating back-and-forth movement of the pipetting needle when the latter is in a lowered position in a well of the microtiter plate, so as to thoroughly mix the mixture consisting of samples and reagents.

U.S. Pat. No. 5,897,837 A (TOA MEDICAL) discloses a pipetting machine suitable for pretreating samples for an immunoassay analyzer, having a first block of a pipettor which is movable horizontally in the x- and y-direction and which is equipped with two pipetting needles next to one another, it being possible for said pipetting needles to be lowered or lifted independently of one another. In this case, one of the two needles may be assigned to reagents, and the other needle may be assigned to samples. In addition, a second block is also present, which is movable in the x-y direction and has a lowerable pipetting needle. In order to clean the needles, it is necessary to move to a stationary needle washing station. The two pipetting needles of the first movable block can disadvantageously only be moved jointly in the horizontal x/y plane. This has the disadvantage that the weights of the robotics components of the pipettor cannot be distributed across the two horizontal movement axes x and y, so that the weight of the second pipetting unit must always also be accelerated in order to move to positions in the y direction. Likewise, the weight of the needle washing unit together with the needle washing vessel must also always be accelerated in both horizontal directions. Furthermore, due to the joint horizontal movement, it is not possible to use both needles simultaneously for pipetting at different, non-adjacent positions of a vessel row.

Optical System Components for Automatic Analyzers

U.S. Pat. No. 8,675,187 B2 (Hitachi) describes an optical measurement unit for obtaining measurement signals from liquid media, and an analysis system equipped therewith. As shown in FIG. 2a of the present application, one of multiple reaction vessels 24 arranged in a circular manner on a turntable 23 is immersed in a temperature bath 25, which is filled with water 26 at a constant temperature. A photometer 27, which is fixedly arranged in the temperature bath 25, has an LED light source 28, the light from which is irradiated into the sample 31 present in the reaction vessel 24 by means of a condenser lens 29 and a deflecting mirror 30. A semiconductor laser may also be used as the light source. A photodetector 32 of the photometer 27 is arranged on the opposite side of the reaction vessel 24. Diaphragms 34 for the inlet and outlet radiation are provided on the inlet side and on the outlet side of the reaction vessel 24 at the measurement position 33 of the photometer 27. One disadvantage is the mechanical and metrological complexity associated with reaction vessels which are arranged in a circular manner on a turntable, since the individual reaction vessels 24 have to be moved into a measurement position of the photometer 27 in order to measure the samples.

US 2013/0301051 A1 (Pogosyan) describes a cost-effective, portable photometer which—as shown in FIG. 2b of the present application—has a plurality of LEDs of different wavelengths as the light sources 35 and a photodiode or a photomultiplier as the detector 36. The photometer can be used to analyze chemical, biological or pharmaceutical samples which are located in a sample holder 37 between the light sources 35 and the detector 36. The light from the light sources 35 is directed onto a light-scattering surface 39—optionally after passing through an interference filter 38—and passes through a collimator lens 40 and a slit diaphragm 41 in order to reach the sample present in the sample holder 37. As shown, the detector 36 can be pivoted from a first position to a second position. In the illustrated geometry, a collimator lens functions optimally if the scattering surface is selected to be very small, almost punctiform, but this reduces the light output.

U.S. Pat. No. 8,064,062 B2 (Beckmann) discloses—as shown in FIG. 2c of the present application—a photometer with a stationary LED array comprising the light sources L1 to L5 and a stationary detector array comprising the photodiodes R1 to R5, wherein one photodiode is assigned to each light source. The cuvettes C located on a turntable are arranged between the LED array and the detector array. During a rotational movement of the cuvettes C in the direction of the arrow, the optical beam paths are crossed and the light of the different wavelengths $\lambda 1$ to $\lambda 5$ can be successively applied to the samples in the cuvettes C.

AT 510 631 B1 (SCAN Messtechnik) claims a spectrometer having multiple LEDs as the light source 44, as shown in FIG. 2d of the present application. The spectrometer is used to analyze the contents of a liquid 42, by means of the light source 44 and a detector 45, wherein the light from the light source 44 having a predefined spectral range is passed through an inlet window 47, through the liquid 42 to be examined, and through an outlet window 48 to the detector 45. The light source 44 is formed by a plurality of LEDs 49 which are arranged in a mount 50 and which are connected to control electronics 43, said LEDs being designed to emit light of different wavelength ranges within the predefined spectral range. The control electronics 43 are designed to actuate the light-emitting diodes 49 in sequence, wherein a compensation detector 51, which is connected to the control electronics 43, is arranged opposite the light-emitting diodes 49 in the mount 50. A lens 46, a diaphragm 52 and a converging lens 53 are arranged in the beam path between the light source 44 and the inlet window 47. In order to measure the scattered light of the liquid to be examined, a further detector 54 may be arranged transversely to the measurement radiation.

WO 2010/122203 A1 (Biosystems) discloses a photometer, which is based on an arrangement of multiple LEDs as the light source, for measuring the absorption and turbidity of a sample present in a cuvette. In this case, the light from the individual LEDs is coupled into the beam path upstream of the sample by means of a beam splitter together with a bandpass filter. In addition, a reference photodiode is arranged on the light source side. A photodiode is arranged in the beam path downstream of the sample, on the detection side. The individual cuvettes are moved past the photometer. Disadvantageously, the light source is of very complex construction and consists of many individual components. In addition, the light from the LEDs located further away from the cuvette has to pass through multiple beam splitters, which leads to intensity losses.

U.S. Pat. No. 4,234,539 (Coulter Electronics) describes an automatic analyzer having turntables for sample vessels, reagent vessels and reaction vessels (cuvettes), with pipetting arms installed therebetween for transferring the media. Arranged concentrically in relation to a cuvette turntable is a rotor, on which pairs of light sources and photodetectors which are positioned fixedly with respect to one another are arranged. Upon suitable positioning and/or rotation, the individual cuvettes come to lie between the light source and the photodetector. In an alternative embodiment, a single light source is positioned centrally on the axis of rotation and the photodetectors are located (as seen in the radial direction) on the opposite side of the cuvettes. While the cuvette turntable then rotates only slowly, the rotor having the light source executes a much faster rotational movement, which leads to a significant increase in the measurement frequency. Furthermore, the rotor may have a filter wheel with different filters, which can be brought into the beam path between the central light source and the cuvette. However, the rotor must stop at each cuvette, after which the respective filter is selected by rotating the filter wheel. The above-described disadvantages of turntable systems and of cuvettes attached to turntables nevertheless also exist here.

EP 2 309 251 A1 (Siemens Healthcare) discloses an automatic analyzer having stationary sample vessels or cuvettes which are present in a circular or linear arrangement, wherein the optical measurement unit is formed on a rotatable device such as to be movable along the sample vessels. According to one embodiment variant, the rotatable device, which carries the light source in the form of an LED and the photodetector in the form of a photodiode, may be arranged below the receptacle for the sample vessels, as a result of which it is possible at all times to access the sample vessels by means of a gripping arm. The rotatable device may also have a plurality of LEDs of different wavelengths and a plurality of photodiodes, so that the samples can be measured at multiple wavelengths. The photodiodes may be replaced by a CCD element.

System Components for Mixing and Temperature Control for Automatic Analyzers

A temperature-controllable cuvette arrangement has become known from DE 27 26 498 A1 (HELLMA). As shown in FIG. 2e of the present application, a temperature-controllable cuvette block 55 is provided which has a plurality of receiving shafts 56, into which cuvettes 57 can be inserted. The cuvettes 57, which taper conically in the downward direction and have lateral measurement windows 58, are inserted with a form fit into a U-shaped adapter 59 which has good thermal conductivity and which thus establishes thermal contact with the cuvette block 55 via the walls 60 of the receiving shaft 56. The sample/reagent mixture in each of the cuvettes 57 can in each case be optically measured through a measurement channel 61 in the cuvette block 55.

One disadvantage here is that the temperature of the sample/reagent mixture heats up only slowly to the temperature of the cuvette block. It is thus more difficult to achieve a high sample throughput in an analyzer, since the temperature control when analyzing a sample always counts among the processes that take the most amount of time.

JP 2007-303964 A (OLYMPUS) discloses—as shown in FIG. 2f of the present application—a device for controlling the temperature of cuvettes 62 which are arranged in receptacles of a rotatable carousel 63. The device has a piezoelectric substrate 64 which is attached to the side wall of each cuvette 62 and on which there is integrated both an electrode structure of an interdigital transducer (IDT) as an ultrasonic transducer 65 and a temperature sensor 66 for non-invasively measuring the temperature of the cuvette contents. A temperature regulating unit 68 of a control unit 69, which is connected via sliding contacts 67, forms together with the driver unit 70 for the ultrasonic transducer 65 a control loop for controlling the temperature of a reaction mixture in the cuvette 62. The sample/reagent mixture is heated directly to the target temperature by absorbing ultrasonic energy.

One disadvantage here is that each cuvette 62 requires an adhesively bonded piezoelectric substrate 64 with an integrated temperature sensor 66, which must be brought into contact with an electronic regulating unit 68. In addition, the temperature measured on the substrate of the ultrasonic transducer 65 may be distorted by the self-heating of the ultrasonic transducer and thus does not correspond to the temperature of the sample/reagent mixture in the cuvette 62.

Furthermore, the temperature sensor 66 is not in contact with the liquid, but rather can sense the temperature of the liquid only indirectly via the heat conduction of the vessel wall of the cuvette 62, as a result of which, particularly in the case of very rapid heating of the liquid, a rise in temperature in the liquid cannot be measured with sufficient speed and accuracy to be able to rule out a lasting or transient exceeding of the target temperature by a value that is critical for the sample constituents.

EP 1995 597 A1 (OLYMPUS) discloses a device for stirring liquids in cuvettes 71 which—as shown in FIG. 2g of the present application—are arranged on a rotatable carousel 72, wherein a sound generator 73 (interdigital transducer (IDT)) for irradiating ultrasonic energy into the cuvette 71 is adhesively bonded to the side wall of each cuvette. According to EP 1995 597 A1, however, measures must be taken to limit an undesired increase in temperature of the cuvette contacts which occurs as a result of sound absorption, and to prevent distortion of the analysis results due to thermal damage.

The critical heat input brought about by operation of the sound generator 73 is calculated by thermal characteristics of the cuvette contents, which are stored in a control unit 74. The heat input can be limited to a non-harmful value by limiting the operating time, by modulating the amplitude, or by varying the operating frequency of the ultrasonic generator. According to a further measure for limiting the heat input, a dedicated Peltier element 76 can be applied directly to the substrate of the adhesively bonded sound generator 73 by means of an actuator 75 for each cuvette 71, in order to actively cool said sound generator during operation. The power of the Peltier element 76 is controlled via stored operating parameters, no temperature measurement being provided on the Peltier element. The signal generator 77 for the sound generator 73 is actuated by a driver unit 78 of the control unit 74.

A precise temperature control of the liquids in the cuvettes 71 by suitable parameterization alone is thus not possible or provided since a precalculated input of ultrasound would on its own be too inaccurate to achieve a target temperature.

In order to control the mixing or stirring process more precisely, and to ensure that a harmful temperature value is not exceeded during stirring, a temperature measurement of the liquid may be carried out from above by a stationary infrared sensor, but this can be carried out in each case only on one particular cuvette of the carousel while the latter is at a standstill.

Compared to a block temperature control in a cuvette holder of constant temperature, a temperature control having the aforementioned technical features has the disadvantage that the system can be regarded as not inherently safe with regard to exceeding the target temperature during the heating and regulation.

JP 2007-010345 A (OLYMPUS) describes an ultrasonic stirring device, by which the contents L of a cuvette 81 can be mixed. As shown in FIG. 2h of the present application, a piezoceramic ultrasonic generator (thickness-mode transducer 83) is adhesively bonded to the bottom 82 of the cuvette 81, wherein the shape and the material of the cuvette bottom forms an acoustic lens 84 for focusing the ultrasonic energy at the point F just below the liquid surface. The thickness-mode transducer 83 made of lead zirconate titanate ("sounding body") comprises a flat disk 85 with flat electrical contacting 86 on both sides, having a diameter which is larger than that of the cuvette bottom 82.

System Components for Carrying Out Luminometric Measurements for Automatic Analyzers U.S. Pat. No. 7,998,432 B2 discloses an automatic analyzer for carrying out biochemical (clinical chemical) tests and blood coagulation tests, which are measured photometrically, the analyzer also being suitable for carrying out heterogeneous immunoassays by means of luminescence detection. The device described in FIG. 1c of the present application is substantially divided into a region 120 for storing samples and reagents and a region 121 for carrying out optical measurements and analyses. A pipetting device 122 can move along the two regions 120 and 121 and thus can pipette liquid samples and reagents from the storage region 120 into the cuvettes on a rotatable cuvette carousel 123. The cuvette carousel 123 is brought to a constant temperature from below by means of a ring-shaped temperature control device. Via respectively provided transfer mechanisms, individual cuvettes can be exchanged in the radial direction—when the cuvette carousel is at a standstill—between the slot-shaped cuvette receptacles of the carousel and the stationary stations of the analyzer which are arranged around the cuvette carousel 123. A station 124 is provided for the photometric measurement, a station 125 is provided for discharging cuvettes that are to be discarded, and a station 126 is provided which has a dispenser for dispensing coated magnetic nanoparticles from a storage region 127, in which washing reagents and trigger reagents for the luminescence measurement are also located. Further stations serve for magnetic sedimentation and B/F washing 128, luminescence measurement 129, coagulation measurement, or dilution of samples. A magazine for supplying single-use cuvettes is denoted by 130. One disadvantage is the considerable mechanical complexity associated with transferring the cuvettes between the receptacles of the cuvette carousel 123 and the individual stations of the analyzer. Although in some stations (see 128, 129)—due to the fact that the cuvettes are moved out of the system—measurement and preparation steps take place which are decoupled from the clock rate of the cuvette carousel 123, the transferring of cuvettes to and from said positions is still dependent on this clock rate, as are those actions in which the cuvettes remain in the carousel (photometric measurement in the station 124 and addition of the magnetic beads in the station 126). The disadvantages already discussed in point A) in connection with carousel arrangements thus apply.

U.S. Pat. No. 6,333,008 B1 discloses a measurement arrangement which serves to carry out luminometric series analyses on liquid samples containing target substances to be detected and labeling substances which can be bound thereto in an immunochemical detection reaction, as well as magnetizable carrier particles. The liquid samples are transported in wells of a multi-well cuvette along a conveying path to an optical measurement station, wherein permanent magnets, which are configured as rotatable double magnets, and separation stations, which are intended to separate out excess labeling substance, act on the multi-well cuvette while the latter is being transported. In each of the individual separation stations, a (B/F) washing step takes place by means of an injector and an aspirating needle. In the measurement station, the luminescence radiation is detected by a photodetector. One disadvantage of the known measurement arrangement is the need to have to convey the liquid samples, during the analysis process, to different machine components which are distributed in a stationary manner on a process path. In addition, certain components, such as permanent magnets configured as rotatable double magnets and separation stations having injectors and aspirating needles, must be provided multiple times.

Such devices are characterized in that all the processes are predefined by rigid clock cycles of the cuvette conveying mechanism and must take place in predetermined time windows. Actions such as dispensing, mixing, separating and measuring can take place only when the respective cuvettes are located at the positions of the respective device components.

For instance, a sample can be dispensed into an empty cuvette (not at any time but) only when the empty cuvette is moving past the position of the sample pipettor and the cuvette conveying mechanism stops at this position. A reagent or a washing liquid can be dispensed into a cuvette containing the sample only when the cuvette in question is moving past the position of the reagent dispenser and the cuvette conveying mechanism stops at this position. The same applies to the stirring of reaction mixtures consisting of the sample and the reagents in the cuvettes by mechanical stirring, and to the optical measurement at the position of the optical measurement device.

For example, a particular cuvette also cannot be optically measured at any time or repeatedly at small time intervals, since it is first necessary to wait until the cuvette in question is located at the position of the optical measurement unit.

SUMMARY OF THE INVENTION

One object of the invention is to avoid, in automatic analyzers for carrying out chemical, biochemical and/or immunochemical analyses of liquid samples, the disadvantages mentioned above, particularly in connection with the sample throughput of known systems, which is limited by the processes that are predefined by rigid clock cycles and that take place in predetermined time windows, and to propose improvements which increase the sample throughput without significantly increasing the cost of the individual analysis or of the analyzer, while at least maintaining the quality of the analysis. In addition, the aim is to propose an improved method for automatic chemical, biochemical and/or immunochemical analysis of liquid samples.

This object is achieved according to the invention by an analyzer having cuvettes for receiving the liquid samples and reagents, wherein a plurality of cuvettes is arranged as at least one stationary, linear cuvette array in the analyzer, having movable and stationary machine components, at least comprising:

a pipettor which is designed to be movable in the x-direction along a line of movement defined by the linear cuvette array, said pipettor being equipped with at least one pipetting needle which is designed to be lowerable in the z-direction into the cuvettes and which is designed to be movable in a y-direction, substantially normal to the x-direction, between the cuvettes and the sample store and/or the reagent store, a mixer unit for mixing the samples and reagents in the cuvettes, an optical measurement unit which, in order to obtain a measurement signal, receives measurement radiation that exits through a measurement window arranged on the side of the cuvette, a cuvette washing unit, designed to be movable in the x-direction, for cleaning the cuvettes, a needle washing unit for cleaning the at least one pipetting needle, and a stationary temperature control unit for setting a predefinable measurement temperature in the cuvettes, wherein at least two machine components are designed to be movable in the x-direction independently of one another along or parallel to the line of movement defined by the linear cuvette array and each have access to different cuvettes or groups of cuvettes in a freely selectable order.

The method according to the invention for automatic chemical, biochemical and/or immunochemical analysis of liquid samples, which are present in a sample store of an analyzer, with the aid of liquid reagents, which are present in at least one reagent store of the analyzer, in order to determine at least one analyte concentration in the sample, is characterized by the following steps:

- transferring a predetermined quantity of a liquid sample from a sample vessel in the sample store into a cuvette of a stationary, linear cuvette array by means of a first pipettor which is movable along the cuvette array;
- transferring a predetermined quantity of a reagent liquid from a reagent vessel of the reagent store into the cuvette of the stationary, linear cuvette array by means of the first pipettor or by means of a second pipettor which is movable independently of the first;
- mixing and controlling the temperature of the liquids in the cuvette;
- optionally transferring a predetermined quantity of a further reagent liquid from a reagent vessel of the reagent store into the cuvette of the stationary, linear cuvette array by means of the first or second pipettor, optionally once again mixing and controlling the temperature of the liquids in the cuvette;
- optically measuring the contents of the cuvette by means of an optical measurement unit and determining at least one measured value;
- calculating and displaying the analyte concentration based on the determined measured values and on previously known or predetermined reference values and calibration values;
- washing and drying the cuvette by means of a cuvette washing unit which is movable along the cuvette array; and
- providing the cuvette for subsequent analysis.

According to the invention, therefore, two machine components are necessarily designed to be movable in the x-direction independently of one another: the pipettor (in the simplest case a single pipettor having a single pipetting needle) and the cuvette washing unit. The mixer unit and the optical measurement unit may be stationary or movable, and the temperature control unit is necessarily configured in a stationary manner. It should also be noted that two different, movable machine components which access the cuvette openings cannot access the same cuvette simultaneously. In practice, however, it is in any case not necessary for the pipettor and the cuvette washing unit, for example, to access the same cuvette "simultaneously". It should also be noted that stationary machine components are configured such that they access each cuvette anyway, for example as a result of the fact that one such machine component is assigned to each cuvette or group of cuvettes.

Due to the free choice of access of the machine components which are movable in the x-direction, in particular of the cuvette washing unit to any desired cuvettes and of the at least one pipettor (having at least one pipetting needle) to any desired sample vessels, reagent vessels and cuvettes, the throughput increases significantly compared to a machine having the same number of cuvettes which is organized in a rotational manner.

According to one advantageous embodiment variant of the invention, the analyzer has two pipettors which are movable in the x-direction independently of one another.

Compared to the variant having one pipettor, this leads to a further increase in throughput due to the fact that the first pipettor can pipette samples into a first cuvette while the second pipettor can simultaneously pipette reagents into a freely selectable second cuvette.

According to the invention, it is also provided that at least one pipettor has two pipetting needles which are movable in the y-direction independently of one another and parallel to one another. The two pipetting needles of a pipettor can thus move past one another, independently of one another, along the same distance in the y-direction, without colliding.

According to this advantageous variant, two different needle types can also be used (for example for different pipetting volumes, with specific coatings for different types of sample and reagent, without requiring another pipettor or a needle exchange station).

One particularly advantageous variant of the invention provides that the needle washing unit is arranged on the pipettor and is designed to be movable therewith.

The measure whereby one pipetting needle can pipette while the second pipetting needle is simultaneously being cleaned also serves to increase the throughput. Advantages are obtained even when there is just one pipetting needle on the pipettor, since the pipettor need not stop at a stationary needle washing unit each time. Since the y-movement of the respective pipetting needle can take place independently of the needle washing unit carried on the pipettor, the moving masses of the robotics components can be split across the two horizontal axes, so that the needle washing unit only has to be accelerated in the x-direction.

A further object of the invention is to improve an optical measurement unit and an optical measurement method for obtaining measurement signals from liquid media which are held in cuvettes lined up next to one another, such that a plurality of measurements at different wavelengths can be carried out in the course of the chemical reactions in the individual cuvettes and in short temporal succession, the aim being to reduce to the greatest possible extent the kinematic complexity brought about by translational and/or rotational relative movements between individual components of the measurement system.

This further object is achieved according to the invention in that the optical measurement unit is equipped with a light-supplying unit which has a plurality of LED light sources emitting in a spectrally different manner in the UV/VS/NIR wavelength range, and also with a stationary detection unit which is configured such that at least one photodiode is fixedly assigned to each cuvette of the cuvette array.

It is particularly advantageous that the cuvettes are arranged as an immovable, stationary cuvette array, wherein the individual detectors (transmitted-light detector (for photometric and turbidimetric measurements) and/or scattered-light detector (for nephelometric measurements)) are fixedly assigned to each cuvette, and that the light exiting from the individual cuvettes—that is to say also any dark signals and possibly incident ambient light—can be measured from each cuvette in a temporally unlimited manner for the purpose of correction. It is thus not necessary to measure when moving past the detectors, or to position a detector sequentially in front of a plurality of cuvettes in stop-and-go operation. As a result, more accurate measurement results can be obtained in very short time intervals, and measurement processes are made much more flexible.

According to a first variant of the invention, the light-supplying unit has at least one stationary light distributor device which distributes the light from the individual LED light sources among the individual cuvettes of the cuvette array, wherein the light distributor device has a cavity, the inner surfaces of which are designed to be at least partially mirrored and/or diffusely reflective, and wherein the light distributor device has, for each LED light source, an inlet opening for feeding the light into the cavity, and wherein the light distributor device has, for each cuvette of the cuvette array, an outlet opening for feeding the light into the cuvette.

This is a compact, cost-effective variant, since the light distributor device, which accommodates a plurality of LED light sources of different wavelength, is assigned in a stationary manner to a row of cuvettes. In the case of cuvette arrays having a large number of cuvettes, the stationary cuvette array may be segmented, wherein a separate light distributor device is fixedly assigned to each segment. Overall, therefore, this results in an optical measurement unit which has no moving components.

For better distribution of the light irradiated into the light distributor device by the individual LED light sources of different wavelength, the inner surface of the light distributor device that is located opposite the inlet openings of the LED light sources is preferably designed to be corrugated and reflective. Although different light paths may occur between individual LED light sources and cuvettes, it is possible on account of the constant geometric conditions for intensity differences to be compensated by calculation, by parameterization of the hardware setup and/or by calibration measurements.

In order to homogenize the measurement radiation entering the cuvettes, the inner surface of the light distributor device that is located opposite the outlet openings to the cuvettes is designed to be diffusely reflective.

According to a second variant of the invention, the light-supplying unit has at least one unidimensional, rod-shaped light source array comprising a plurality of LED light sources, which light source array is oriented along the stationary cuvette array and is movable along the stationary cuvette array such that each LED light source of the light source array can be assigned to each cuvette of the stationary cuvette array.

This variant benefits from the fact that, on the detector side, the photodiodes fixedly assigned to the individual cuvettes of the stationary cuvette array are present as a stationary, linear photodiode array and are preferably arranged on a common circuit board. The slight disadvantage of a rod-shaped light source array which is movable along the stationary cuvette array is balanced out by cost-effective manufacture (only one light source array for a plurality of cuvettes).

According to a third variant of the invention, the LED light sources of the light-supplying unit are arranged as a 2D LED array, wherein a stationary 2D LED array is fixedly assigned to each cuvette of the stationary cuvette array.

This variant enjoys the advantages of the first variant described above, since the optical measurement unit can be realized without moving components and each cuvette has an individual photometer, having a fixedly assigned 2D LED array as the light source and a fixedly assigned photodiode as the detector.

An optical measurement method according to the invention for obtaining measurement signals from liquid media, in particular in connection with the first variant of the invention, is characterized by the following steps:
  receiving the liquid media in cuvettes which are lined up next to one another and which form a stationary cuvette array,
  supplying an inlet radiation, which radiates into the cuvettes, by means of at least one stationary light distributor device which optically contacts at least one segment of the cuvette array,
  wherein light is irradiated into the light distributor device in temporal succession by a plurality of LED light sources which emit in a spectrally different manner in the UV/VIS/NIR wavelength range, and is distributed among the individual cuvettes, and
  detecting the measurement radiation exiting from the cuvettes by means of at least one photodiode—fixedly assigned to each cuvette—of a stationary detection unit.

The measurement radiation exiting from the cuvettes is converted into an electrical measurement signal and, after being suitably prepared, is displayed in a display unit.

The analyzer may also have an optical measurement unit, which is configured as a unit which is movable along the linear, stationary cuvette array, for example as a spectrometer unit.

A further object of the invention is to improve methods and devices for mixing and/or controlling the temperature of liquid media which are introduced into cuvettes of a cuvette array which are lined up next to one another, such that the length of time from when the liquid media are introduced into the cuvette until a predefined target temperature is reached is shortened, without there being any risk of thermal damage to the sample/reagent mixture. The aim is also to achieve optimal mixing of the sample/reagent mixture when the target temperature is reached.

This object is achieved on the one hand in that the temperature control unit has a cuvette block which is regulated to a predefined target temperature, said cuvette block being equipped with a temperature control device and being in thermal contact with the individual cuvettes, and on the other hand in that stationary mixer units are assigned to the cuvettes in order to mix the samples and reagents, wherein at least one ultrasonic transducer is attached as a stationary mixer unit to each cuvette in order to introduce ultrasonic energy into the cuvettes, and in that the ultrasonic transducer is configured as a piezoelectric vibrator and is connected to a control unit which actuates the at least one ultrasonic transducer as a function of parameter values of the liquid media.

The method according to the invention for mixing and controlling the temperature of liquid media which are introduced into lined-up cuvettes of a cuvette array, wherein the cuvettes of the cuvette array are arranged in a temperature-controllable cuvette block, is characterized by the following steps:
  a) heating the cuvettes to a predefined target temperature with the aid of the temperature-controllable cuvette block,
  b) heating the liquid media with the aid of the temperature-controlled cuvette block in order to reach the predefined target temperature,
  c) in the heating phase according to point b), before the target temperature is reached, additionally introducing a predetermined quantity of ultrasonic energy with the aid of at least one ultrasonic transducer, which is attached to each cuvette, in order to increase the rate of heating, and
  d) simultaneously mixing the liquid media with the aid of the ultrasonic energy introduced in point c).

In particular, it is provided according to the invention that the quantity of ultrasonic energy introduced in point c) is determined as a function of predetermined parameter values, such as for example the type, quantity, viscosity, thermal conductivity and temperature of the added liquid media.

The quantity of ultrasonic energy to be introduced can be determined for example in a test step or calibration step at the factory by experimental measurements and/or calculations, with appropriate information then being made available to the user.

Once the calibration has been completed for all the intended analyte determinations, no measures are required by the user, during operation of the device for mixing and controlling the temperature of liquid media, to determine the required quantity of ultrasonic energy for the respective analyte determination, since it is possible to access the appropriate values from the test and calibration phase.

With the method according to the invention, any local hotspots that occur during rapid heating are effectively prevented since the introduction of ultrasonic energy is regulated by control codes which are stored for example in an analysis protocol and which have been determined as a function of parameter values of the liquid, such that the liquid in the cuvette is heated and is constantly circulated at the same time.

One significant advantage of the invention is therefore that, by parameterizing the quantity of ultrasonic energy introduced, the temperature of the cuvette contents can never be greater than that of the cuvette block, the temperature of which is pre-controlled to a final temperature that is compatible with the sample. As a result, thermal damage to biological samples and reagents due to hotspots or due to a brief exceeding of the target temperature can largely be ruled out.

From a technical standpoint, it is particularly simple and reliable to control the temperature of lined-up cuvettes by means of a cuvette block made of a continuous, thermally conductive material, such as for example a block of anodized aluminum. When heating the cuvette contents from a pre-temperature-controlled heat source, the block temperature $T_{BL}$ is typically approached asymptotically, so that the heating takes place rapidly at first, and then increasingly more slowly. Since the block temperature $T_{BL}$ is never quite reached, in the case of temperature control via a block a slightly lower temperature of $T_{BL-x}$ will be accepted as the target temperature, which is typically in the range of 0.1-0.5° C. below the block temperature when controlling the temperature of biological samples in the context of an optical measurement of particular analytes and may not vary by more than 0.1° C. during the analysis (see FIGS. 17a, 17b).

According to the invention, the ultrasonic energy according to point c) may be introduced into the liquid media in a pulsed manner in multiple boosts.

In addition, it is advantageous if at least one boost of the ultrasonic energy introduced in point c) is optimized with regard to the pulse duration, the frequency and the amplitude for mixing the liquid media in the cuvette.

In this case, a signal waveform which is advantageous for a combined mixing (by generating a convection in the liquid) and heating (by absorbing ultrasound into the liquid) can be selected, starting from a fundamental frequency of the ultrasonic transducer, which may be modulated by an impressed frequency that is lower in comparison (frequency "sweep"). In addition, the amplitude of the fundamental frequency of the ultrasonic transducer may also be modulated by an impressed frequency that is lower in comparison, wherein the amplitude may be varied between a full modulation (100%) of the signal and switch-off of the signal (0%). An amplitude modulation with the amplitude ratio (100:0) would in this case correspond to a burst pattern. In both cases, modulation signal waveforms such as sine, square, sawtooth or the like can be used.

Particularly good results with regard to the mixing of the liquid media introduced into the cuvette can be achieved if the ultrasonic transducer is operated at a fundamental frequency of 200 kHz to 200 MHz, for example at approx. 0.5 MHz to 10 MHz when using a thickness-mode transducer, and at approx. 50 MHz to 150 MHz when using an interdigital transducer.

Preferably, a modulation frequency having an amplitude of 1 to 100 Hz is impressed on the fundamental frequency of the ultrasonic transducer.

For mixing and heating aqueous reagent liquids and sample liquids when carrying out analyses in corresponding cuvettes, the fundamental frequency of ultrasonic transducers which can be used with advantage depends on the type of ultrasonic transducer used. If use is being made of adhesively bonded thickness-mode transducers made of piezoceramic, fundamental frequencies of suitable type (depending on the size and dimension of the substrate) are between approximately 200 kHz and 10 MHz, preferably approximately 0.5 to 10 MHz. If use is being made of adhesively bonded interdigital transducers, fundamental frequencies of suitable type (depending on the size and dimension of the transducer, and also of the substrate) are approximately 10 to 200 MHz, preferably approximately 50-150 MHz The analyzer may also have a mixer unit, for example a pipetting needle which can be set in rotation or in vibration, which can be lowered into the respective cuvettes in order to mix the samples and reagents.

The analyzer has a cuvette washing unit, which according to the invention is configured as a movable machine component which in each washing position has access to one cuvette or to a group of cuvettes simultaneously, preferably to two to five cuvettes arranged next to one another.

According to the invention, the analyzer according to one variant has a temperature control unit for setting a predefinable measurement temperature, which temperature control unit comprises heating foils which thermally contact individual cuvettes or groups of cuvettes and to which different temperature levels can be applied.

A further object of the invention is to propose an analyzer by which, proceeding from the outlined prior art, heterogeneous immunoassays can be carried out, wherein disadvantages, particularly in connection with the sample throughput of known systems, which is limited by processes that are predefined by rigid clock cycles and that take place in predetermined time windows, are avoided and improvements are achieved which increase the sample throughput without significantly increasing the cost of the individual analysis or the analyzer, while at least maintaining the quality of the analysis.

This object is achieved according to the invention in that the analyzer has a device for carrying out heterogeneous immunoassays, which has access to the cuvettes of at least one terminal segment of the stationary, linear cuvette array.

According to the invention, the device for carrying out heterogeneous immunoassays has the following components:

at least one support arm which is movable along the cuvette array and which is lowerable toward the filling opening of a selected cuvette, said support arm having at least one aspirating needle which is lowerable toward the bottom of the cuvette, and also having at least one dispenser, which can be positioned above or in the respective filling opening, for dispensing the liquid media into the cuvette, wherein at least one dispenser is designed to dispense a washing solution for the magnetic particles, at least one magnet assembly for separating the magnetic particles on an inner surface of the cuvette, said magnet assembly being movable along the cuvette array and acting on the contents of the selected cuvette, and at least one optical detection device for receiving a measurement signal that is proportional to an analyte concentration in the selected cuvette, said optical detection device being movable along the cuvette array and being alignable with the measurement window of the selected cuvette.

According to one preferred embodiment variant of the invention, the support arm for the aspirating needle and the at least one dispenser has a lifting and rotating device which is arranged on a platform that is movable along the cuvette array, wherein a common suspension mount for the magnet assembly and the detection device can be arranged on the movable platform.

It is particularly advantageous if the support arm arranged on the movable platform forms, along with the dispenser platform together with the magnet assembly and the detection device, a measurement and manipulation module which is movable along the cuvette array and which combines all the robotic, fluidic and metrological components for the process steps of magnetically separating the beads, so-called B/F washing, and also the triggering and measurement of the luminescence.

A method according to the invention for determining an antigen by means of a heterogeneous immunoassay is characterized in that first, in a first step sequence A,
a sample for determining the antigen,
a suspension of magnetic particles containing a capture antibody, and
optionally a tracer antibody or a labeled antigen are pipetted into a selected cuvette of a stationary cuvette array, and in that the following steps B of an immunochemical analysis, such as
  a) separating the magnetic particles,
  b) introducing and aspirating a washing solution one or more times,
  c) adding a metered quantity of at least one trigger liquid, and
  d) carrying out a luminometric measurement of the sample, take place with the aid of a measurement and manipulation module which is movable along the cuvette array and which is stopped at the selected cuvette in order to carry out some or all of steps a) to d).

One particular advantage of the invention is that, while time-consuming steps for the immunochemical analysis, such as incubation, etc., are being carried out in the selected cuvette, the measurement and manipulation module can be moved to at least one further cuvette of the cuvette array in order to carry out some or all the steps B of an immunochemical analysis.

In particular, the measurement and manipulation module according to the invention can move freely between the cuvettes of the stationary cuvette array in order to carry out a second process step in another cuvette while an assay process step that does not have to be carried out by the components of the measurement and manipulation module is taking place in a first cuvette.

Before the measurement and manipulation module moves to a cuvette, or as it does so, the needle group of the dispensers and also the aspirating needle can be washed in a washing station which is arranged on the measurement and manipulation module.

For example, in one parallelization example, during an incubation step of an assay in a first cuvette, a magnetic separation and B/F washing can be carried out in a second cuvette in order to increase the utilization of the machine components and to save time in carrying out the assays.

According to the invention, the cuvettes which are used in the clinical chemical area of the analyzer have, in a region close to the bottom, inlet and outlet windows which are preferably arranged plane-parallel to one another and which are transparent to the inlet and outlet radiation or measurement radiation of the optical measurement unit.

In the area that is used to carry out heterogeneous immunoassays, wherein the detection takes place via chemiluminescence, the cuvettes of the cuvette arrays require, in a region close to the bottom, only a lateral outlet window which is optically transparent to the luminescent radiation.

BRIEF DESCRIPTION OF THE DRAWINGS

The invention will be explained in greater detail below on the basis of exemplary embodiments, which are partially schematic and in which:

FIG. 6 shows a movable cuvette washing unit of the automatic analyzer according to FIG. 3a, in a three-dimensional view, FIG. 7 shows a needle washing unit of the automatic analyzer according to FIG. 3a, in a three-dimensional, partially cut-away view, FIG. 8 shows a temperature control unit for the cuvettes of the automatic analyzer according to FIG. 3a, in a three-dimensional, partially cut-away view, FIG. 9a shows fluidic elements of a pipetting needle of a pipettor according to FIG. 4, in a schematic illustration, FIG. 9b shows fluidic elements of a needle washing unit according to FIG. 7, in a schematic illustration, and FIG. 9c shows fluidic elements of a cuvette washing unit according to FIG. 6, in a schematic illustration, FIG. 13a shows a second variant of an optical measurement unit according to the invention for obtaining measurement signals from liquid media, in a three-dimensional view of an automatic analyzer according to FIGS. 10a to 10c, FIG. 13b shows an enlarged sectional illustration through the axis of a cuvette, normal to the cuvette array according to FIG. 13a, FIG. 14a shows a third variant of an optical measurement unit according to the invention for obtaining measurement signals from liquid media, in a three-dimensional view of an automatic analyzer according to FIGS. 10a to 10c, FIG. 14b shows an enlarged sectional illustration through the axis of a cuvette, normal to the cuvette array according to FIG. 14a, FIG. 14c shows an enlarged detail illustration from FIG. 14a.

FIG. 21 shows a fluid circuit diagram of the device according to FIG. 19a, and FIG. 22 shows a block diagram regarding the electronic control of the device according to FIG. 19a.

DETAILED DESCRIPTION

Parts which have the same function are provided with the same reference signs in the embodiment variants.

The automatic analyzers and components thereof which are shown in FIGS. 1a to 1c and 2a to 2h relate to examples from the prior art and are described in detail in the introductory part of the description.

Figures 1A, 1B, 1C:
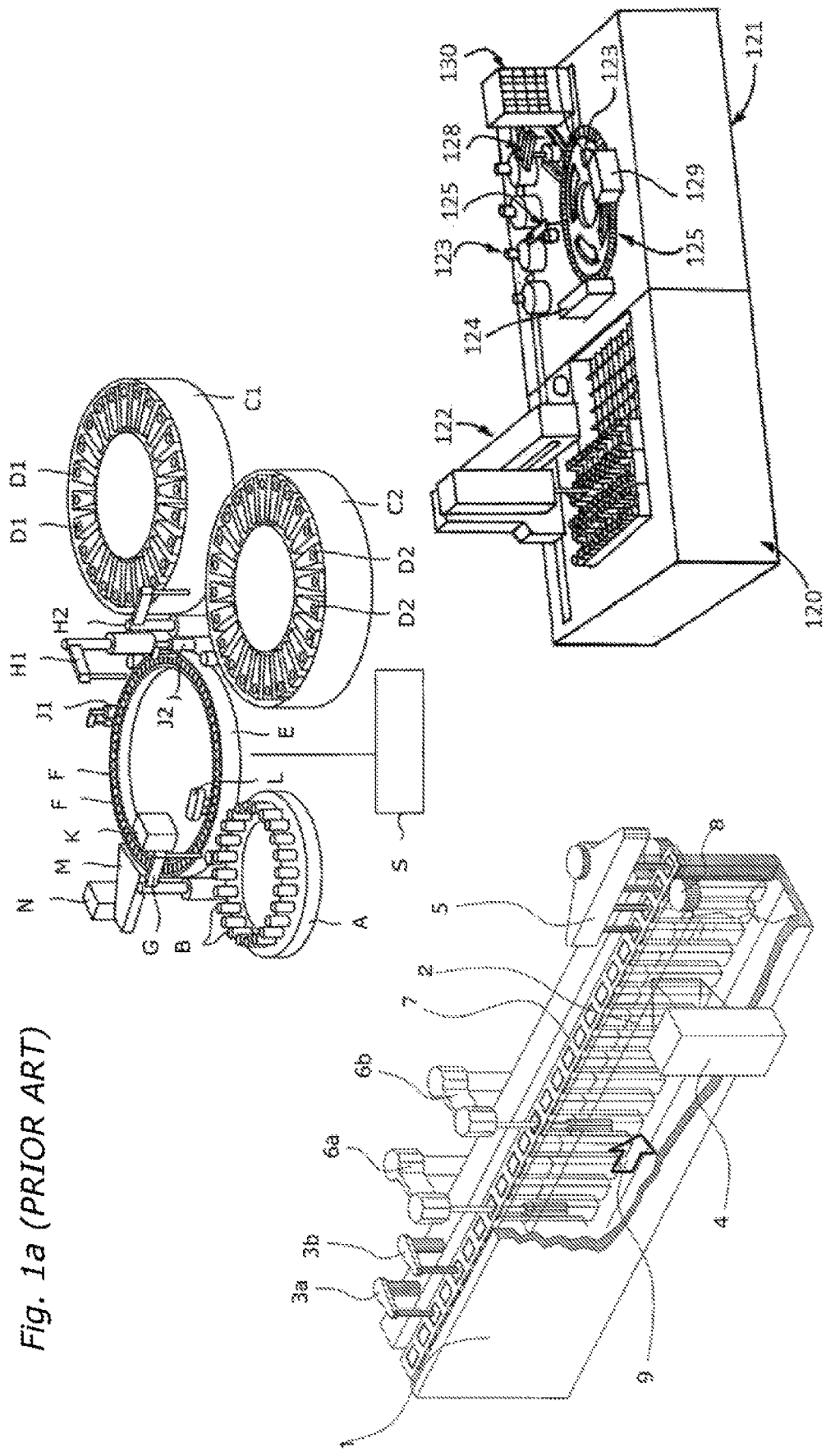
FIG. 1a shows an automatic analyzer having movable reaction vessels or cuvettes arranged in a circular manner on turntables, according to the prior art.
FIG. 1b shows an automatic analyzer having movable reaction vessels or cuvettes arranged in a linear manner, according to the prior art.
FIG. 1c shows an automatic analyzer for clinical chemical analyses and for carrying out heterogeneous immunoassays, according to the prior art.
Figure 2A:
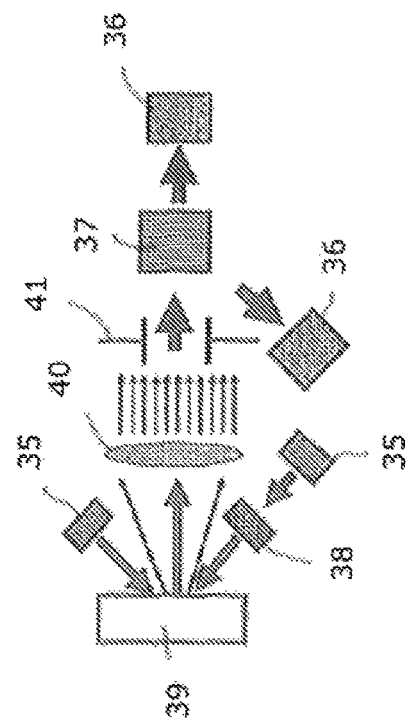
FIG. 2a to FIG. 2d show optical measurement units for obtaining measurement signals from liquid media, according to the prior art.
Figure 2B:
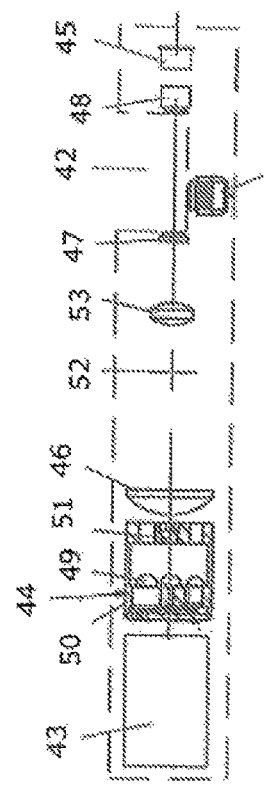
Figure 2D:
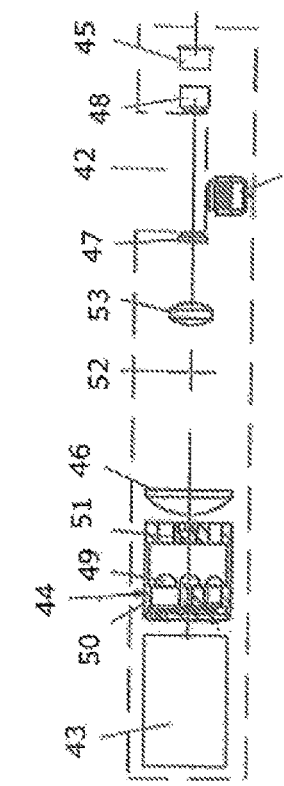
Figure 2C:
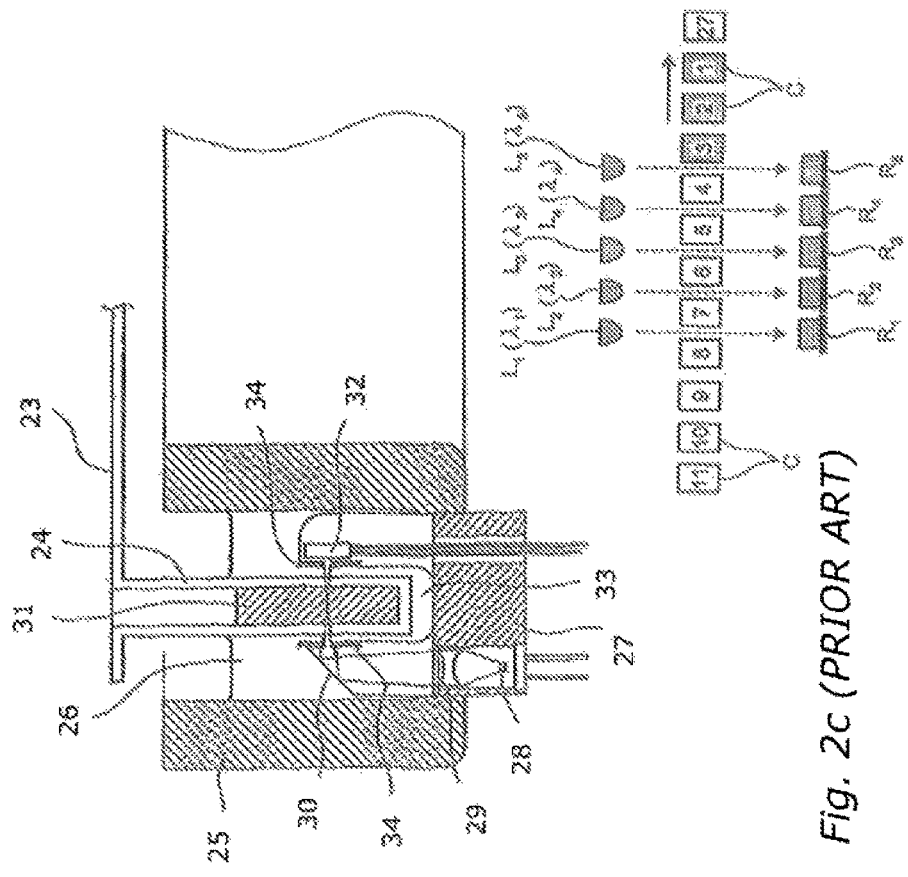
Figure 2F:
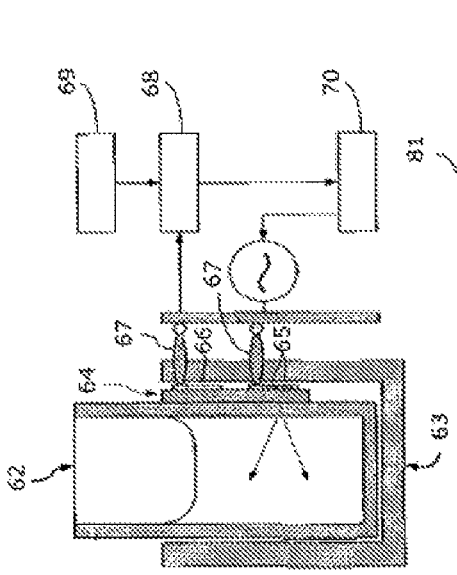
FIG. 2e to FIG. 2h show devices for mixing and stirring liquids in cuvettes, according to the prior art.
Figure 2H:
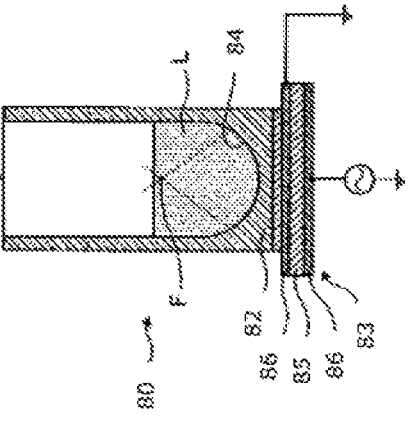
Figure 2E:
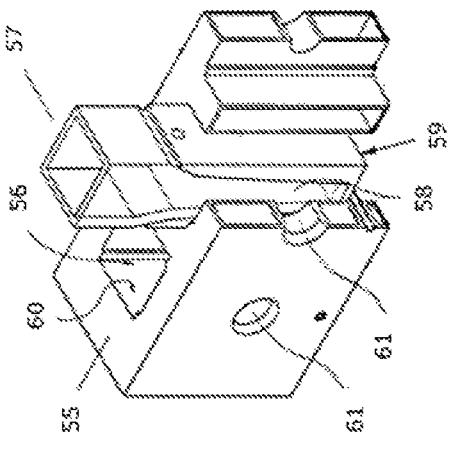
Figure 2G:
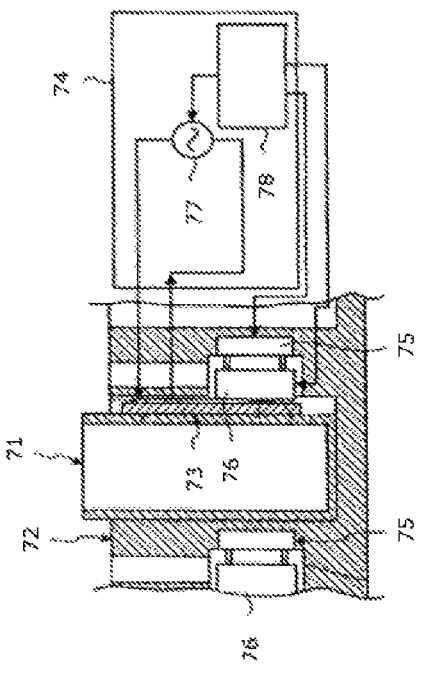
Figure 3A:
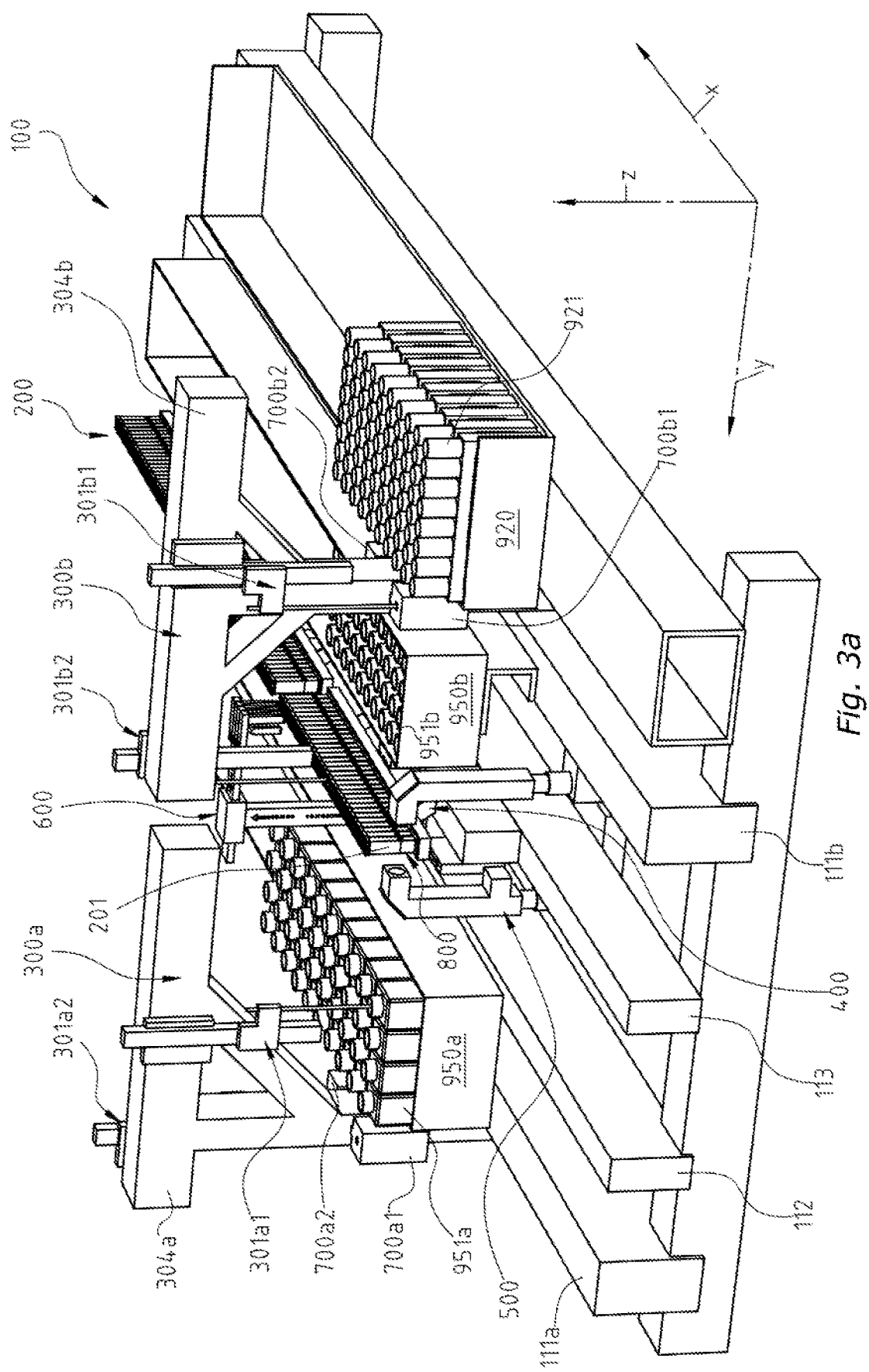
FIG. 3a shows a first embodiment variant of an automatic analyzer according to the invention for carrying out chemical, biochemical and/or immunochemical analyses of liquid samples, having a linear, stationary cuvette array, in a three-dimensional overall view.
Figure 3B:
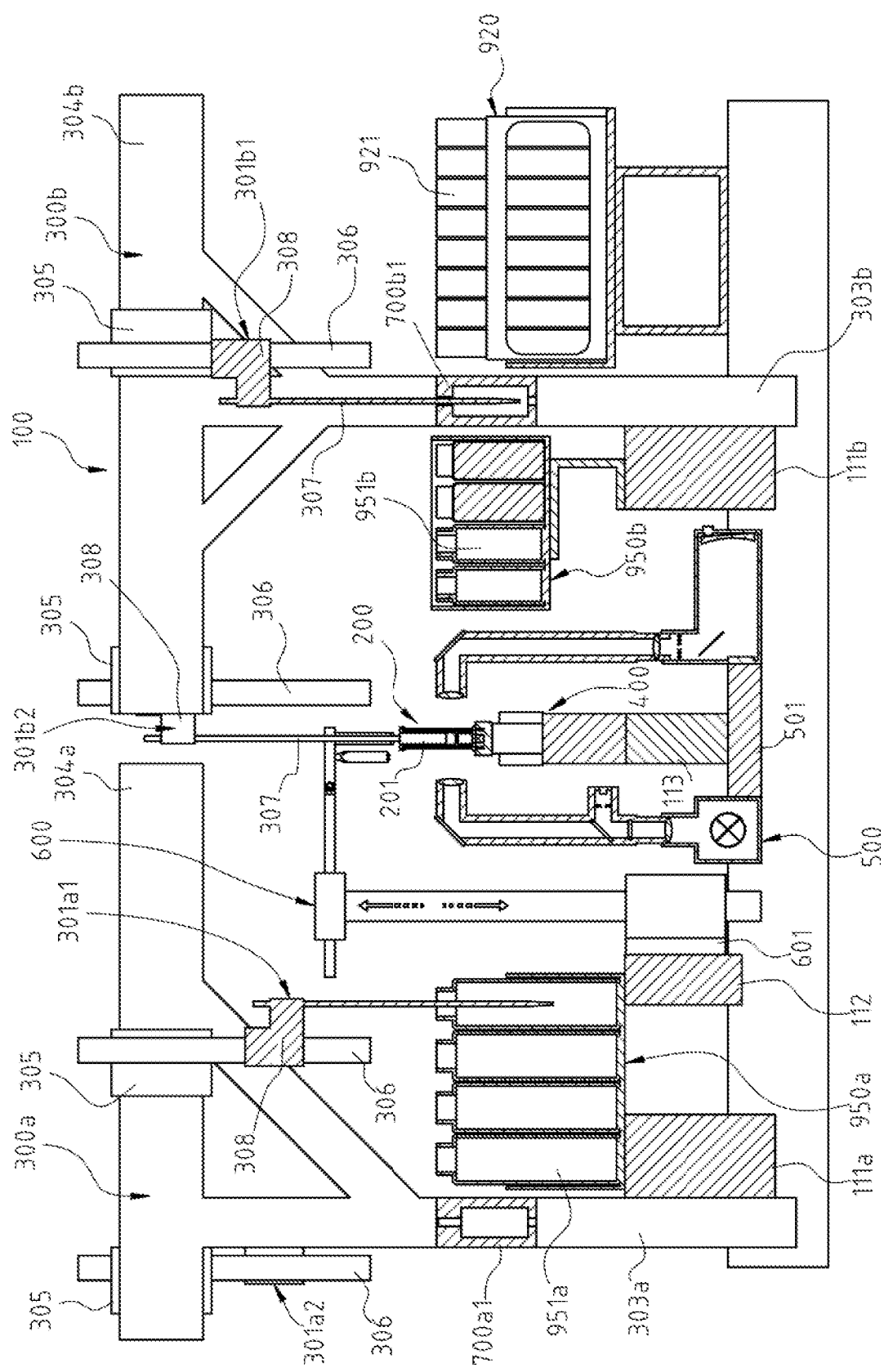
FIG. 3b shows a sectional illustration of the analyzer along the line IV-IV in FIG. 3c.
Figure 3C:
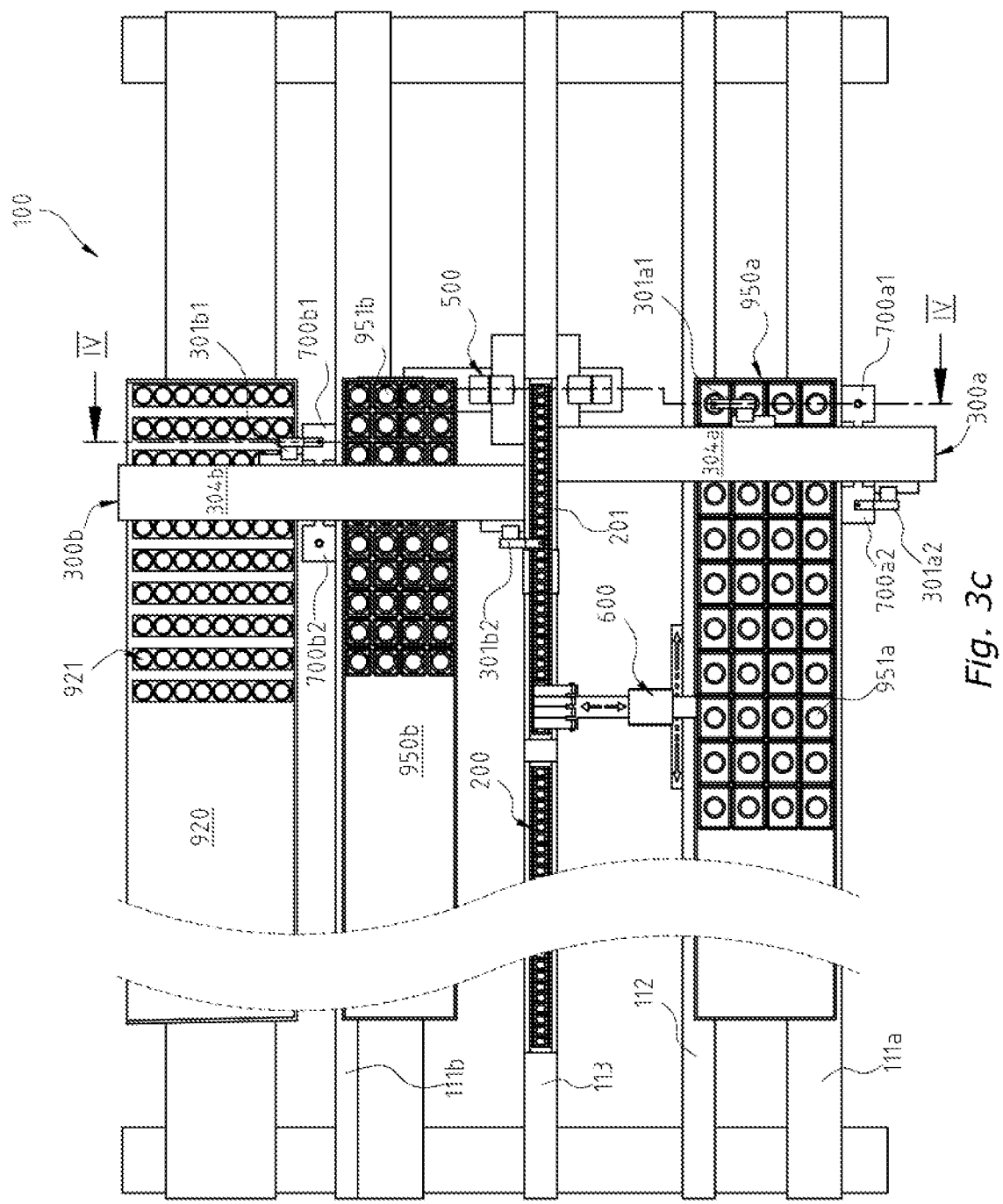
FIG. 3c shows a simplified plan view of the analyzer according to FIG. 3a, FIG. 4 shows two independently movable pipettors of the automatic analyzer according to FIG. 3a, in a three-dimensional view.

The automatic analyzer 100 of a first embodiment variant, which is shown in FIGS. 3a to 3c, serves to carry out chemical, biochemical and/or immunochemical analyses of liquid samples. For the sake of simplicity, only those components of the analyzer 100 which are essential to the present invention are shown, wherein analyzer components such as pumps, valves, evaluation units, control units and drive units will not be discussed in detail.

The liquid samples are present in sample vessels 921 in a sample store 920 of the analyzer 100 and are analyzed with the aid of liquid reagents which are present in reagent vessels 951a, 951b in two reagent stores 950a, 950b of the analyzer 100.

The cuvettes 201 for receiving the liquid samples and reagents are arranged in the form of a stationary, linear cuvette array 200 in the analyzer 100 and remain at their original position during a plurality of individual analyses. In the illustrated example, the cuvette array 200 is arranged between the first reagent store 950a and the second reagent store 950b.

Figure 5:
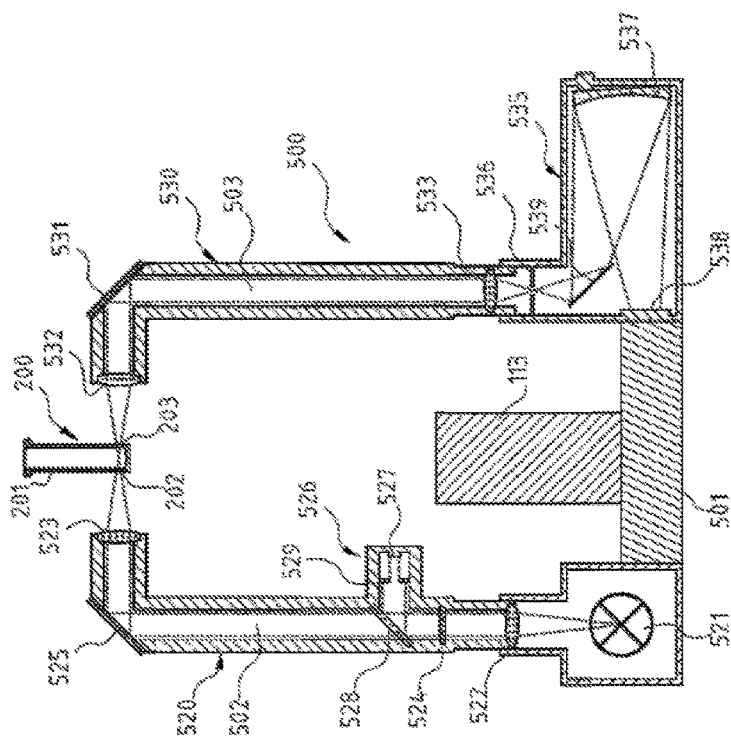
FIG. 5 shows a movable optical measurement unit of the automatic analyzer according to FIG. 3a, in a sectional illustration.

The automatic analyzer 100 is equipped with movable and stationary machine components, namely:
  with two pipettors 300a, 300b which are movable in the x-direction along a line of movement defined by the linear cuvette array 200, each of said pipettors being equipped with two pipetting needles 301a1, 301a2 and 301b1, 301b2 which are designed to be lowerable in the z-direction into the cuvettes 201, into the sample vessels 921 located in the sample store 920 and into the reagent vessels 951a, 951b located in the reagent stores 950a, 950b and which are designed to be movable in a y-direction, substantially normal to the x-direction, between the cuvettes 201 and the sample store 920 and/or the two reagent stores 950a, 950b;
  with a mixer unit 400 for mixing the samples and reagents in the cuvettes 201;

with an optical measurement unit 500 which, in order to obtain a measurement signal, receives measurement radiation that exits through a measurement window 202, 203 arranged on the side of the cuvette 201 (see FIG. 5);

with a cuvette washing unit 600 for cleaning the cuvettes 201, which cuvette washing unit is movable in the x-direction along the line of movement defined by the cuvette array 200;

with needle washing units 700a1, 700a2, 700b1, 700b2 for cleaning the pipetting needles 301a1, 301a2, 301b1, 301b2 of the two pipettors 300a, 300b; and with a stationary temperature control unit 80 for setting a predefinable measurement temperature in the cuvettes 201.

The pipettors 300a, 300b are attached by means of movable mounting elements (not shown) to the rails 11a, 111b, which are arranged in a parallel manner; in addition, a corresponding rail 113 together with a movable mount 501 is provided for the optical measurement unit 500, and a rail 112 together with a movable mount 601 is provided for the cuvette washing unit 600. The movable mounts of the pipettors 300a, 300b and the mounts 501 and 601 are driven for example by means of toothed belts (not further shown here) and stepper motors at one end of the rails 112, 113, 111a and 111b.

As can be seen in particular in FIG. 3b, at least two—in the illustrated example several—of the machine components are designed to be movable in the x-direction independently of one another along or parallel to the line of movement defined by the linear cuvette array 200, and can each access different cuvettes 201 or groups of cuvettes 201 in a freely selectable order.

In the embodiment variant shown in FIGS. 3a to 3c, the analyzer 100 has a sample store 920, a first reagent store 950a and a second reagent store 950b. The storage areas may be cooled entirely or in part.

In order to charge the analyzer 100 with sample material, vessels 921 containing analysis samples are introduced manually or by means of robotics into the sample store 920 at predetermined positions. The analyses desired for the individual analysis samples are input into the controller of the analyzer 100.

In order to charge the analyzer with reagents, reagent vessels 951a, 951b containing reagents for analyzing different analytes are introduced manually or by means of robotics into the two reagent stores 950a, 950b of the analyzer 100 at predetermined positions.

Vessels containing calibration liquids and comparative samples may also be introduced into the sample store and/or reagent store.

In the embodiment variant shown, the analyzer has two pipettors 300a, 300b which are movable in the x-direction independently of one another and which—with the exception of the same cuvette—can access individual cuvettes 201 of the cuvette array 200 entirely independently of one another and in a freely selectable order.

Figure 4:
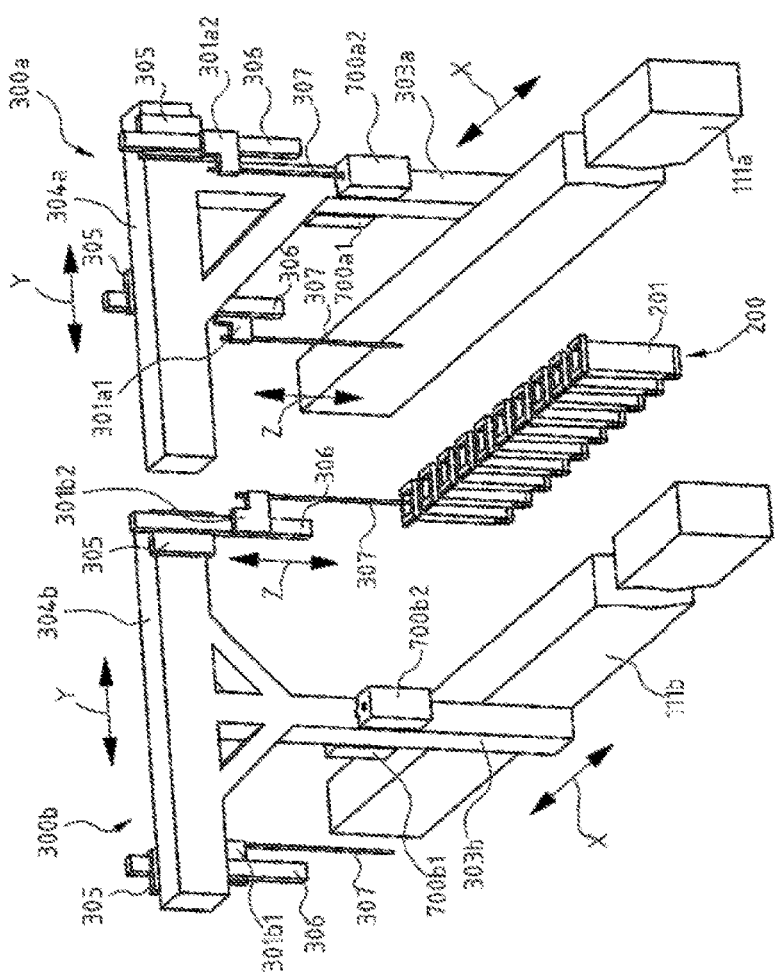

The two pipettors 300a, 300b shown in FIG. 4 each have a vertical tower 303a, 303b and also an arm 304a, 304b which is oriented horizontally in the y-direction, so that a substantially L-shaped support structure (pipettor 300a) for the two pipetting needles 301a1, 301a2 or T-shaped support structure (pipettor 300b) for the two pipetting needles 301b1, 301b2 is formed, said support structure being movable in the x-direction along the rail 111a or 111b. Each pipettor thus has two pipetting needles 301a1, 301a2 and 301b1, 301b2, which are movable in the y-direction independently of one another and parallel to one another, along with associated cannulas or hollow needles 307. The pipetting needles 301a1, 301a2 and 301b1, 301b2 are attached to the left and to the right of the arm 304a and 304b by means of a mount 305 which is movable in the y-direction, and thus can move past one another unhindered. Each mount 305 has a downwardly projecting rail portion 306, on which the needle can be lowered in the z-direction into the cuvettes 201 of the cuvette array 200.

The individual pipetting needles 301a1, 301a2 and 301b1, 301b2 each have a needle holder 308 with a region which projects in the direction of the cuvette array 200 and which carries the hollow needle 307. As a result, even when the hollow needle 307 of the pipetting needle 301b2 is oriented or lowered in alignment with the cuvette 201, sufficient space remains for the L-shaped pipettor 300a to be able to move past the T-shaped pipettor 300b (see FIG. 3b).

In the example shown, the pipettor 300b or the two pipetting needles 301b1, 301b2 thereof can thus access only the sample vessels 921 in the sample store 920 and the reagent vessels 951b in the reagent store 950b, whereas the pipettor 300a or the pipetting needles 301a1, 301a2 thereof only has access to the reagent vessels 951a arranged in the reagent store 950a. All the pipetting needles 301a1, 301a2 and 301b, 301b2 can be moved as far as the plane of the cuvette array 200 and can be lowered into the individual cuvettes 201.

A significant increase in the sample throughput can be achieved due to the fact that the needle washing units 700a1, 700a2 and 700b1, 700b2 are arranged on the pipettor 300a and 300b and are designed to be movable therewith. In the embodiment variant shown, each pipetting needle 301a1, 301a2, 301b1, 301b2 has its own needle washing unit 700a1, 700a2, 700b1, 700b2, which may in each case be arranged for example on the vertical tower 303a and 303b of the pipettor 300a and 300b. Therefore, in each case one of the pipetting needles 301a1 or 301b1 can be washed in the associated needle washing unit 700a1 or 700b1 while the respective other pipetting needle 301a2, 301b2 is immersed in a cuvette 201 (see FIG. 4).

Simple embodiment variants of the analyzer are also conceivable, which have only one pipettor. The latter may be configured either as an L-shaped pipettor 300a which is movable at the side of a sample store or reagent store and may have just one movable pipetting needle 301a1, or else may have a T-shaped support structure and be designed to be movable between a sample store and a reagent store.

The optical measurement unit 500 shown in FIG. 5 is configured as a unit which is movable along the linear, stationary cuvette array 200 on the rail 113 by means of the mount 501. In the example shown in FIG. 5, said unit consists of a light-supplying unit 520 on one side of the cuvette array 200 and of a spectroscopic unit 530 on the other side, these being rigidly connected to one another via the mount 501. The optical measurement unit 500 comprises a light source 521, for example a halogen lamp, a respective beam path for the inlet radiation 502 and the outlet radiation or measurement radiation 503 with lenses 522, 523, 532, 533, filters 524, deflecting mirrors 525, 531, and a spectrometer 535 which detects the spectrum of the measurement radiation and/or the intensity of the measurement radiation at individual predetermined wavelengths in the range from 300 to 800 nm. In the example shown in FIG. 5, the spectrometer 535 consists of a polychromator comprising an entrance slit 536, a deflecting mirror 539, and a concave diffraction grating 537 which projects the spectrum of the measurement radiation 503 onto a sensor array 538, for example a photodiode array. In the example shown, the liquid located in the cuvette 201 is measured using transmitted light, wherein the inlet radiation 502 enters the cuvette 201 through a side inlet window 202 and exits from the cuvette 201 through an opposite outlet window 203.

Preferably, the optical measurement unit 500 comprises a reference detector 526 for the purpose of measuring and compensating fluctuations in the intensity of the light emitted by the light source 521. This consists for example of a beam splitter 528, which is located in the beam path for the inlet radiation 502, a diaphragm 529 and a photodetector 527, for example a photodiode.

With the optical measurement unit 500 described above, various optical measurements can be carried out at single and/or multiple wavelengths in the wavelength range of ultraviolet and visible light. Examples of these are photometric, turbidimetric and luminometric measurements.

An optical measurement process based on the example of a photometric measurement will be described below. The inlet radiation 502 originating from the polychromatic light source 521 passes through the reaction mixture located in the cuvette 201, said reaction mixture consisting of the sample and the reagents added for the respective analysis, enters the spectroscopic unit 530 as measurement radiation 503, and in the spectrometer 535 is split in terms of wavelengths at the diffraction grating 537 and is received by the sensor array 538. The individual light-receiving elements of the sensor array 538 of the spectrometer 535, for example photodiodes, and also the reference photodiode 527 of the reference detector 526 output a photocurrent corresponding to their respective measurement wavelength, which photocurrent is converted by a signal processing circuit and by means of AD converters into a digital measured value. In an operating unit, depending on the respective analysis, individual digital measured values or digital measured values that have been measured periodically over time and at one or more wavelengths are calculated with previously known reference values and calibration values assigned to the respective analysis in order to give a concentration value for the analyte.

In order to mix the samples and reagents, a stationary mixer unit 400 (not shown in detail here) is assigned to the cuvette array 200 as a whole, preferably to individual groups or segments 210 of cuvettes 201. The cuvette washing unit 600 shown in FIG. 6 is designed to be movable in the x-direction along the rail 112 (see FIG. 3b) via a mount 601. The head 602 of the unit 600 can be moved up and down in the z-direction by means of a vertically oriented rail portion 603, which is guided in the mount 601, in order to introduce either the washing elements 610 or the drying plungers 620 into the cuvettes 201 of the cuvette array 200. By way of an adjusting element 604, which is guided in the head 602 and carries for example four drying plungers 620 and also washing elements 610, a changeover from the washing position to the drying position can take place by a displacement in the y-direction. Individual fingers 605, which carry the washing elements 610 and the drying plungers 620, can be pivoted upward—as indicated by the arrow 691—so that only one or a few cuvettes 201 are washed simultaneously.

FIG. 7 shows, in an enlarged sectional illustration, the structure of a needle washing unit which is denoted by the general reference sign 700 and which corresponds to the substantially identically constructed needle washing units 700a1, 700a2, 700b1, 700b2 shown at different positions in FIGS. 3a to 3c and 4, and a pipetting needle which is denoted by the general reference sign 301 and which corresponds to the substantially identically constructed pipetting needles 301a1, 301a2, 301b1, 301b2 shown at different positions in FIGS. 3a to 3c and 4. The hollow needle 307 of the pipetting needle 301 is introduced through a receiving opening 711 in the housing 710 of a needle washing unit 700, wherein simultaneously the lumen of the hollow needle 307 can be cleaned with a system liquid 712 and the outer side of the needle can be cleaned with a rinsing liquid 714 which is supplied from an annular chamber 715 via lateral cleaning nozzles 713. In order to clean the inside and the outside of the hollow needle 307 by repeatedly aspirating and discharging washing solution from the lower part of the needle washing unit 700, washing solution may be supplied through a radial inlet 716 and can then be emptied through an extraction opening 717.

FIG. 8 shows an enlarged detail of the linear cuvette array 200 of the analyzer 100 with the partially cut-away housing 892 and a cuvette 201 arranged therein, said cuvette being contacted by a heating foil 891 of a temperature control unit 800 in order to set a predefinable measurement temperature; the electrical contact pins 893 of said temperature control unit emerge from the housing 892. Further electrical contact pins 894 may be provided for contacting a temperature sensor. The cuvette 201 has measurement windows on the side, in the illustrated example inlet and outlet windows 202, 203 (outlet window not visible), which are arranged in a region close to the bottom and are preferably arranged plane-parallel to one another, said measurement windows being transparent to the inlet radiation and the outlet radiation or measurement radiation of the optical measurement unit 500. In the region of the inlet and outlet windows 202, 203 of the cuvette 201, the housing 892 has corresponding openings 895. The individual contact pins 893, 894 latch into corresponding contact openings. Latching elements 896 which serve to attach the cuvette array 200 are formed at the bottom of the housing 892.

FIG. 9a shows the fluidic circuit diagram of a pipetting needle 301, the hollow needle 307 of which is connected, via a pressure transfer channel 712 which is filled with a degassed liquid, to a precision piston pump 325, preferably a positive displacement pump (diluter) which is driven by a stepper motor. The positive displacement pump has on the side an additional liquid connection which is connected via a solenoid valve 326 to a supply unit 320 for a system liquid, which conveys for example degassed, deionized water via a rinsing pump 321 from a storage vessel 322, which can be refilled or pressurized via a solenoid valve 323.

In order to detect faults, the pressure transfer channel 712 has, in the vicinity of the pipetting needle 301, a further connection to a pressure sensor 324, which is connected to an evaluation and control unit (not shown here), for example in order to detect blockages of the hollow needle 307.

Description of a Pipetting Process

In order to transfer a defined quantity of liquid using the pipetting needle 301, the latter is first moved in the horizontal direction to a first vessel, 5 µl of air (spacer) is aspirated into the tip of the hollow needle 307, and the pipetting needle 301 is lowered in the direction of the liquid surface of the first vessel. In order to ensure a sufficient, but not excessive, depth of immersion of the pipetting needle 301, the downward movement of the hollow needle 307 is stopped at a defined depth of immersion by a signal from a liquid surface detection device (not shown), for example using a capacitive detection principle. In order to aspirate a defined quantity of liquid with high accuracy in the µl range, a negative pressure is then generated in the hollow needle 307 of the pipetting needle 301 by moving the working piston of the positive displacement pump (diluter) shown in FIG. 9a in the downward direction, which causes a corresponding volume of liquid to be aspirated from a first vessel. The pipetting needle 301 is then moved together with the aspirated liquid, which is separated from the system liquid by a separating air bubble (spacer), to a second vessel, wherein the process then takes place in reverse and the aspirated liquid is dispensed through the tip of the hollow needle 307 into the second vessel. At least between two pipetting processes involving different liquids to be pipetted, an internal and external cleaning of the pipetting needle 301 always takes place in a needle washing unit 700 (see FIG. 7).

FIG. 9b shows the fluidic circuit diagram of a needle washing unit 700 according to FIG. 7, with the hollow needle 307 of the pipetting needle 301 lowered therein. The housing 710 of the needle washing unit has in the upper region a concentrically extending annular chamber 715, which acts as a media supply for a plurality of inner, concentrically oriented cleaning nozzles 713 and which is connected via respective solenoid valves to a supply unit 719 for a rinsing liquid (for example deionized water) and a supply unit 727 for dry air.

An inlet 716 arranged radially at mid-height of the housing 710 of the needle washing unit 700 is likewise connected to a solenoid valve and serves solely for supplying surfactant-containing washing solution from a supply unit 723.

The supply units 719 for a rinsing liquid and 723 for a washing solution each have a pump 720, 724 which conveys a surfactant-containing washing solution or a rinsing liquid from the respective storage containers 721, 725, which can each be refilled or pressurized via a solenoid valve 722, 726. The supply unit 727 for air has an air pump 728 for supplying compressed air and optionally a drying means (not shown).

The extraction opening 717 located at the bottom of the needle washing unit 700 is connected via a solenoid valve 718 to the wastewater collection unit 729, which is under a vacuum and substantially consists of a collecting container 730 which has in the gas space above the liquid a connection to a vacuum pump 731, which is connected to the collecting container 730 via a solenoid valve. The wastewater collected can be discharged via a solenoid valve 732 at the bottom of the collecting container 730 and can be fed to a further wastewater treatment.

Description of a Needle Washing Process

In a typical process for washing the pipetting needle 301, the latter is first moved horizontally to the needle washing unit 700 and is lowered into the lower holding position of the washing chamber. All the wastewater that is produced when cleaning the pipetting needle 301 is sucked away via the extraction opening 717 located at the bottom, is collected, and is optionally subjected to an aftertreatment. Residual amounts of the last-pipetted liquid which are located in and on the needle tip are then emptied and sucked away via the precision piston pump 325 of the pipetting needle 301, which is shown in FIG. 9a. Finally, the lowered pipetting needle 301 is rinsed from behind by means of the supply unit 320 for system liquid, which is shown in FIG. 9a.

In a next step (with the solenoid valve 718 at the extraction opening 717 closed), a defined volume of surfactant-containing washing solution is introduced through the inlet 716 in the housing 710 of the needle washing unit 700, as a result of which the chamber in the lower part fills with a defined level of washing solution. The hollow needle 307 of the pipetting needle 301 is lowered so far until an external wetting of the needle can take place by immersion in the washing solution and an internal wetting of the hollow needle 307 can take place as a result of the washing solution being aspirated into the needle interior. The aspirated washing solution is then discharged again, it being possible for the process of aspirating and discharging the washing solution to be repeated multiple times in order to improve the cleaning effect.

In a last step, the contaminated washing solution is sucked away and the interior of the hollow needle 307 is rinsed with system liquid (for example degassed, deionized water), while the outer side of the hollow needle 307 is at the same time rinsed with rinsing liquid from the supply unit 719 by the concentrically arranged cleaning nozzles 713 located at the top, the tip of the hollow needle 307 being moved upward from the bottom in order to improve the cleaning effect.

Once the simultaneous rinsing of the inside and the outside is complete, the hollow needle 307 is moved back into the lower holding position, the media supply to the cleaning nozzles 713 is switched to the supply unit 727 for compressed air, and the tip of the hollow needle 307 again moves upward from the bottom, as a result of which adhering water droplets can quickly be removed from the needle surface. The pipetting needle 301 can then be moved out of the needle washing unit 700 and, after aspirating a separating air spacer (5 µl), is again ready for pipetting.

FIG. 9c shows the fluidic circuit diagram and the longitudinal section of a finger 605 of the cuvette washing station 600 which is articulated to the adjusting element 604, together with a washing element 610 and a drying plunger 620 (see also FIG. 6), it being possible for the descriptions of the supply units 630 (rinsing liquid), 634 (washing solution) and 638 (air) and also of the wastewater collection unit 640 to be taken from the supply units 719 (rinsing liquid), 723 (washing solution), 727 (air) and 729 (wastewater) in the description of the figures relating to FIG. 9b, which are functionally identical and/or structurally identical to the units shown in FIG. 9c.

The washing element 610 and also the drying plunger 620 of the finger 605 of the cuvette washing station 600 can be lowered one after the other, by horizontal and vertical translational movements, into the cuvette 201 to be washed of a linear cuvette array, wherein, after being lowered into the cuvette 201, in each case a circumferential gap of less than 1 mm remains free between the inner side of the cuvette 201 and the washing element or drying plunger, in order to enable a controlled flow of the cleaning media along the inner cuvette wall.

The washing element 610 has, at its upper end, an elastomer seal 611 which prevents any escape of cleaning media between the upper cuvette rim and the underside of the finger 605 during the washing process. Around the shaft of the riser channel 612, which extends in the middle of the washing element 610 and is designed to suck away the wastewater and waste air, there is an annular media supply which makes it possible to rinse the inner side of the cuvette from top to bottom (see arrows). Via suitable solenoid valves, the washing element 610 can be charged with surfactant-containing washing solution from the supply unit 634, with rinsing liquid (for example deionized water) from the supply unit 630, or with compressed air from the supply unit 638, these being discharged via the vacuum-operated wastewater collection unit 640 by being supplied to the vacuum-operated wastewater collection unit 640 via a solenoid valve. The wastewater collection unit 640 substantially consists of a collecting container 730 which has, in the gas space above the liquid, a connection to a vacuum pump 642, the latter being connected to the collecting container 641 via a solenoid valve. The wastewater collected can be discharged via a solenoid valve 643 at the bottom of the collecting container 641 and can be fed to a further wastewater treatment.

The drying plunger 620 is made of a porous, air-permeable material and has in the interior a longitudinal channel 621 which does not extend quite as far as the bottom and which serves to supply and distribute the compressed air through the wall of the porous drying plunger 620 into the cuvette 201. The drying plunger 620 does not adjoin the underside of the finger 605 with a seal, but rather projects somewhat in the lowered state and forms a circumferential air outlet gap (see horizontal arrows) between the top of the cuvette 201 and the underside of the finger. The drying plunger 620 may be connected via a solenoid valve to compressed air from the supply unit 638.

Description of a Cuvette Washing Process

In a step preparing for the actual cleaning, the washing element 610 is lowered into the cuvette 201 to be washed, and the reagent/sample mixture located in the cuvette 201 after the analysis is sucked away via the central riser channel 612 and is fed to the wastewater collection unit 640.

In a first cleaning step, flushing takes place using washing solution from the supply unit 634, rinsing liquid from the supply unit 630 and finally compressed air from the supply unit 638, it being possible for this cleaning sequence using said media to be repeated multiple times in order to improve the cleaning effect.

The washing element 610 is then lifted out of the washed cuvette 201, which nevertheless contains residual moisture, and the finger is moved in the y-direction.

In a second cleaning step, the drying plunger 620 is then lowered in the z-direction into the cuvette 201 and air is blown along the inner side of the cuvette for a certain period of time using dry compressed air from the supply unit 638, wherein the air required for this exits uniformly from the porous body of the drying plunger 620, sweeps along the inner side of the cuvette 201 from bottom to top, and exits at the shank of the drying plunger 620.

Examples

The automatic analyzer shown in FIGS. 3a to 3c operates for example as follows:

Prior to an analysis, that is to say prior to determining an analyte $A_x$ of an analysis sample $P_x$, the control unit of the analyzer brings together, from the known and previously input information, all the data required for analyzing the analyte A; (analysis protocol, positions of the vessels 921, 951a, 951b containing the analysis sample and containing the reagents required for the analysis, position of a free cuvette 201 in the cuvette array 200, cuvette temperature, choice of measurement procedure, calibration data, measurement and evaluation algorithms).

Example: Single Analysis

Phase 1

At the start of and during the analysis, the temperature of the cuvette 201 provided for the analysis is controlled to a predetermined temperature by means of the temperature control unit 800 assigned to the cuvette 201.

A predetermined quantity of a first analysis sample is taken up from a first sample vessel 921 in the sample store 920 by the first pipetting needle 301b1 of the T-shaped pipettor 300b, and a predetermined quantity is dispensed by the latter into a free cuvette 201. After the pipetting process, the pipetting needle 301b1 is washed in the first needle washing unit 700b1 of the pipettor 300b and is made available.

Phase 2

A predetermined quantity of a first reagent liquid is taken up from a first reagent vessel 951a in the reagent store 950a by a pipetting needle 301a1 of the L-shaped pipettor 300a, and a predetermined quantity is pipetted into the cuvette 201. The two liquids in the cuvette are then mixed by switching on the mixer unit 400 assigned to the cuvette for a short period of time (a few seconds). After the pipetting process, the pipetting needle 301a1 is washed in a first needle washing unit 700a1 of the L-shaped pipettor 300a and is made available.

Phase 3

Depending on the respective analysis protocol, a predetermined quantity of a second reagent liquid is taken up from a reagent vessel 951b in the reagent store 950b by the second pipetting needle 301b2 of the T-shaped pipettor 300b, and a predetermined quantity is dispensed by the latter into the cuvette 201. The contents of the cuvette are then mixed by switching on the mixer unit 400 assigned to the cuvette 201 for a short period of time (a few seconds). After the pipetting process, the pipetting needle 301b2 is washed in the second needle washing unit 700b2 of the T-shaped pipettor 300b and is made available.

Phase 4

Phase 4 begins with the photometric measurements on the cuvette 201, usually after completion of phase 2.

The optical measurement unit 500 periodically travels along the linear cuvette array 200 and, as it moves past ("on the fly"), generates a measured value at the inlet window 202 or outlet window 203 of the cuvette 201—if this is provided by the measurement protocol at the respective time of moving past. As an alternative to this, the optical measurement unit 500 may also stop briefly as it moves past and may carry out a measurement while it is stopped, in order to obtain a more accurate measured value.

While the chemical reaction takes place in the cuvette 201 between the sample and the reagent, measurement points can be generated at defined time intervals. Depending on the respective analysis protocol, singular or—in the case of kinetic measurements—time-dependent measured values at one or more wavelengths are obtained, and are calculated and displayed with previously known reference values and calibration values assigned to the respective analysis, in order to give a concentration value of the analyte.

Depending on the type of the respective analysis and sample, the measurement process—particularly in the case of kinetic measurements—may extend over very different lengths of time, from a few seconds to the double-digit minute range.

Immediately after completion of the photometric measurement, the cuvette 201 is released in order to be washed by the cuvette washing unit 600. The washing process by means of the cuvette washing unit 600 takes place immediately after the cuvette has been released, preferably together with a plurality of adjacent cuvettes 201 which have likewise been released for washing, and after the movable cuvette washing unit 600 has "become free". After washing and drying, the cuvette 201 is made available for the next analysis.

Example: Multiple Analyses

Prior to carrying out multiple analyses, the sample store 920 is manually or automatically charged with the samples $P_1$ to $P_n$. The type and number of analyses $A_1$ to $A_n$ to be carried out for each sample $P_x$ is input into the controller of the analyzer 100. The reagent stores 950a, 950b are optionally charged or replenished with the reagents required for the analyses to be carried out.

For each analysis $P_xA_x$ to be carried out, the above-described phases 1 to 4 are carried out, in each case starting with phase 1.

Once the pipettor 300b in phases 1 and 3 has been claimed by the analysis $P_xA_x$ to be carried out, phase 1 of the subsequent analyses $P_xA_{x+1}$ or $P_{x+1}A_x$ can begin only when the analysis that is taking place has completed phase 1 and is outside of phase 2, namely for as many subsequent analyses as there are "free" cuvettes, that is to say cuvettes which have not been claimed by other analysis processes.

In contrast to the systems described in the introduction, the concept according to the invention makes it possible that, once a measurement is complete, a cuvette can immediately be washed and made available for a new test, without this disadvantageously interfering with the procedures of the analysis processes that are still ongoing.

Figure 10A:
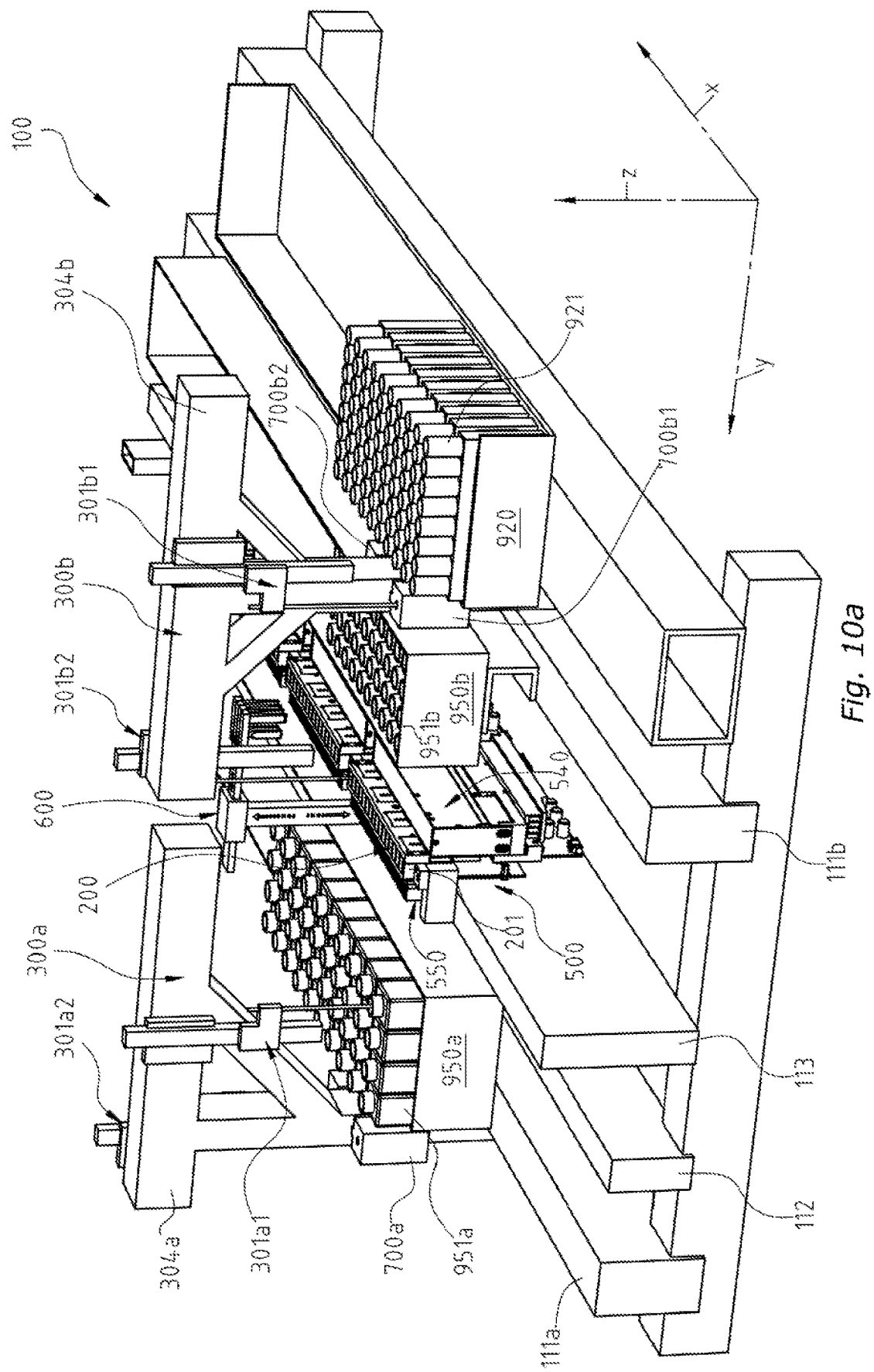
FIG. 10a shows a second embodiment variant of an automatic analyzer according to the invention for carrying out chemical, biochemical and/or immunochemical analyses of liquid samples, having a linear, stationary cuvette array, in a three-dimensional overall view.
Figure 10B:
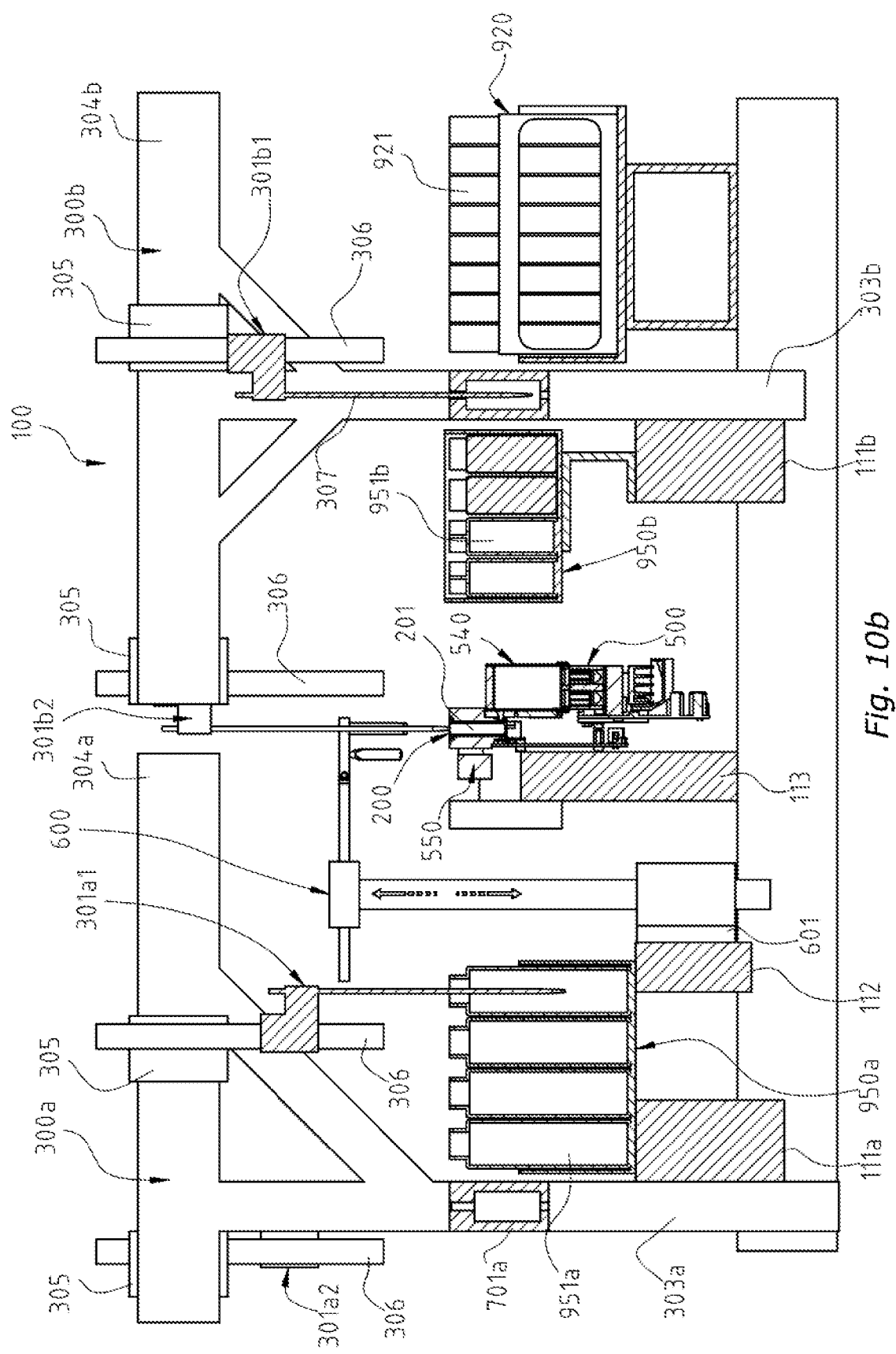
FIG. 10b shows a sectional illustration of the analyzer along the line IV-IV in FIG. 10c.
Figure 10C:
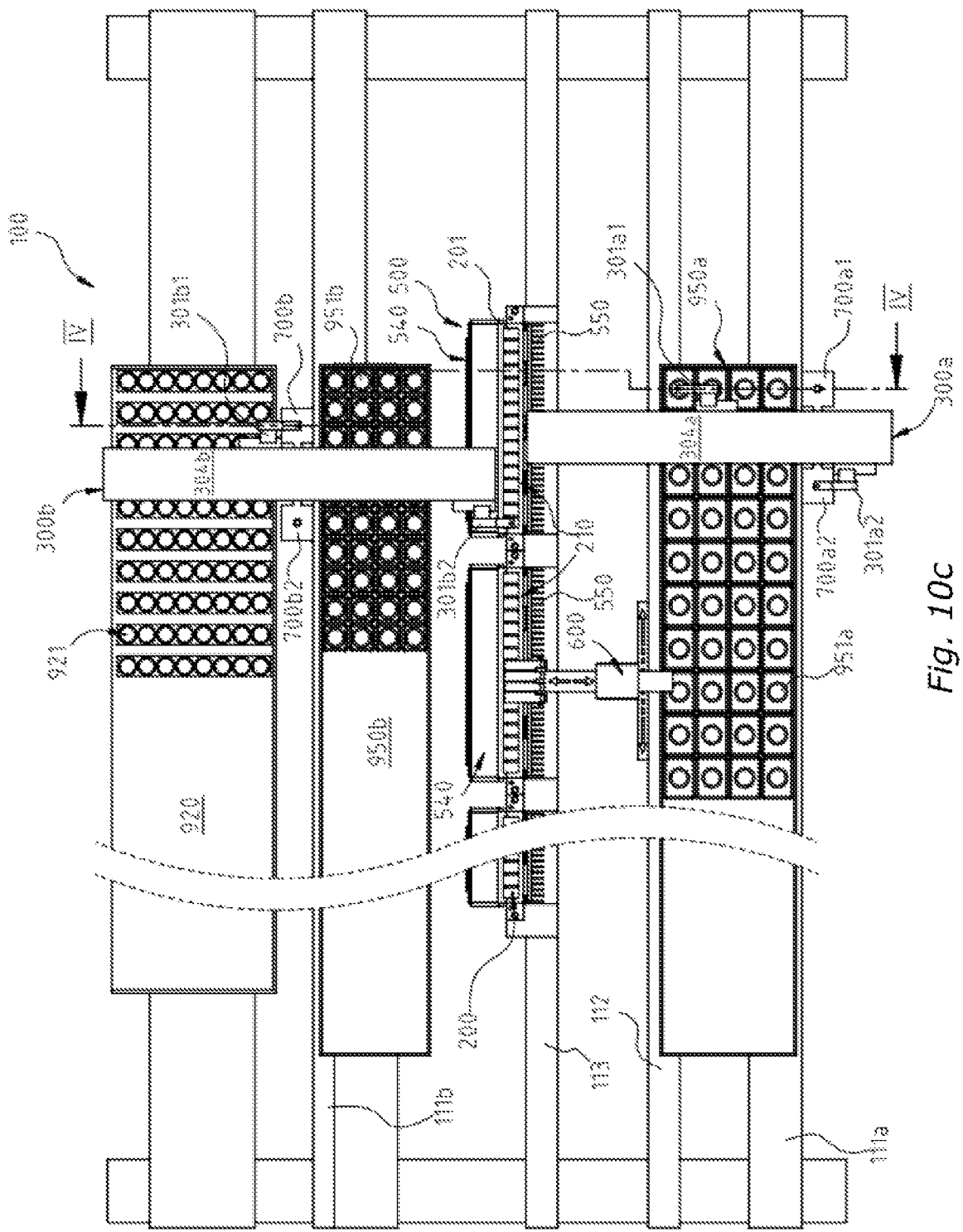
FIG. 10c shows a simplified plan view of the analyzer according to FIG. 10a, FIG. 11a shows a first variant of an optical measurement unit according to the invention for obtaining measurement signals from liquid media, in a three-dimensional view, looking toward the light-supplying unit according to FIGS. 10a to 10c.

The second embodiment variant of the automatic analyzer 100, which is described in FIGS. 10a to 10c, has the components that have already been explained in detail in connection with the first variant, such as pipettors 300a, 300b which are movable along the stationary cuvette array 200, needle washing units 700a1 to 700b2 which are preferably movable with the pipettors 300a, 300b, and a cuvette washing nit 600 which is movable along the cuvette array 200, and differs primarily in the optical measurement unit 500, which according to a first variant (see FIGS. 11a to 11f) is configured in a stationary manner and is fixedly assigned to the individual cuvettes 201.

The optical measurement unit 500 has the following basic elements:
  a light-supplying unit 540 for emitting an inlet radiation into the cuvettes 201 of the cuvette array 200, the light-supplying unit 540 having a plurality of LED light sources 541 which emit in a spectrally different manner in the UV/VIS/NIR wavelength range, and
  a detection unit 550 for detecting a measurement radiation exiting from the cuvettes 201 of the cuvette array 200 and for converting the measurement radiation into an electrical measurement signal, the detection unit 550 being configured such that at least one photodiode 551 is assigned in a fixed and stationary manner to each cuvette 201 of the cuvette array 200.

The first variant of the optical measurement unit 500 according to the invention, which is shown in FIGS. 11a to 11f, has at least one stationary light distributor device 542 which distributes the light from the individual LED light sources 541 among the individual cuvettes 201 of the stationary cuvette array 200.

The light distributor device 542 has a cavity formed by walls, the inner surfaces 543, 544, 545 of which, as well as the rear wall and the two end surfaces, are designed to be at least partially mirrored and/or diffusely reflective. The light distributor device 542 has, for each LED light source 541, an inlet opening 546 in the bottom surface 545 for feeding the light into the cavity and has, for each cuvette 201 of the cuvette array 200, an outlet opening 547 for feeding the light into the cuvette 201.

According to the invention, the inner surface 544 at the top of the light distributor device 542 that is located opposite the inlet openings 546 of the LED light sources 541 is designed to be corrugated and reflective, wherein the corrugations of the corrugated inner surface 544 are preferably oriented normal to the longitudinal extension of the light distributor device 542 in order to optimally distribute the light entering from the individual LED light sources 541 in the longitudinal direction of the light distributor device 542 (see FIG. 11d).

In order to ensure that the measurement radiation is applied to the cuvettes 201 as homogeneously as possible, the inner surface 543 of the light distributor device 542 at the top part that is located opposite the outlet openings 547 of the cuvettes 201 is designed to be diffusely reflective (see FIG. 11c). Byway of example, barium sulfate ($BaSO_4$) is a suitable material for coating the inner surface 543 in the field of view proceeding from the inlet window 202 of the cuvette 201.

In order to improve the spectral characteristic and to feed the light into the light distributor device 542, at least some LED light sources 541 of the light-supplying unit 540 have optical elements for collimation purposes and a narrowband filter on the output side.

Figure 11B:
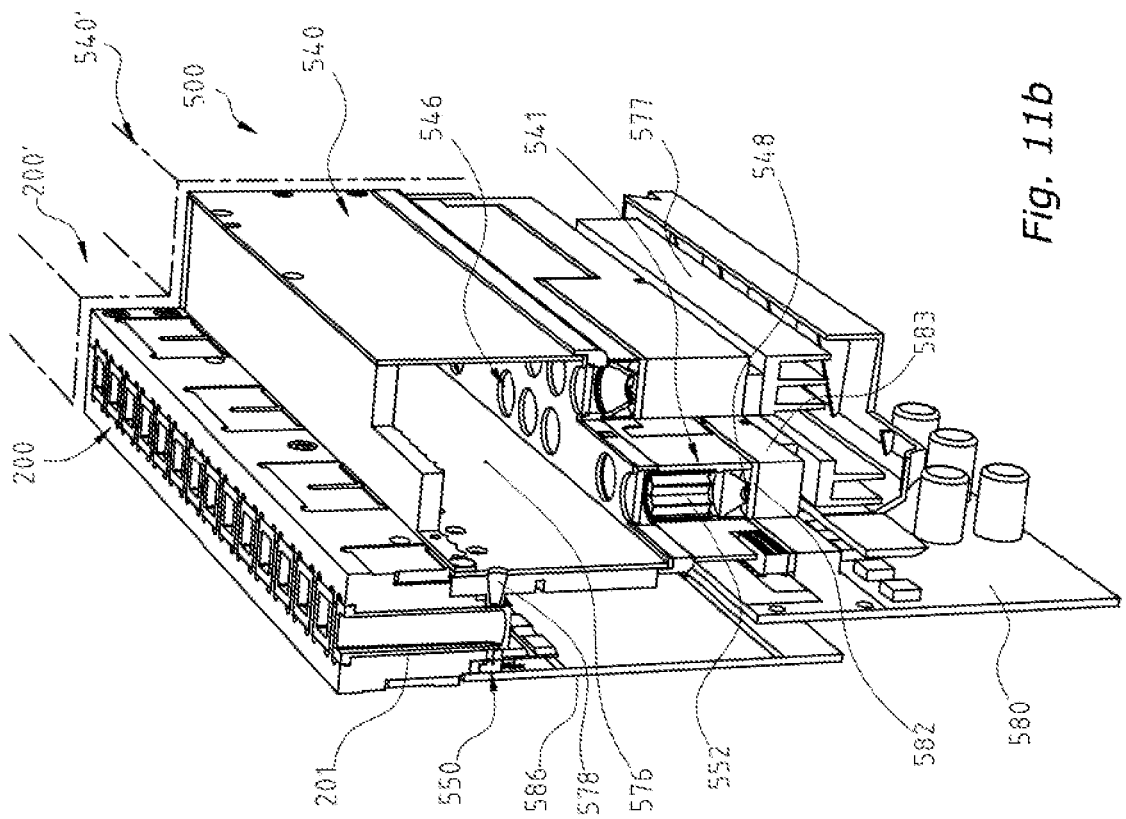
FIG. 11b shows the embodiment variant according to FIG. 11a in a three-dimensional view, looking toward the detection unit.
Figure 11A:
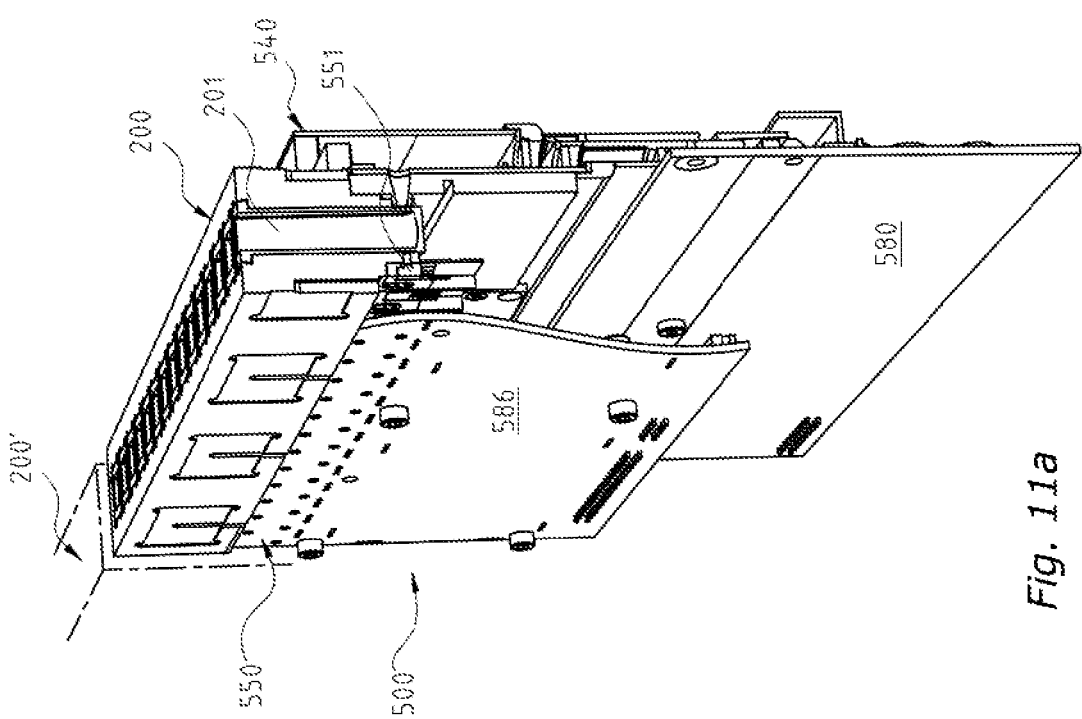
FIG. 11c shows a sectional illustration of the light-supplying unit according to FIG. 11a along the line II-II in FIG. 11d.
FIG. 11d shows a sectional illustration of the light-supplying unit according to FIG. 11a along the line III-III in FIG. 11c.
FIG. 11e shows a three-dimensional detail illustration of a tubular body of the light-supplying unit according to FIG. 11a, FIG. 11f shows an enlarged detail illustration from FIG. 11c.

As shown in FIG. 11a and in detail in FIG. 11c, the LED light source 541 may have an LED 548, arranged in a TIR lens 549, a tubular body 552 for eliminating non-parallel beam components of the LED, and a narrowband filter, preferably an interference filter 553, on the inlet side into the light distributor device 542.

In this case, the tubular body 552 may have elongate through-openings 570 extending parallel to the longitudinal axis of the LED light source 541, the walls 571 of said through-openings being made of a light-absorbing material or being coated with such a material (see the detail illustration shown in FIG. 11e). Therefore, within a certain tolerance, only rays which are aligned in parallel reach the interference filter 553, since deviating rays are absorbed by the tubular body 552.

The guiding or directing of light in the optical measurement unit takes place in multiple steps in order to meet the requirements:
  In the first step, the spatially broadly emitted light from the LEDs 548 is gathered by means of optical lenses, TIR lenses 549 or parabolic mirrors, is parallelized, and is directed toward the interior of the light distributor device 542.
  In the (optional) second step, components of the light that have not been sufficiently parallelized are prevented from proceeding further by means of the tubular body 552 or other tube-like elements.
  In the third step, optical bandpass filters, for example interference filters 553, are provided in order to obtain a predefined, narrowband light spectrum.
  In the fourth step, in the interior of the light distributor device 542, the light generated by the individual LED light sources 541 is distributed as homogeneously as possible and is directed into the individual cuvettes 201. To this end, the substantially cuboidal light distributor device 542 is configured such that the top surface has a corrugated structure 544 (see FIG. 11d) and the other inner surfaces are designed to be flat and mirrored or diffusely reflective, so that light over a spectral range from approximately 340 nm to 800 nm is reflected as effectively as possible. A diffusely reflective surface 543 is arranged opposite the outlet openings 547; all the other inner surfaces of the light distributor device 542 have mirrored and/or diffusely reflective surfaces. Arranged in the rear wall of the light distributor device 542 are the outlet openings 547, through which the light can pass directly to the inlet windows 202 of the cuvettes 201.

In the fifth step, a beam bundle that is directed into the interior of the cuvette 201 is created by a feedthrough 578, optionally with the interposition of one or more diaphragms between the light distributor device 542 and the cuvette 201.

In the sixth step, the measurement radiation is directed from the outlet window 203 of the cuvette 201 toward the photodiode 551 of the detection unit 550, optionally with the interposition of a diaphragm.

According to the invention, monitoring or reference detectors 575 are arranged on the light distributor device 542, on the outlet side of through-openings or pinhole diaphragms 576 arranged in a wall, for example in the rear wall, of the light distributor device 542, by which monitoring or reference detectors it is possible to detect fluctuations of the measurement radiation at any time. A pinhole diaphragm 576 together with a reference detector 575 may be assigned to each cuvette 201. If each cuvette 201 is assigned a reference photodiode, these are preferably located at the outlet openings 547 of the light distributor device 542. It is also possible to provide in the light distributor device 542 only two or three pinhole diaphragms 576 together with reference detectors 575 (see FIG. 11*a*).

As shown in FIGS. 11*a/b*, the stationary cuvette array 200 may be segmented or divided into multiple sections, wherein a separate light-supplying unit 540 is fixedly assigned to each segment 210.

Each segment 210 is assigned a common light distributor device 542 which extends over the entire length of the segment and which has a sufficient number of installation positions for LED light sources 541 for up to 16 optical channels with light of different wavelengths ($\lambda 1$ to $\lambda 16$). The individual LEDs of the LED light sources 541 may preferably be arranged in the form of an LED array on a common printed circuit board 582, for example made of aluminum. In order to increase the intensity, adjacent installation positions (see FIG. 11*a*) may be fitted with LED light sources of the same wavelength. In the region of the front inlet window 202 of each cuvette 201, which is adjacent to the light distributor device 542, the light distributor device 542 has a circular opening, the so-called outlet opening 547, through which the light generated by the LEDs is irradiated through the inlet window 202 into the interior of the cuvette 201. The feedthrough 578 in the cuvette receptacle 579, between the outlet opening 547 and the inlet window 202 in the cuvette 201, may be channel-shaped, may optionally contain diaphragms, and may preferably be made of a light-absorbing material (see FIG. 11*f*).

By distributing the light within the light distributor device 542 by multiple scatterings and reflections on the inner walls, the light from each optical channel of the LED light sources 541 passes through the circular outlet openings 547 into the inlet window 202 of each associated cuvette 201.

The intensity 1 of the light transmitted through the cuvettes 201 is measured by means of a stationary array of photodiodes 551 (at least one photodiode per cuvette), which are each placed fixedly behind the rear outlet window 203 of the cuvettes 201, said outlet windows being remote from the light distributor device 542.

Optionally, a second photodiode (not shown) may be arranged on each cuvette 201 at an angle rotated through, for example, 90° from the continuous beam path, in order to carry out nephelometric scattered light measurements.

To ensure a constant ambient temperature of the LED light sources 541, a solid aluminum block 583, which is temperature-controlled (possibility of cooling and heating) for example by means of Peltier components, is mounted on the printed circuit board 582 of the LED light sources 541.

The electronics for the optical measurement unit 500, which are shown schematically in FIG. 12*a*, consist of a plurality of circuit units which are distributed on a plurality of printed circuit boards and which are geometrically placed on the stationary cuvette array 200 (see arrow) according to their function.

In the example shown, the printed circuit board of the transmitting unit 580 contains 16 parallel current sources 581, which are each assigned to a particular light source (LED 548) with a specific wavelength. The current sources 581 may be regulated in terms of current strength and in terms of pulse length by an optical controller (584), so that a desired current pulse in terms of length and strength can be set for the light pulse. The LED power supply voltage can also be individually regulated for each LED channel. For temperature control purposes, the circuit board of the transmitting unit 580 is screwed to an aluminum block 583 having cooling fins 577 (see FIG. 11*b*) and is regulated by means of Peltier elements to a settable temperature, for example between 29° C. and 41° C. The thermal drift of the current sources 581 can thus be reduced to a minimum. The power loss occurring in the current sources 581 is evened out by the temporally successive actuation. Always only one current source 581 is activated per unit of time, and thus also always only light with a particular, predefined wavelength is generated.

The actual light sources are realized on a separate, cooled aluminum printed circuit board 582 by means of 16 selected LEDs 548 with the desired 16 wavelengths. The aluminum printed circuit board 582 is used on account of the better thermal coupling of the LEDs, is screwed to the aluminum block 583, and thus is also operated at a constant temperature (for example +37° C.). Despite different pulse lengths, the LEDs have a constant average temperature and thus also generate a low spectral shift.

The aluminum printed circuit board 582 having the LEDs is arranged directly on the light distributor device 542 (see FIG. 11*a*) in order to guarantee the best possible coupling of light into the light distributor device 542. The light from the LEDs 548 is first aligned in parallel via TIR lenses 549 and the tubular bodies 552, then is spectrally filtered via optical filters 553, and then is diffusely distributed as uniformly as possible in the interior of the light distributor device 542 so that the light can be coupled out to the 16 cuvettes 201 of the stationary cuvette array at 16 adjacent outlet openings 547 (see arrow 200 in FIG. 12*a*).

A further printed circuit board 585 is equipped with up to 16 monitoring or reference photodiodes 575, which detect the light generated by the LEDs 548 before it passes through the respective cuvette. However, use may also be made of just two global monitoring or reference photodiodes 575. In this case, the light is measured not directly in front of each cuvette but rather at multiple points of the light distributor device 542. Due to the constant geometric conditions, the light in front of each cuvette can be calculated with the aid of a geometry factor.

The printed circuit board 586 of the detector unit 550 is located on the outlet side of the cuvettes of the cuvette array 200. This printed circuit board contains 16 photodiodes 551 for the transmitted light exiting from the cuvettes 201. For each cuvette, the detector unit processes two analog values of the two associated photodiodes 551, 575 for transmitted light and monitoring or reference light. For the scattered light measurement (nephelometry), a third analog value can be detected from each cuvette by a photodiode arranged at the side, but the signal path thereof is not shown in FIG. 12a for reasons of clarity.

The two signal paths starting from the photodiodes 551, 575 are synchronously processed by two 16:1 multiplexers 587, inverters, integrators and ADCs, and are converted into a digital measured value. The multiplexers 587 make it possible to select the for example 16 cuvette channels and to switch between these in temporal succession in a configurable order.

If the stationary cuvette array 200 is segmented, and if a separate light distributor device 542 is fixedly assigned to each segment 210 (see FIG. 11a/b), additional printed circuit boards are used for the transmitting unit 580, the printed circuit board for the LEDs 582, the printed circuit board for the monitoring or reference diodes 575 and optionally the printed circuit board for the detector unit 586, said printed circuit boards being indicated in dashed line. By way of example, if 96 cuvettes 201 are arranged in the stationary cuvette array 200, six separate light distributor devices 540 may be provided, each having 16 outlet openings to the fixedly assigned cuvettes 201.

The central printed circuit board 584 for the optical measurement unit 500 is equipped with the optical controller. The optical control unit is realized by a programmable logic (FPGA) as a state machine and can at the same time operate the transmitting unit 580 and the detector unit 586. In order to generate the correct time sequence, the individual light measurements are broken down into light and dark measurements and can be parameterized differently line by line in a configuration memory. The state machine works through these configuration lines in sequence, it also being possible for lines to be skipped. The distinction between light and dark measurements is defined by a flag in the configuration line, as is the desired cuvette channel and the light source. The configuration line also contains the desired delay settings, current strength and pulse length, and also the choice of reference photodiode, LED power supply voltage, oversampling and averaging settings and the period duration.

The detector unit 586 is actuated in a manner synchronized with the transmitting unit 580 and can be set by global parameters with averaging or oversampling settings. The desired integration time, by which the light signal is to be integrated, is also read out from the configuration line. The delay time for the integrator and the integration slope can also be selected here by means of global parameters, so that the settling times of the measurement signal and the integration speed can thus be switched over.

The analog measured value is thus selected from the corresponding photodiode 551 with transimpedance converter via the multiplexer 587 and is measured by means of an inverter and an integrator and an optional logarithmic amplifier and is digitized by a high-resolution ADC measurement with or without oversampling. Finally, if a scattered light measurement also takes place, three analog measured values (transmitted light, monitoring or reference light, scattered light) are digitized simultaneously by three ADCs and are stored line by line in the internal memory as raw measured values. It is essential that the measurement of transmitted light and monitoring or reference light and optionally scattered light takes place simultaneously.

The internal memory contains all the raw data and is cyclically read by the evaluation processor by means of software and is converted by a conversion algorithm into a final measured value. The conversion takes into account the dark value and the light value and also the $I_0$ measurement and the $I_1$ measurement before and after the reagents have been admixed. The change in the measured values over time can also be detected through successive measurements. It is essential that the measurements take place periodically and give rise to a repeatable measurement cycle according to the set period duration.

For each cuvette, the calculated data are packed into defined data packets and are transmitted to the main computer 588 by means of a local Ethernet interface. By virtue of this data reduction, it I possible to process all cuvettes of the cuvette array 200 of the optical measuring unit 500 and transfer the data to the main computer 588.

In the measurement method, it is possible to measure I or $I_0$ in rapid succession for each cuvette with a high sampling frequency (>1 Hz). There are various possibilities for actuating and reading the multiple LED light sources 541 and photodiodes 551 of the detection unit 500.

The periodic actuation signal for the individual LED light sources 541 is defined, with regard to the pulse duration and integration duration and also the current level used, for each combination of cuvette and wavelength for the measurement mode used and is not changed during operation.

In the example shown, the actuation of 16 LED light sources 541 takes place via 16 separate current sources 581 and the associated hardware. The exposure of each cuvette to each spectral channel of the LED light sources 581 and the integration times used are individually defined (16×16 combinations). The individual LEDs (or in some positions also multiple LEDs in order to increase the intensity) each sequentially emit one light pulse in the course of one measurement cycle, said light pulse being reflected multiple times on the inner walls in the interior of the light distributor device 542 and finally reaching the 16 associated cuvettes 201 through the 16 outlet openings 547 (see FIG. 11c).

Various measurement modes are provided:

Mode 1: Detection of the dynamic flashing LED signal with constant integration time and variable current strength and pulse duration (256 flashes)

Mode 2: Detection of the static LED signal with variable integration time (256 LED actuations) and variable current strength Mode 3: Detection of the static LED signal with variable integration time (16 LED actuations)

The measurement takes place individually for each combination of cuvette and wavelength, one light pulse being generated for each measurement point in modes 1 and 2.

Figure 12B:
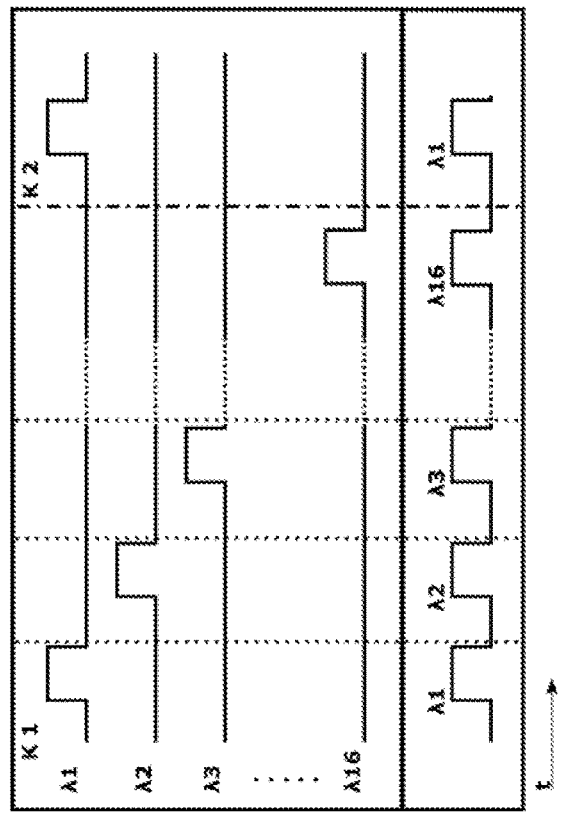
FIG. 12a shows a block diagram regarding the electronic actuation of the optical measurement unit according to FIG. 11a, FIG. 12b shows a first diagram to illustrate a measurement process (modes 1 and 2)
FIG. 12c shows a second diagram to illustrate a measurement process (mode 3)

As shown in FIG. 12b, the spectral channels ($\lambda 1 \ldots \lambda 16$) of the individual LED light sources 581 are activated and deactivated in a set order in modes 1 and 2. The resulting light flashes are detected and measured by the photodiode 551 selected by the multiplexer 587. After running through all the spectral channels, the sensors are changed over from the cuvette position K1 to the cuvette position K2 and the light flashes required for the latter are generated in the same order. After fully running through all 16 cuvette positions (that is to say 16×16 light flashes), one sampling is complete and the next one can be initiated. By virtue of this process, up to four samplings per second can be achieved. In modes 1 and 2, alternating dark and light measurements are carried out one after the other, so that in total 512 individual measurements are carried out per sampling.

The measurement method according to modes 1 and 2 is thus characterized in that the spectral channels $\lambda 1 \ldots \lambda n$ of the individual LED light sources 581 are activated and deactivated in a predefined order, wherein in each case the photodiode 551 arranged in a first cuvette position K1 is detected, and in that, after running through all the spectral channels in the first cuvette position K1, a changeover to the next cuvette position K2 takes place. The time duration for one cycle in measurement mode 1 or 2 is >=0.25 seconds.

Figure 12C:
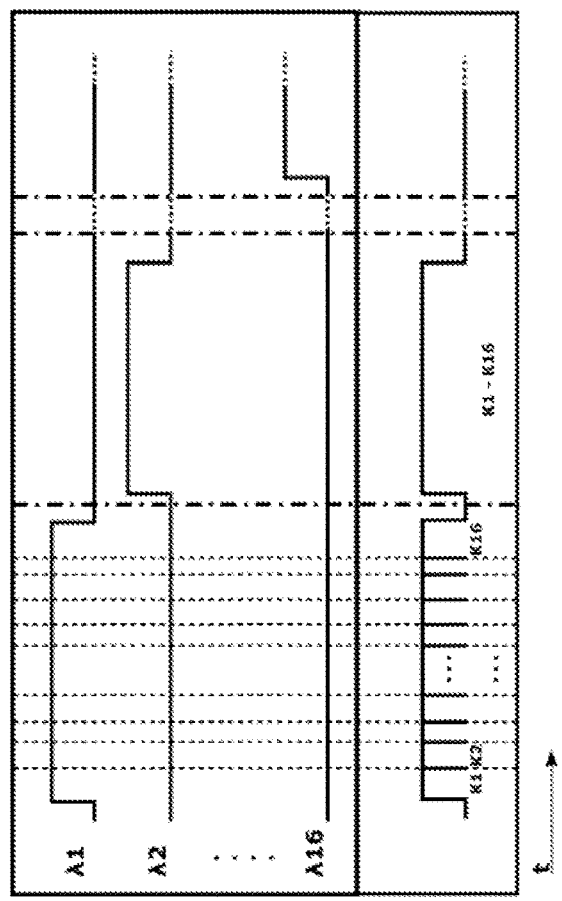

In measurement mode 3, which is shown schematically in FIG. 12c, the LED light sources 541 are switched in a different order than in mode 1 or 2.

Each LED light source 541 or each spectral channel is switched on only once in the cycle (indicated by the dash-dotted line), and thereafter all 16 cuvettes are measured one after the other, with no dark measurement taking place between these individual measurements. The first cuvette K1 is measured with a delay, so that the associated photodiodes 551 of the detector unit 550 have sufficient time to settle. The other cuvettes K2 to K16 can be measured more rapidly in succession without any additional settling time.

Within one cycle, each LED is switched on only once, with all 16 cuvettes being measured in each case. If a dark measurement is necessary, a dark value is measured once, for example at the start or end of the cycle for measuring the 16 cuvettes.

In the case of 16 wavelengths or 16 spectral channels ($\lambda 1 \ldots \lambda 16$) and 16 cuvette positions, 16×16 light measurements are required. If the 16 dark measurements (once per cycle) are added, this results in 272 individual measurements. The time duration for one cycle in measurement mode 3 is >=0.5 seconds.

The measurement method according to mode 3 is characterized in that the spectral channel M of the first LED light sources 581 is activated, with the photodiodes 551 arranged in the cuvette positions K1 . . . Km being detected in a predefined order, wherein, after running through all the cuvette positions K1 . . . Km, the next spectral channel $\lambda 2$ of the next LED light sources 581 is activated.

Advantage of mode 3:
Mode 3 is on the whole faster than the 512 dark/light measurements carried out in an alternating manner in mode 1 and mode 2, because overall fewer measurements and fewer settling times are required for the photodiodes.
The settling time of the photodiodes need only be taken into account prior to the first light measurement of the cuvette K1; the remaining 15 cuvettes K2 to K16 can follow immediately thereafter.
On the whole, therefore, much shorter sampling times per cycle are achieved compared to mode 1 or 2.

In the second variant of the optical measurement unit 500 according to the invention, which is shown in FIGS. 13a and 13b, the light-supplying unit 540 has at least one unidimensional, rod-shaped light source array 554 having a plurality of LED light sources 541, which is oriented along the stationary cuvette array 200, for example of an analysis device, and is designed to be movable along the stationary cuvette array 200. Each LED light source 541 of the light source array 554 can thus be assigned to each cuvette 201 of the stationary cuvette array 200.

In this embodiment variant, preferably in each case one LED light source 541 together with a beam splitter 555 and a reference detector 556 is arranged in a common, for example tubular, housing 560. The light paths of the individual LED light sources 541 arranged next to one another can thus be separated.

Individual LED light sources 541 of the rod-shaped light source array 554 may have collimating optical elements 557 for feeding the light into the cuvettes 201 and a narrowband filter 558 for improving the spectral characteristic of the light. In addition, a condenser, preferably a converging lens 559, may be provided for focusing the light into the cuvette 201.

If individual LED light sources 541 are configured as narrowband-emitting and parallel-light-emitting laser diodes, the optical elements 557 for collimation, for filtering 558 and for focusing 559 may be omitted entirely or at least in part.

The photodiodes 551 of the detection unit 550 which are fixedly assigned to the individual cuvettes 201 of the stationary cuvette array 200 are preferably arranged as a photodiode array on a common circuit board 572. The detection unit 550 has—coming from each cuvette 201 of the stationary cuvette array 200—a receptacle 573 which is for example tubular and in which—if necessary—optical elements 569 for focusing the measurement radiation onto the photodiode 551 and—if necessary—a filter element 574 are arranged.

With this module variant, various photometric and turbidimetric measurements can be carried out on multiple cuvettes 201 of a stationary, linear cuvette array 200 at single and/or multiple wavelengths in the wavelength range of ultraviolet and visible light, wherein the individual LED light sources 541 of different wavelengths of the light-supplying unit 540 are successively positioned in front of the individual cuvettes 201. The intensity of the light that has passed through the respective cuvette 202 is then measured in each case by the fixedly assigned, stationary detector unit 550. As an alternative to the positioning, a measurement "on the fly", that is say while moving past, is also possible.

In the third variant of the optical measurement unit 500 according to the invention, which is shown in FIGS. 14a to 14c, the LED light sources 541 of the light-supplying unit 540 are arranged as a 2D LED array 561, wherein a stationary 2D LED array 561 is fixedly assigned to each cuvette 201 of the stationary cuvette array 200. In this embodiment variant, in a manner similar to the first variant, no relative movement takes place between the cuvettes 201 of the cuvette array 200 on the one hand and the light-supplying unit 540 and the detection unit 550 on the other hand, as a result of which the measurement processes can be significantly accelerated due to the omission of mechanical movements within the optical measurement unit 500.

According to one sub-variant of the third embodiment variant, the LED light sources 541 in the light-supplying unit 540 may be arranged as a single 2D LED array 561 (as in the detail illustration shown in FIG. 14c), wherein the light-supplying unit 540 is designed to be movable along the entire stationary cuvette array 200 or along a segment 210 of the cuvette array 200 (in a manner similar to what is shown in FIG. 13a), such that the 2D LED array 561 can be assigned to each cuvette 201 of the cuvette array 200 or to each segment 210 of the cuvette array 200. If the cuvette array 200 is segmented, a light-supplying unit 540 having a 2D LED array 561 is provided for each segment 210.

In order to feed the light from the individual LEDs 548 of the 2D LED array 561 into the cuvettes 201, a 2D lens array 562 for collimating the light from the individual LEDs is provided. In addition, a 2D filter array 563 for narrowband filtering of the light is arranged in the beam path in order to improve the spectral characteristic. The filter array 563 may have no filter function in some positions, for example if a narrowband- and parallel-emitting laser diode is arranged in this position of the 2D LED array 561.

Also provided in the beam path is at least one condenser, preferably a converging lens 564, for focusing the light into the individual cuvettes 201.

Particular preference is given to embodiment variants in which the 2D LED array 561 consists of LED emitters bonded to a single substrate 565, wherein the 2D lens array 562 is a 2D microlens array and the 2D filter array 563 is a 2D micro-interference filter array.

In each case one LED light source 541, comprising a 2D LED array 561, a 2D lens array 562, a 2D filter array 563 and a converging lens 564, may preferably be arranged together with a beam splitter 566 and a reference detector 567 in a common housing 568.

In this variant, each cuvette 201 has an individual photometer unit consisting of a light-supplying unit for light with up to 9, 12 or 16 different wavelengths ($\lambda 1$ to $\lambda n$) which are generated by individual LEDs 548. When using commercial LEDs (side length approximately 2 mm and a spacing of approximately 0.5 mm) which are soldered to a circuit board by means of push-through mounting, a surface area of approximately 10×10 mm$^2$ is to be expected in the case of a 4×4 array.

When arranging the semiconductors of the individual LEDs as a COB (chip on board), these can be realized on a space-saving surface area of less than 5×5 mm$^2$. In the case of COB technology, the LED chips are preferably bonded directly to a highly thermally conductive aluminum circuit board.

With an edge length of 300 to 900 μm and a spacing of approximately 100 μm, 16 LED chips for example can be accommodated on a square surface area having an edge length of 1.6 to 4 mm. The individual collimator lenses of the 2D microlens array and also the interference filters of the 2D interference filter array accordingly have diameters of up to 900 μm. In order to further improve the collimation (parallelization), a pinhole diaphragm array may be placed onto the LED array so that the light-emitting areas can be presented in a sufficiently punctiform manner regardless of the size of the emitting semiconductor surfaces.

The LED chips may be arranged on the 2D array in columns or rows, for example 3×3, 3×4 or 4×4, or also in concentric circles.

As already described in connection with the variant shown in FIG. 13*a/b*, the detection unit 550 has, coming from each cuvette 201 of the stationary cuvette array 200, a receptacle 573 which is for example tubular and in which optical elements 569 for focusing the measurement radiation onto the photodiode 551 and—if necessary—a filter element 574 are arranged.

The photodiodes 551 of the detection unit 550, which are fixedly assigned to the individual cuvettes 201, are preferably arranged as a photodiode array on a common circuit board 572.

Figure 15C:
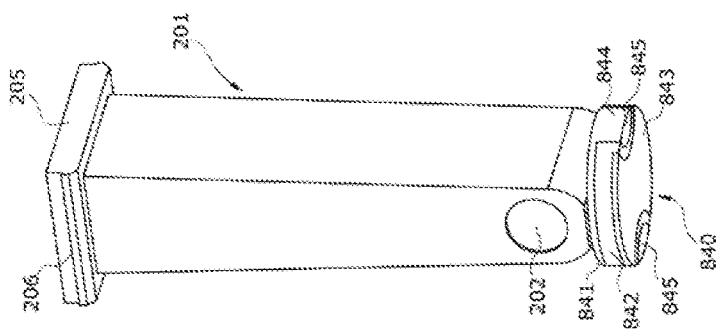
FIG. 15a shows a device according to the invention for mixing and controlling the temperature of liquid media, in a three-dimensional illustration of an automatic analyzer according to FIGS. 10a to 10c.
FIG. 15b shows the device according to FIG. 15a in a sectional illustration according to FIG. 15a, FIG. 15c shows a cuvette together with an ultrasonic transducer of the device according to the invention as shown in FIG. 15a, in a three-dimensional view.
Figure 15B:
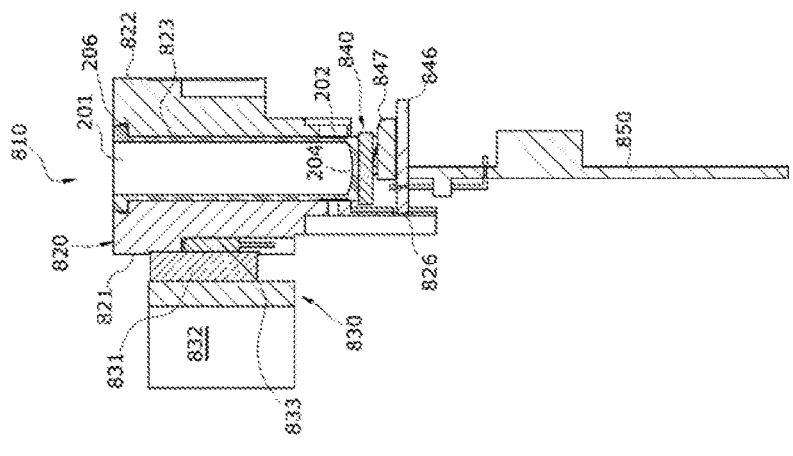
Figure 15A:
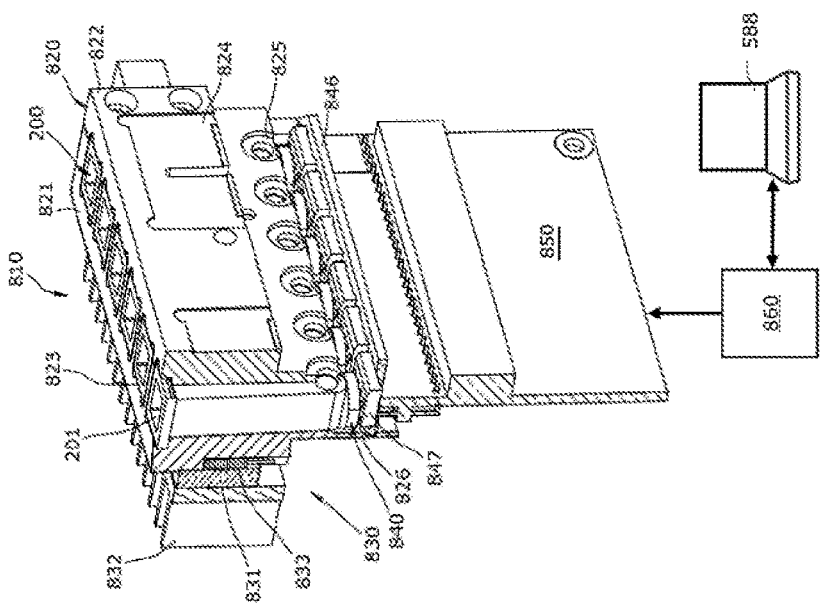

The combined device 810 shown in FIGS. 15*a* to 15*c* for mixing and controlling the temperature of liquid media serves to control the temperature of the liquid media introduced into the lined-up cuvettes 201 of a cuvette array 200. In the illustrated example, this is a linear, stationary cuvette array 200.

The individual cuvettes 201 of the cuvette array 200 are arranged in a temperature-controllable cuvette block 820, for example made of aluminum, wherein the walls of the funnel-shaped receptacles 823 bear with a form fit against the walls of the cuvettes 201 in order to ensure optimal heat transfer. The cuvette block 820 consists of a base part 821 containing the receptacles 823 and of a front part 822 which can be opened by a lateral pushing movement.

A temperature control device 830 is arranged on the cuvette block 820, for example on the base part 821, said temperature control device having a cooling and heating device, for example in the form of one or more Peltier elements 831 and also cooling fins 832. In order to regulate the temperature of the cuvette block 830, a temperature sensor 833 is arranged in a receptacle between the base part 821 and the Peltier element 831.

On the openable front part 822 of the cuvette block 820, it is possible to see connection surfaces 824, which can also be used to attach a cooling and heating device, for example Peltier elements. The front part 822 additionally has openings 825 corresponding to the measurement windows 202 of the cuvettes 201, in order to enable an optical measurement of the liquid media in the cuvettes 201.

An ultrasonic transducer 840, for example a thickness-mode transducer, is attached to the bottom 204 of each cuvette 201, for example by adhesive bonding or by being injection-molded therewith during manufacture of the cuvette, by which ultrasonic energy can be introduced into the cuvette 201. The ultrasonic energy introduced is used both for mixing the liquid media and also for targeted heating—in addition to the base load resulting from the temperature control by the cuvette block 820.

The ultrasonic transducer 840 is configured as a piezoelectric thickness-mode transducer which—as shown in detail in FIG. 15*c*-substantially consists of a disk-shaped piezoelectric element 842 and contact electrodes 841 and 843 arranged on both sides. The electrode 841 on the cuvette side is contacted with the lower electrode 843 via lateral contact strips 844 and forms crescent-shaped contact areas 845 at these locations.

For each cuvette 201 and the ultrasonic transducer 840 thereof, a contact block 847 supported by a spring contact board 846 is provided, said contact block having four contact springs 848, two of which contact the crescent-shaped contact surfaces 845 and two of which contact the lower contact electrode 843 of the ultrasonic transducer 840. The cuvette 201 has, at the filling opening 207, a collar 205 and also stop strips 206 on opposite sides, by which the cuvette 201 is held in the cuvette block 820 counter to the pressure of the contact springs 848.

The edge of the spring contact board 846 is inserted in a horizontally extending groove 826 of the cuvette block 820 and is supported against the downwardly projecting decoder board 850, the circuits of which will be explained in greater detail in FIG. 16.

Figure 16:
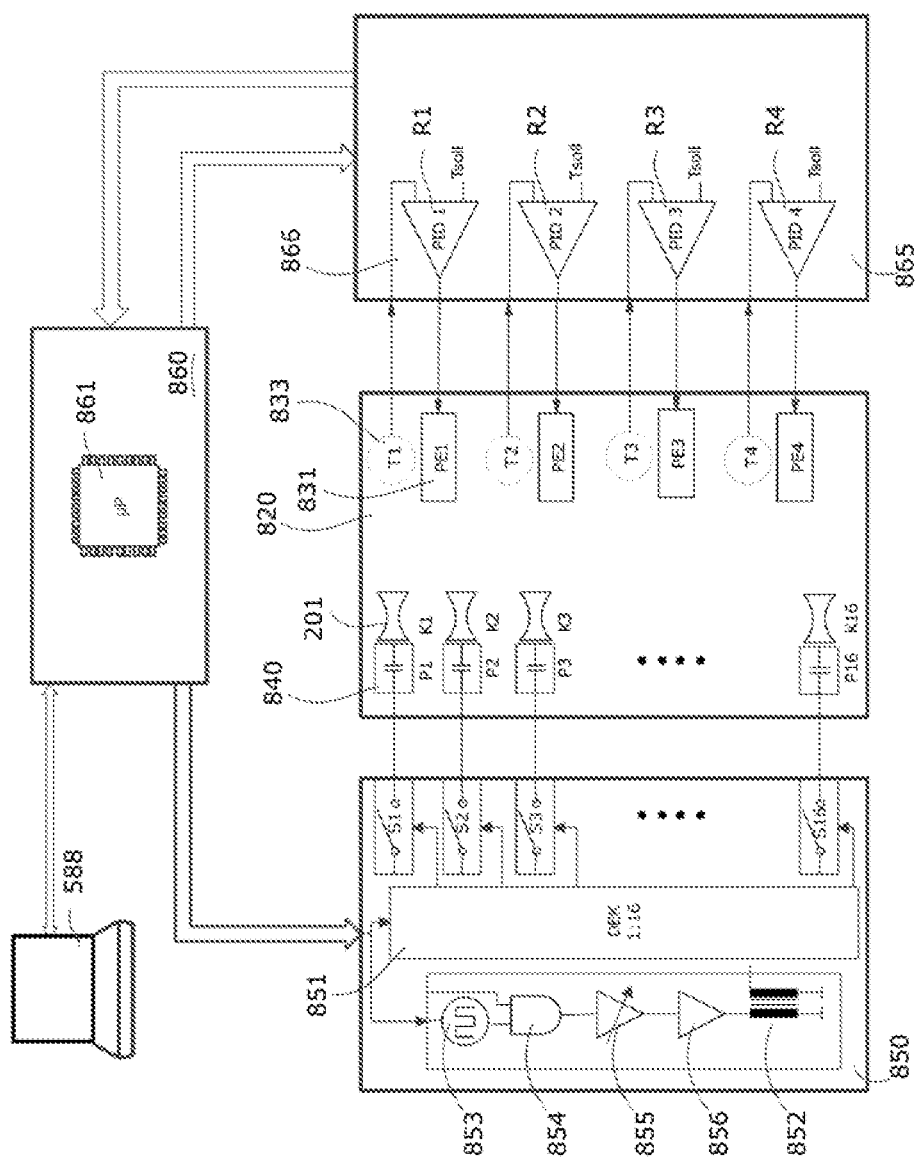
FIG. 16 shows a block diagram regarding the electronic actuation of the device for mixing and controlling the temperature of liquid media according to FIG. 15a, FIG. 17a shows a temperature diagram to illustrate a first exemplary embodiment of a temperature control and mixing process for a liquid.

FIG. 16 shows a block diagram regarding the electronic actuation of the device for mixing and controlling the temperature of liquid media according to FIG. 15*a*, said block diagram comprising the functional blocks personal computer 588, controller board 860, decoder board 850, cuvette block 820, and a temperature control circuit 865.

The controller board 860 has an FPGA (Field Programmable Gate Array) as the processor 861 and serves to control the decoder board 850 and also the temperature control circuit 865. The personal computer 588 may be connected to the controller board 860, for example via an Ethernet interface, and depending on the mixing and temperature control task to be performed in one of the cuvettes 201 of the cuvette block 820 transmits appropriate instructions to run firmware programs on the controller board 860, and also serves for the return transmission of control data, such as the measured temperatures for example, for controlling the temperature of the cuvette block 820.

Cuvettes 201 together with the associated ultrasonic transducers 840 are arranged in the cuvette block 820, respectively at the positions K1 to K16 and P1 to P16, wherein in the example shown, for temperature control purposes, a respective Peltier element 831 together with the associated temperature sensor 833 is provided in the positions PE1 to PE4 and T1 to T4.

The temperature control circuit 865 thus has four temperature control loops 866, each consisting of a Peltier element 831, a temperature sensor 833 and a PID (Proportional, Integral, Derivative) controller R1 to R4, and is connected via an interface to the controller board 860 for data exchange purposes (receiving parameters such as temperature setpoints and sending back measured temperatures from the temperature control circuit 865 to the controller board 860).

The decoder board 850 is likewise connected via an interface to the controller board 860 and receives from the latter control signals for selecting individual ultrasonic transducers 840 via the decoder circuit 851 implemented on the decoder board 850 and the associated optical switches 857 in the positions S1 to S16, as well as control signals for parameterizing the oscillator circuit 852. The oscillator circuit 852 receives control signals for adapting the frequency, duty cycle, burst pattern, amplitude, phase, and ON and OFF states of the signal generation of the oscillator. The oscillator circuit 852 comprises a voltage-controlled oscillator 853 (VCO), the frequency signal of which can be modulated via a burst generator 854. The amplitude of the modulated signal can additionally be adapted via a controllable preamplifier 855 and also a downstream amplifier output stage 856. The final amplified signal is stepped up by a transformer to the required operating voltage of the ultrasonic transducers 840 and is fed to one of the 16 piezoelectric ultrasonic transducers 840 on the cuvettes 201 on the cuvette block 820 via the respective optical switch 857 in S1 to S16 respectively selected by the decoder circuit 851.

Figure 17B:
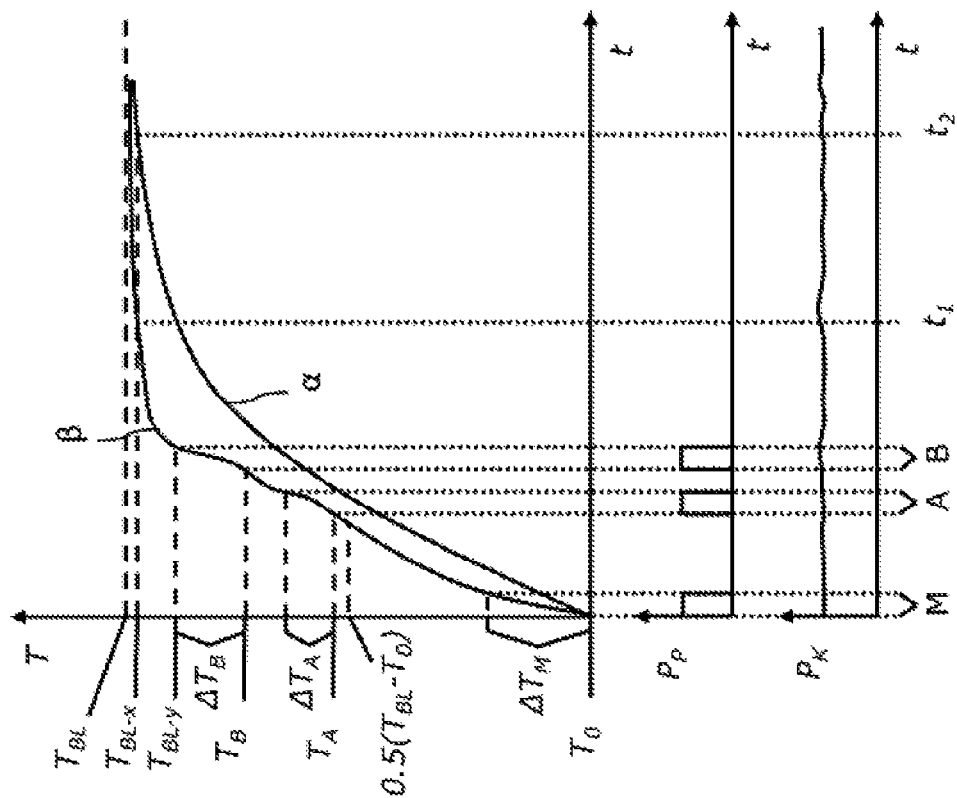
FIG. 17b shows a temperature diagram to illustrate a second exemplary embodiment of a temperature control and mixing process for a liquid.
Figure 17A:
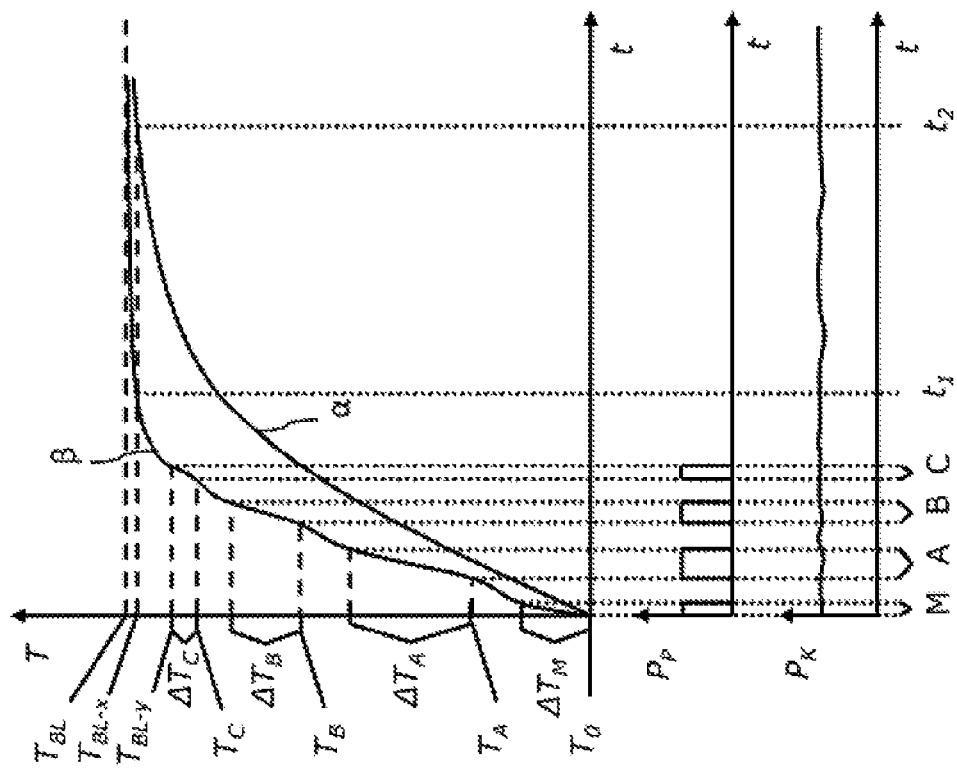

The diagram in FIG. 17a shows a first example of a process according to the invention for controlling the temperature of a sample/reagent mixture in a cuvette which is arranged in a temperature-controllable cuvette block (see FIG. 15a).

The temperature curve α shows the heating of the sample/reagent mixture only by the cuvette block controlled to the temperature $T_{BL}$ wherein the target temperature at which the sample/reagent mixture can be measured is not reached until the time $t_2$. If ultrasonic boosts are introduced in the time periods M and A to C, the required target temperature is reached much earlier, at the time $t_1$, as shown in the temperature curve β. The temperature of the cuvette block is controlled using a substantially constant electric power $P_{BL}$.

1) Preheating the cuvette block, with empty cuvettes located therein, to a block temperature $T_{BL}$ (typically 37.0 to 37.5° C.) and stabilizing the block temperature to within 0.1° C.
2) Filling an empty cuvette with a sample/reagent mixture of temperature $T_0$. After being pipetted into the cuvette, the sample/reagent mixture typically has a temperature of 10-15° C., because the pipetted reagents come from a storage area that is cooled to 5° C. and heat up to 10-15° C. in the pipettor and in the supply lines.
3) Emitting an ultrasonic signal for a predefined cumulative duration M, which, in the case of an ultrasonic signal having the average electric power $P_P$, introduces a quantity of energy M×$P_P$ into the sample/reagent mixture and brings about a calculated change in temperature $\Delta T_M$, this being calculated from variable properties of the sample/reagent mixture which are known from the data of the analysis to be carried out, such as heat capacity, viscosity, thermal conductivity, and also the volume thereof, and constant data stored in the device. The quantity of energy introduced in the duration M is enough to mix the sample/reagent mixture sufficiently.

A mixing duration of 1 to 3 seconds is typically sufficient for homogeneous mixing, wherein the change in temperature $\Delta T_M$ of a 2-second mixing pulse for example may be approximately 3° C.

Alternatively, for a given ultrasonic power PP, the mixing duration M that is necessary in order to obtain a stable measurement signal or incubation process can be determined by experiments on different sample/reagent mixtures and can be stored in the device.

As another alternative method, an optical signal of an analyte measurement can be continuously measured from the sample/reagent mixture and the mixing process can be terminated as soon as a stable signal is obtained, wherein the change in temperature $\Delta T_M$ in this case is calculated—as mentioned—from known thermal characteristics.

4) Observing a pause >1 s (in order to cool the bottom of the cuvette and the site of adhesion to the ultrasonic transducer).
5) Emitting one or more ultrasonic signals, optionally interrupted by pauses >1 s, at a calculated temperature $T_A$ for a predefined cumulative duration A+B+C+n, which corresponds to an additional calculated change in temperature $\Delta T_A + \Delta T_B + \Delta T_C + \Delta T_n$, wherein, after the last ultrasonic pulse has been emitted, a temperature $T_{BL-y}$ is reached which is below the temperature $T_{BL-x}$. From this temperature onward, the input of heat into the cuvette contents takes place purely via heat conduction between the cuvette block 820 and the cuvette contents.
6) Reaching a temperature $T_{BL-x}$ which is acceptable for the analysis and which is lower than the temperature of the cuvette block by the value x, where x is typically at a specified value of 0.1-0.5° C. The acceptable temperature is fixed and is between 36.5 and 37.5° C. The temperature constancy throughout the duration of a subsequent optical measurement should be around 0.1° C.

The diagram in FIG. 17b shows a second example of a process according to the invention for controlling the temperature of a sample/reagent mixture in a cuvette which is arranged in a temperature-controllable cuvette block (see FIG. 15a).

1) (as example) Preheating the cuvette block, with empty cuvettes located therein, to a block temperature $T_{BL}$ (typically 37.0 to 37.5° C.) and stabilizing the block temperature to within 0.1° K.
2) (as example 1) Filling an empty cuvette with a sample/reagent mixture of temperature $T_0$. After being pipetted into the cuvette, the sample/reagent mixture typically has a temperature of 10-15° C., because the pipetted reagents come from a storage area that is cooled to 5° C.
3) (as example 1) Emitting an ultrasonic signal for a predefined cumulative duration M, which, in the case of an ultrasonic signal having the average electric power $P_P$, introduces a quantity of energy M×$P_P$ into the sample/reagent mixture and brings about a calculated change in temperature $\Delta T_M$, this being calculated from variable properties of the sample/reagent mixture which are known from the data of the analysis to be carried out, such as heat capacity, viscosity, thermal conductivity, and also the volume thereof, and constant data stored in the device.

Depending on the stirring task, the suitable cumulative duration of required stirring processes is typically from 1 to 3 seconds, wherein the change in temperature $\Delta T_M$ of a 2-second mixing pulse for example may be around 3° K.

Alternatively, for a given ultrasonic power $P_P$, the mixing duration M that is necessary in order to obtain a stable measurement signal or a washing or incubation process can be determined by experiments on different sample/reagent mixtures and can be stored in the device.

As another alternative method, an optical signal can be continuously measured from the sample/reagent mixture and the mixing process can be terminated as soon as a stable signal is obtained, wherein the change in temperature $\Delta T_M$ in this case is calculated—as mentioned—from known thermal characteristics.

4) (as example 1) Observing a pause >1 s (in order to cool the bottom of the cuvette and the site of adhesion to the ultrasonic transducer).

5) Emitting one or more ultrasonic signals, optionally interrupted by pauses >1 s, at a calculated temperature 0.5× $(T_{BL}-T_0)$ for a predefined cumulative duration A+B+n, which corresponds to an additional calculated change in temperature $\Delta T_A+\Delta T_B+\Delta T_n$, wherein, after the last ultrasonic pulse has been emitted, a temperature $T_{BL-y}$ is reached which is below the acceptable temperature $T_{BL-x}$ and which can reliably be calculated. From this temperature onward, the input of heat into the cuvette contents takes place purely via heat conduction between the cuvette block and the cuvette contents.

6) (as example 1) Reaching a temperature $T_{BL-x}$ which is acceptable for the analysis and which is lower than the temperature of the cuvette block by the value x, where x is typically at a specified value of 0.1-0.5° K. The acceptable temperature is fixed and is between 36.5 and 37.5° C. The temperature constancy throughout the duration of a subsequent optical measurement should be around 0.1° K.

The third embodiment variant of the automatic analyzer 100, which is described in FIGS. 18*a*, 18*b* and 19*a* to 22, has the components that have already been explained in detail in connection with the first and second embodiment variants, such as pipettors 300*a*, 300*b* which are movable along the stationary cuvette array 200, needle washing units 700*a*1 to 700*b*2 which are preferably movable with the pipettors 300*a*, 300*b*, and a cuvette washing unit 600 which is movable along the cuvette array 200, and additionally also a device for carrying out heterogeneous immunoassays 410.

Figure 18A:
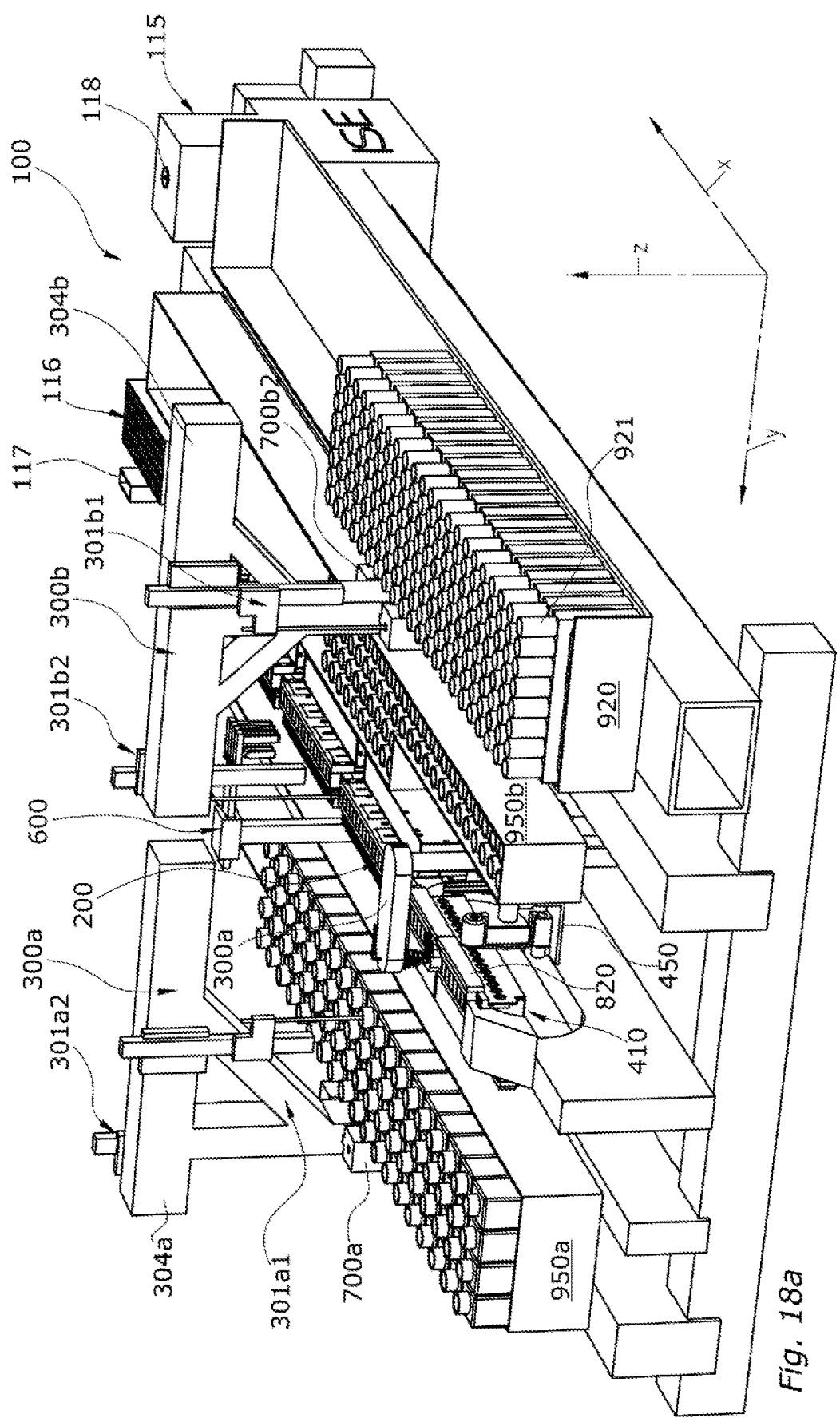
FIG. 18a shows a third embodiment variant of an automatic analyzer according to the invention for carrying out chemical, biochemical and/or immunochemical analyses of liquid samples, having a linear, stationary cuvette array and a device for carrying out heterogeneous immunoassays, in a three-dimensional overall view.
Figure 18B:
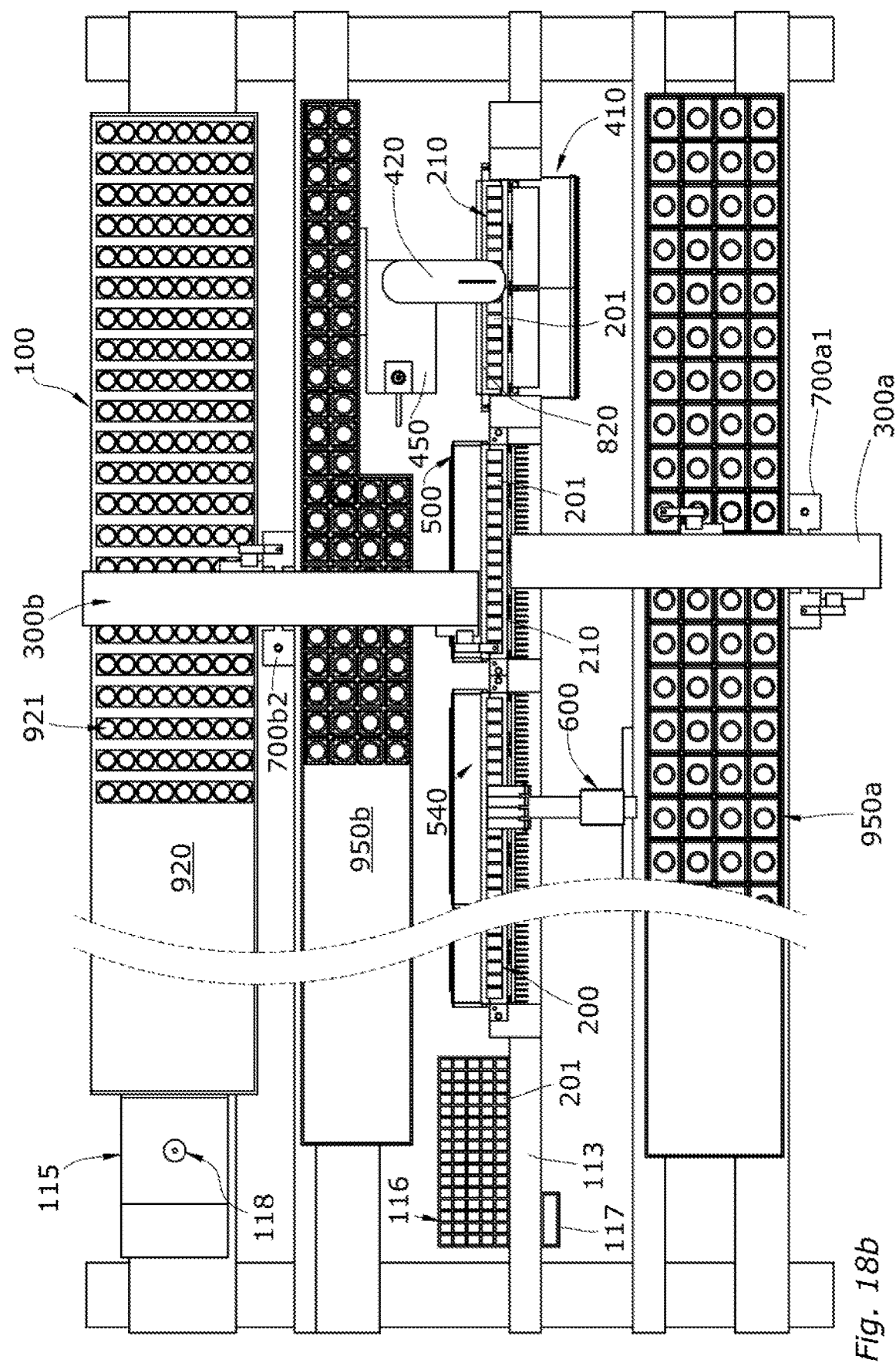
FIG. 18b shows a plan view of the automatic analyzer according to FIG. 18a, FIG. 19a shows the device according to the invention for carrying out heterogeneous immunoassays according to FIG. 18a, in a three-dimensional view.

The automatic analyzer 100 shown in FIGS. 18*a* and 18*b* is extended by a device for carrying out heterogeneous immunoassays 410 (HetIA module), which is arranged directly in the extension of the stationary cuvette array 200.

The cuvettes 201 of the HetIA module, which in order to hold liquid media (samples, reagents, suspensions containing magnetic particles, washing solutions) are arranged in a temperature-controlled cuvette block 820, form a terminal segment 210 of the stationary, linear cuvette array 200 of the analyzer 100, such that the pipettors 300*a*, 300*b* which are movable along the cuvette array 200 can also supply the cuvettes 201 of the HetIA module with samples and reagents from the sample and reagent stores 920, 950*a*, 950*b* and also with magnetic particles and washing solutions. The cuvette washing station 600 which is movable along the cuvette array 200 also has access to the cuvettes 201 of the HetIA module.

If cuvettes 201 of the HetIA module or in other regions of the cuvette array 200 have to be replaced, these can be taken from a cuvette magazine 116 (which is arranged for example at the end of the cuvette array 200) by means of a gripping mechanism (not shown), for example of the pipettor 300*b* or of the cuvette washing unit 600, wherein used cuvettes are discarded into a waste chute 117.

The automatic analyzer 100 may also be equipped with an ISE measurement station 115, in which ion-selective measurements are carried out on the samples. The samples are taken from the sample store 920 by the pipettor 300*b* and are pipetted into the filling opening 118 of the ISE measurement station 115.

Figure 19A:
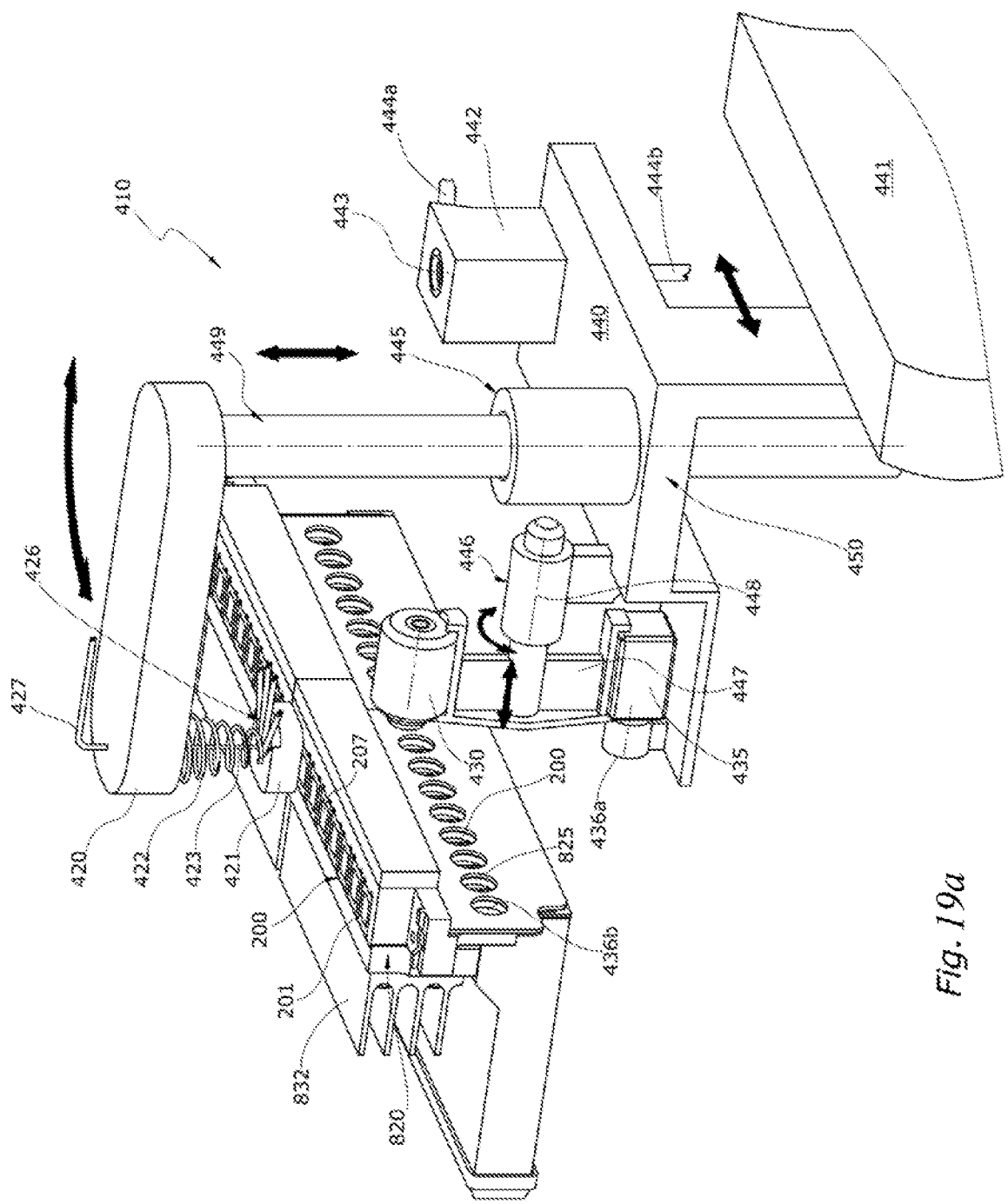
FIG. 19b shows a detail of the device according to FIG. 19a, in an enlarged sectional illustration.
Figure 19B:
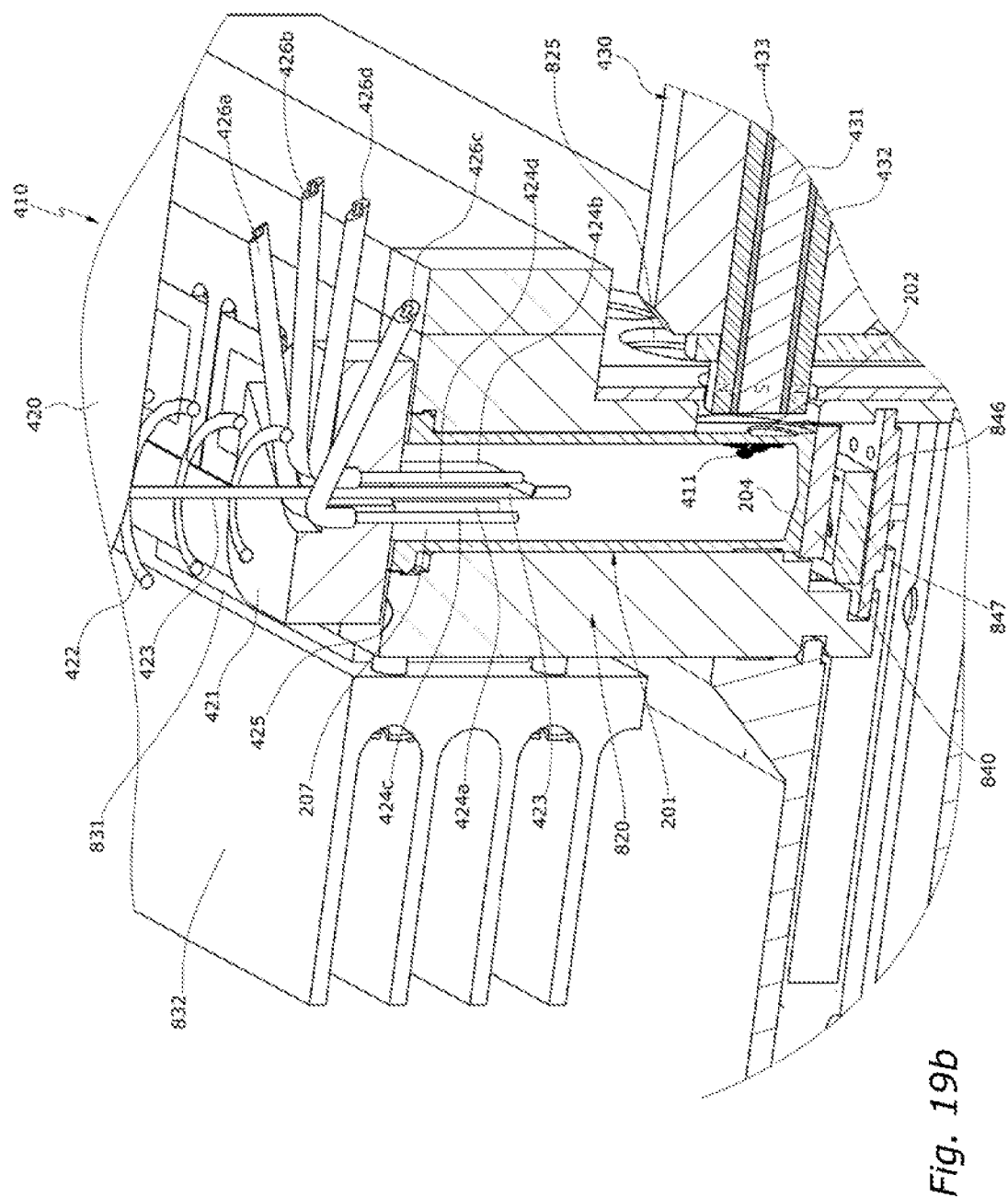

The device 410 (HetIA module) according to the invention is shown in detail in FIGS. 19*a* and 19*b*.

A pivotable support arm 420 of the device 410 is designed to be movable along the cuvette array 200 and can be lowered toward the filling opening 207 of a cuvette 201 selected by the control logic of the device. The support arm 420 is equipped with an aspirating needle 423, which can be lowered toward the bottom 204 of the cuvette 201, together with an aspirating line 427, and also with at least one dispenser 424*a* to 424*d* which can be positioned above or in the respective filling opening 207 in order to dispense the liquid media into the cuvette 201. At least one dispenser 424*a*, 424*b* is designed to dispense a washing solution for the magnetic particles 411.

The supply lines to the dispensers 424*a*, 424*b* are denoted by 426; specifically, a washing line 426*a* leads to the dispenser 424*a*, a washing line 426*b* leads to the dispenser 424*b*, a supply line 426*c* leads to the dispenser for a pretrigger solution, and a supply line 426*d* leads to the dispenser 424*d* for a trigger solution.

A magnet assembly 430 for separating the magnetic particles 411 on an inner surface of the cuvette 201 is also provided, which is movable along the cuvette array 200 and acts on the contents of the selected cuvette 201, and also an optical detection device 435 which is movable along the cuvette array 200 and which can be aligned with the measurement window 202 of the selected cuvette 201 in order to obtain a measurement signal which is proportional to the analyte concentration in the selected cuvette 201.

For the sake of simplicity, only those components of the device 410 which are essential to the present invention are shown, wherein analyzer components such as sample and reagent stores, pumps, valves, evaluation units, control units and drive units will not be discussed in detail.

The cuvette array 200 is arranged in a temperature-controllable cuvette block 820, wherein the Peltier elements 831 which are provided for controlling the temperature can be seen in particular in FIG. 19*b*, these being arranged between the cooling fins 832 and the cuvette block 820. The cuvette block 820 has, on the front side, access openings 825 which align with the measurement windows 202 of the cuvettes 201.

A dispenser platform 421, which can be lowered onto the filling opening 207 of the cuvette 201 and which in the example shown has four dispensers 424*a* to 424*d* for dispensing liquid media into the cuvette 201, is fastened to a flexible mount (see spring element 422) on the movable support arm 420. The aspirating needle 423 attached to the support arm 420 passes through the dispenser platform 421 in a central opening, so that said aspirating needle can be lowered to the bottom 204 of the cuvette 201 once the dispenser platform 421 has been placed onto the filling opening 207 of the cuvette 201.

The dispenser platform 421 has, on the side facing toward the cuvette 201, a sealing surface 425 made of a material that is impervious to light, so that, when the dispenser platform 412 is lowered, it is not possible for ambient light to enter while the cuvette contents are being optically measured.

According to the invention, one dispenser 424*a* for dispensing a washing solution for the magnetic particles 411 has an outflow direction which is oriented parallel to the longitudinal axis of the cuvette 201 (straight washing needle), and a second dispenser 424*b*—also for dispensing a washing solution—has an outflow direction which is aimed onto an inner lateral surface of the cuvette 201 (angled washing needle).

Of further dispensers 424*c*, 424*d* of the dispenser platform 412, the outflow directions of which are oriented parallel to the longitudinal axis of the cuvette 201, an optional third dispenser 424*c* is optionally designed to dispense a pretrigger solution and a fourth dispenser 424*d* is optionally designed to dispense a trigger solution. For immunoassays based on chemiluminescence, which require only a trigger solution, the third dispenser 424*c* may remain unused or may be omitted.

The exemplary embodiment shown in FIGS. 19*a* and 19*b* is characterized by a platform 440 which is movable along the cuvette array 200 and which has a lifting and rotating device 445, by which the support arm 420 together with the aspirating needle 423 and the dispensers 424*a* to 424*d* of the dispenser platform 421 can be lowered. Preferably, a common suspension mount 446 for the magnet assembly 430 and the detection device 435 is also arranged on the movable platform 440, so that a movable measurement and manipulation module 450 is realized, which combines all the robotic, fluidic and metrological components for the process steps of magnetically separating the beads, so-called B/F-washing, and also triggering and measuring the luminescence.

The movable platform 440 of the measurement and manipulation module 450 is connected to the frame of the device 410 via a lateral rail 441 which extends parallel to the cuvette array 200, and can be brought to the position of a selected cuvette 201 via a movement mechanism such as, for example, a stepper-motor-driven toothed belt, a spindle, or a linear motor. For supplying power to and controlling the measurement and manipulation module 450, flexible electrical and fluidic connection lines, for example in the form of so-called energy chains (not shown), can be led to the platform 440.

According to one embodiment variant, a washing station 442 for the aspirating needle 423 and the at least one dispenser 424*a* to 424*d* of the dispenser platform 421 may also be arranged on the movable platform 440, it being possible for the support arm 420 to be lowered onto the opening 443 of said washing station after a rotational movement, so that the entire needle group on the head of the pivotable support arm 420 can be introduced into the opening 443.

The needle washing station 442 has an upper aspirating line 444*a*, which limits the fill level, and a lower aspirating line 444*b*. In this case, a movement toward the opening 443 is possible by an up and down movement with a 90° pivot while simultaneously lowering the support arm 420 below the upper edge of the cuvette array 200, as a result of which other robotic components, for example any pipettors, etc., can move unhindered along the cuvette array 200.

The pivotable support arm 420 of the measurement and manipulation module 450 is attached to a tower 449 which is pivotable through 90° in a horizontal plane and is additionally movable in the vertical direction, wherein the pivoting movement is enabled by a rotary actuator, which is driven for example by a stepper motor. In addition, the tower is equipped with a lifting device which comprises, for example, a stepper-motor-driven spindle or a toothed belt for generating a vertical translational movement of the support arm 420. The two types of movement can be integrated in the combined lifting and rotating device 445 at the base of the vertical tower 449.

According to one embodiment variant, the needle washing station may also be positioned in a stationary manner at a position below the movable platform 440 along the horizontal movement space thereof.

One embodiment variant may also consist in that the needle washing station is positioned in a stationary manner at the end of the cuvette array 200, wherein the support arm of the needle group need not be pivotable in this variant.

According to one preferred embodiment variant, the common suspension mount 446 for the magnet assembly 430 and the detection device 435 is suitable for carrying out a translational or rotational movement in order to swap the positions of the magnet assembly 430 and the detection device 435 in front of the selected cuvette 201.

By way of example, the magnet assembly 430 and the detection device 435 may be attached to a rotor arm 447, which is mounted in the suspension mount 446, at an equal distance from a common axis of rotation 448.

In this case, the rotor arm 447 mounted in the suspension mount 446 may preferably be designed to be movable in translation in the direction of the axis of rotation 448, in order to move the magnet assembly 430 or the detection device 435 toward the access opening 825 in the cuvette block 820 and thus toward the measurement window 202 of the selected cuvette 201. The photomultiplier 435 and also the magnet assembly 430 can be aligned, with their respective optical main axis or pole axis, with the corresponding access opening 825 in the cuvette block and can dock onto the respective opening by a horizontal movement in a manner sealed against the ingress of light, or can be optimally moved toward the wall of the cuvette 201 in order to generate a magnetic flux density that is as high as possible.

The magnet assembly 430 may consist of one or more magnets, which are preferably rare-earth magnets of high field strength, such as for example $Nd_2Fe_{14}B$ (neodymium iron borate), but may also be configured as electromagnets. The magnet assembly 430 is preferably formed of neodymium rod magnets with two different rod radii, wherein an inner rod 431 is substantially enclosed by an outer, hollow-cylindrical rod 432, with the interposition of a non-magnetic intermediate layer 433, and the two rods of different length and diameter have a conical transition. The assembly ends in a slim end region with a point-type high magnetic flux density, which end region can be brought close to the window 202 of the cuvette 201 through the opening 825 in the cuvette block 820. The magnet assembly 430 may also be composed of a plurality of individual magnets in order to increase the magnetic field strength that is necessary for magnetic separation on a cuvette wall, or to reduce stray fields in the neighboring cuvettes. One example of a magnet assembly is shown in FIG. 19*b*, wherein a bipolar end of a concentric magnet assembly 430 having a non-magnetic intermediate layer 433 is directed toward the cuvette 201.

According to one embodiment variant, a second magnet assembly (not shown) which is movable along the cuvette array 200 and which acts on the contents of the selected cuvette 201 may be provided, said magnet assembly preferably forming a magnetic N-S bridge with at least one of the magnetic poles of the first magnet assembly 430. The movable platform 440 of the measurement and manipulation module 450 may have for example a C-shaped boom arm which is passed through below the stationary cuvette array 200 and which makes it possible to orient a second separation magnet along the magnetic axis of action of the first separation magnet, and enables said second separation magnet to travel along on the other side of the cuvette block 820. In this case, a second opening which is comparable to the first access opening 825 of the respective cuvette 201 is not required, since the magnetic field lines of the second magnet assembly act through the material of the cuvette block (aluminum), which is not made of ferromagnetic material. Ideally, the polarity of the two separation magnets is oriented oppositely, so that a magnetic series circuit (N-S) is formed, which leads to a point-type increase in the magnetic flux density and to a reduction in the unwanted stray field on the adjacent cuvettes. The stray field adversely affects the magnetic beads located in neighboring cuvettes, since the beads in the neighboring cuvettes may be in different process stages, during which a magnetic separation or agglomeration is undesirable.

The second magnet assembly may consist both of one or more electromagnets and also of permanent magnets, wherein, in the case of permanent magnets, an actuator must be provided in order to move the magnetic assembly selectively toward or away from the cuvette. The actuator mechanism may be configured in a manner analogous to that for the first magnet assembly 430 and may have, in a known manner, a belt drive, a drive spindle or a solenoid.

In another conceivable configuration, it is provided that the second magnet assembly can independently be moved past the components of the measurement and manipulation module 450, on a separate rail from the first magnet assembly 430, so that, in addition to the abovementioned advantages of a second separation magnet which also travels along, at the same time a magnetic separation on another cuvette is possible in order to pre-separate magnetic beads for a washing step of a second assay in the other cuvette and thus to save time.

The detection device 435 is preferably realized by a compact photomultiplier and serves to measure the quantity of light during the chemiluminescence triggered by adding the two trigger solutions, and may be equipped with a Peltier cooling device in order to obtain a more constant, lower-noise signal. To avoid extraneous light during the measurement at one of the access openings 825 of the cuvette block 820, the access openings 825 and the light inlet opening of the photomultiplier may have concentrically stepped contact surfaces at the edge of the two openings. In addition, a shutter, which is actuated for example mechanically, may be provided in order to protect the photomultiplier in the rest state against the ingress of ambient light.

To measure the luminescence in the case of a low analyte concentration, use is preferably made of a digital photomultiplier which, for each incoming photon, triggers and releases a digital pulse of 10 ns. These short pulses are counted by the FPGA of the HetIA controller 460 and are summed as a count over a settable sampling time. As long as the number of photons is small, the irregularly generated pulses can be output individually; the number of pulses per unit of time then corresponds to the number of photons per unit of time.

According to the invention, a reference light source 436a for the detection device 435 may be arranged on the movable platform 440. The reference light source 436a serves to calibrate the photomultiplier and has a light outlet opening which is oriented in the direction of the inlet opening of the detection device 435 (for example photomultiplier). The reference light source 436a may be arranged at any point along the line of movement of the detection device 435, but ideally such that a calibration of the photomultiplier takes place when the magnet assembly 430 is located exactly in front of the respective access opening 825 of the cuvette block 820.

As an alternative to this variant, a reference light source 436b may also be arranged in a stationary manner at the end of the cuvette block 820 and may have a light outlet opening along the access openings of the cuvette block 820, as a result of which the temperature control device of the latter is also used for the reference light source 436b.

Figure 20:
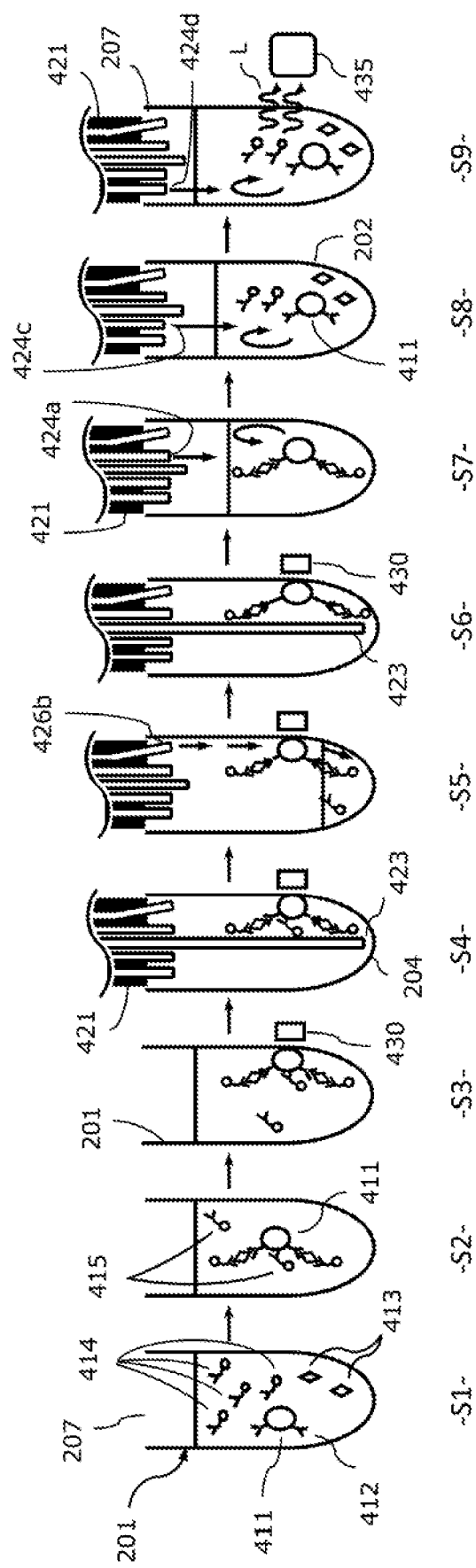
FIG. 20 shows a schematic process example of a heterogeneous immunoassay.

The process example of a heterogeneous immunoassay is shown by way of example in steps S1 to S9 in FIG. 20.

The present example of a heterogeneous immunoassay relates to the necessary machine processes during a so-called "sandwich assay". In this case, the analyte molecule 413 (an endogenous protein, for example prostate-specific antigen) forms, by antigen/antibody interactions, a bridge between a first antibody (capture antibody 412), which is immobilized on the surface of the magnetic particles 411, and a second antibody to which signal molecules are bound (tracer antibody 414), which, after adding a pretrigger liquid and a trigger liquid, gives rise to a chemiluminescence which is proportional to the quantity of analyte and which lasts a few seconds. The two types of antibody are in excess compared to the analyte. In the case of analyte molecules which are too small to have binding sites for two different antibodies, so-called competitive immunoassays are used, wherein the tracer antibodies compete directly with the analyte molecules for binding sites on an immobilized antibody.

In a simple 1-step assay as shown in FIG. 20, the sample (which contains the analyte 413), a suspension of magnetic particles 411 (magnetic beads) with a coating of a capture antibody 412, and a solution of the tracer antibody 414 are first pipetted into the cuvette 201 by means of a pipettor (not shown here) (S1, in FIG. 20).

During the subsequent incubation (approximately 10 min) at 37° C., the solution is periodically stirred, for example by means of ultrasound, in order to prevent the beads from sinking and agglomerating. Each analyte molecule is then bound in a "sandwich-like" manner between a capture antibody 412, which is immobilized on the beads 411, and a tracer antibody 414. There are also non-specifically bound tracer antibodies 415 (S2, in FIG. 20).

The beads 411 together with the substances bound thereto are then fixed to the inner wall of the cuvette 201 by means of the magnet assembly 430 (S3, in FIG. 20), and the entire liquid is removed by the aspirating needle 423 lowered from the dispenser platform 421 (S4, in FIG. 20).

Thereafter, a washing solution is introduced through a washing needle 424b which is directed at an angle onto the inner wall of the cuvette 201, in order to remove non-bound tracer antibodies which adhere to the beads 430 and remain in the reaction solution, by carefully rinsing the beads, the beads 411 still being magnetically held on the vessel wall (S5, in FIG. 20).

The cuvette 201 is then sucked dry again, wherein the beads 411 together with the substances bound thereto are still magnetically fixed to the inner wall of the cuvettes 201 (S6, in FIG. 20).

A second, vertically oriented washing needle 424a, when injecting washing solution or dilution liquid, in contrast generates turbulence in the liquid, so that the beads 411 are resuspended in the liquid when the magnets are undocked (S7, in FIG. 20).

After this washing step, which may be carried out multiple times in succession, the photomultiplier 435 is moved toward the cuvette 201. Pretrigger solution (S8, in FIG. 20)

and trigger solution (S9, in FIG. 20) are then supplied in rapid, immediate succession by the two dispensers 424c and 424d. A chemiluminescence L (flash luminescence) is thus triggered, which lasts only a few seconds and which can be measured by the photomultiplier 435. The dispenser platform 421 of the support arm, which is placed onto the filling opening 207 of the cuvette 201 for this purpose, at the same time ensures the necessary darkening of the cuvette 201.

The used cuvette 201 is then sucked empty by the aspirating needle 423 and either is replaced by a disposable cuvette or is cleaned and reused, so that a new immunoassay can take place in the previously used cuvette position.

In order to wash the cuvette, the manipulator must be moved away from the cuvette so that the cuvette washing station can approach the latter and start to wash it.

In principle, however, it is also possible for other, somewhat modified immunoassays, which have a magnetic separation with B/F washing as a process step, to be carried out using the device according to the invention, wherein a different detection method than measuring the chemiluminescence may optionally also be provided for the detection.

Figure 21:
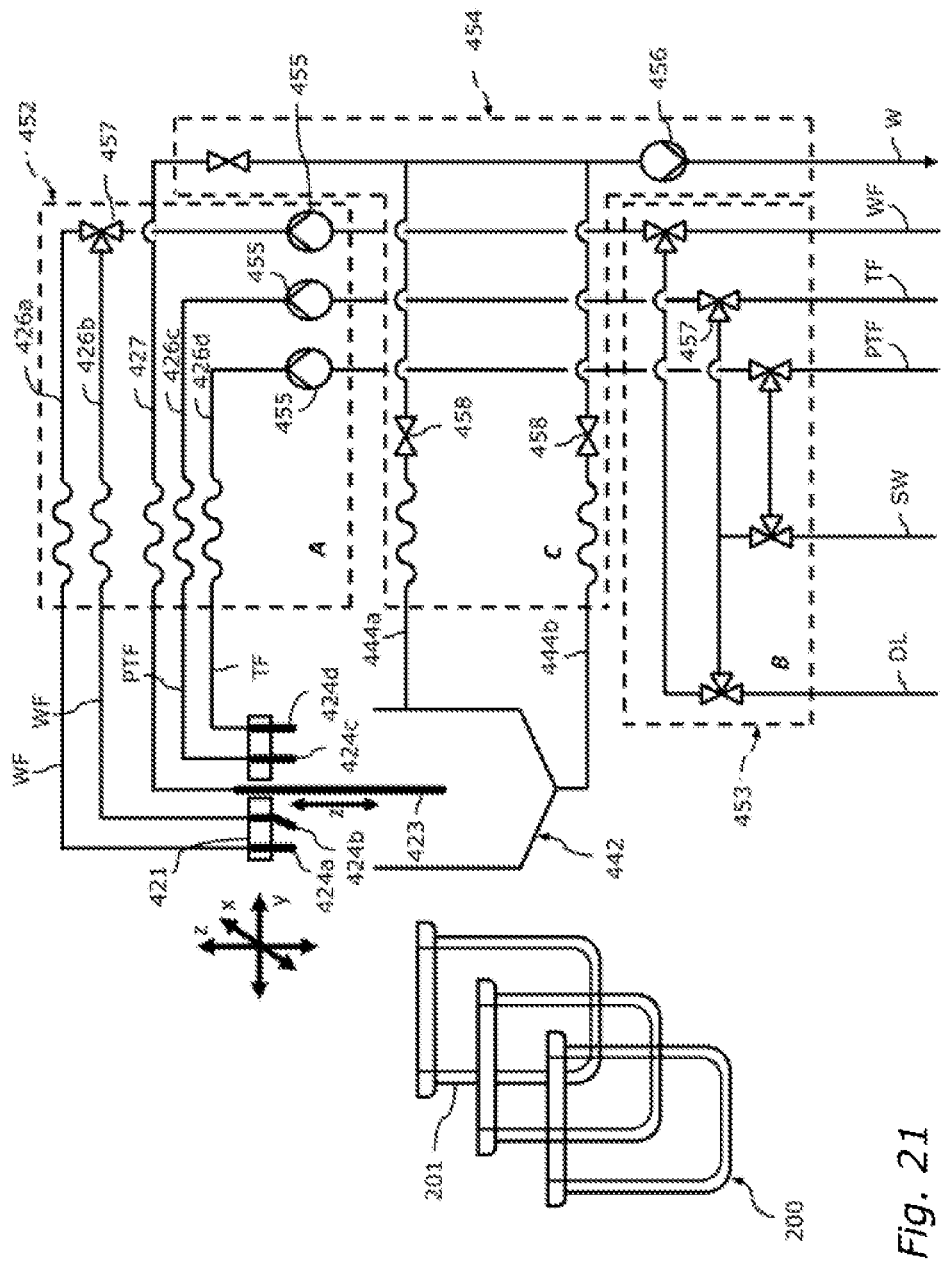

As shown schematically in FIG. 21, the movable measurement and manipulation module 450 of the invention shown in FIG. 18a has a fluidic system 451 for supplying the dispenser platform 421 with washing liquid WF, pretrigger liquid PTF, trigger liquid TF and compressed air DL. Devices for aspirating reaction mixture or washing liquid from the cuvettes 201 of the cuvette array 200 and also the container, or washing trough, of the washing station 442 are also provided.

The fluidic system 451 is controlled via the HetIA controller 460 (see FIG. 22) and comprises a series of magnetically operable 3-way valves 457 and precision piston pumps as dispensing pumps 455, which are connected to the movable platform 440 (see FIG. 19a) via flexible hose connections (indicated by wavy lines).

The dispenser platform 421, which is movable in the x-, y- and z-direction via the combined degrees of freedom of the movable platform 440 and of the pivotable support arm 420, comprises a group of dispensers 424a to 424d supplemented by the lowerable aspirating needle 423.

The dispensing unit 452 has a separate dispensing pump 455 in each case for supplying washing liquid WF, pretrigger liquid PTF and trigger liquid TF, wherein the flow of liquid from the dispensing pump 455 for the washing liquid can be switched to the straight washing needle 424a or to the angled washing needle 424b via a 3-way valve 457. The four selectively chargeable supply lines are made of a flexible plastic at the movable points and are guided in energy chains (not shown).

The dispensing pumps 455 of the dispensing unit 452 are each connected to the valve network 453 via separate supply lines, wherein, for rinsing and cleaning purposes, in particular for cleaning the dispensers 424a to 424d and the aspirating needle 423, in place of the primary conveying medium it is alternatively also possible to switch to compressed air DL or system water SW (deionized water) via a corresponding 3-way valve 427, and to supply this to the dispensing pumps 455.

The container of the washing station 442 for cleaning the dispensers 424a to 424d and the aspirating needle 423 has two aspirating lines 444a, 444b, of which one 444b is located in the bottom of the container and a second is located in the upper half of the container in order to be able to act as an overflow for setting a stable fill level. The aspirating unit 454 is connected both to the two aspirating lines 444a, 444b and to the aspirating needle 423 via flexible hose lines, which are guided in energy chains (not shown). In order to prevent unwanted backflow of aspirated liquids, shut-off valves 458 are provided in each case. The three discharge lines open into a common feed line to a suction pump 456 (for example a self-priming positive displacement pump), which supplies the aspirated waste liquids W to a collection or treatment area in the device (not shown)

Figure 22:
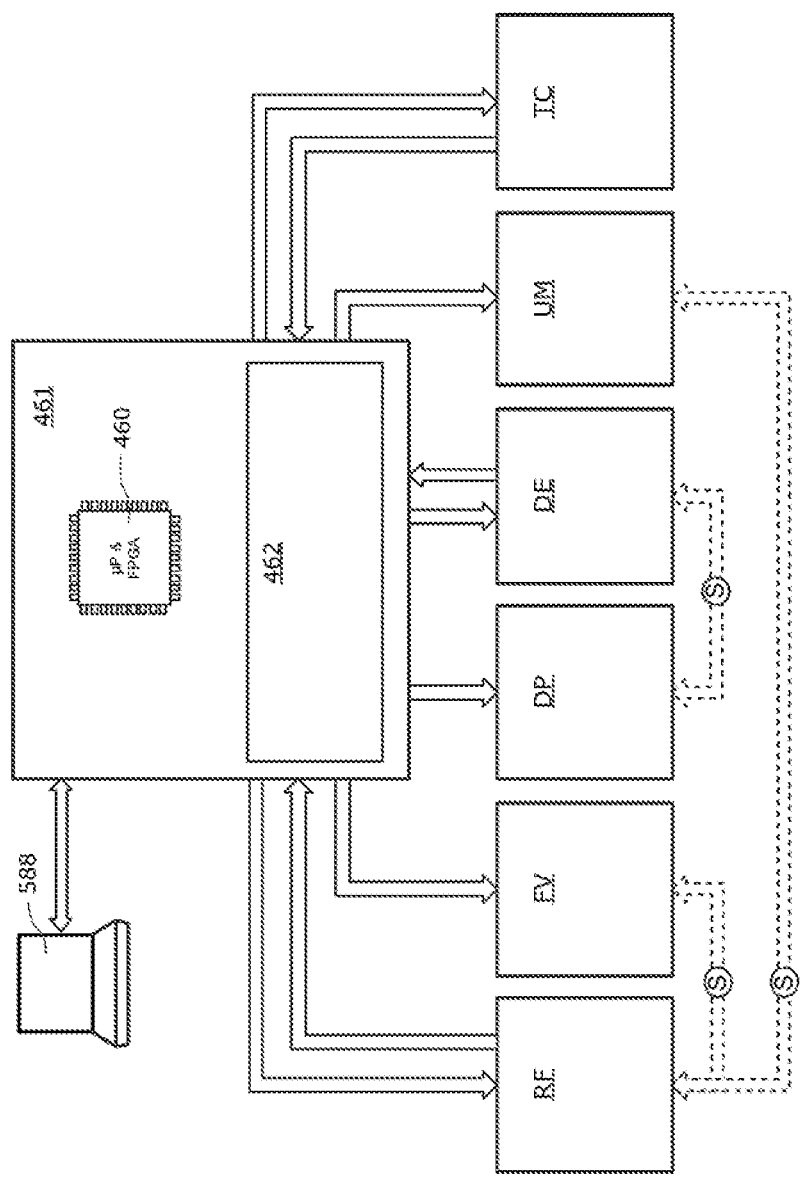

FIG. 22 shows a block diagram regarding the electronic control of the device according to the invention as shown in FIG. 19a. The HetIA controller 460 of the controller board 461 operates the electrical and mechanical components of the HetIA module and is controlled and programmed by a main computer 588 (for example personal computer). The PC controls the flow and order of the sub-processes, and the HetIA controller 460 is responsible for executing the individual actions.

The functions of the HetIA controller 460 can be summarized as follows (see FIG. 22):
communication with PC 588 via Ethernet interface
robotics functions RF by means of stepper motors
  moving the platform 440 in the x-direction to the respective cuvette 201 of the stationary cuvette array 200 (and to the stationary reference light source 436b in the cuvette block 820 if no moving reference light source 436a is provided)
  rotating the rotor arm 447 in order to swap the position of the detection device 435 (photomultiplier) and magnet assembly 430
  y-movement for docking the photomultiplier 435 or the magnet assembly 430 onto the measurement window of the cuvette 201, and onto a reference light source 436a moving with the platform 440
controller FV of the fluidic valves 457, 458 of the fluidic system 451
controller DP for the metering pumps 455
controller UM for the ultrasonic transducer 840
  has a separate ultrasonic oscillator which is independent of the controller board 461
  decoder function for the piezoelectric transducers 840 on the individual cuvettes 201
controller DE for the detection device 435 and also the reference light source 436a
temperature control TR for the temperature control device (37° C.)
  Peltier controller for the detection device 435 (photomultiplier)
  Peltier controller for the cuvette block 820
Certain functions which have to be triggered exactly in real time (see parentheses "S" in FIG. 22) are realized in the FPGA of the HetIA controller 460. These are, for example:
  temporal triggering of the controller DP of the metering pump in time with the controller DE for the detection device 435 (photomultiplier measurement)
  triggering of the reference light source synchronously with the measurement of the photomultiplier
  ultrasonic mixing process of the respective cuvette.

What is claimed is:
1. An automatic analyzer for carrying out chemical, biochemical and/or immunochemical analyses of liquid samples, which are present in a sample store of the analyzer, with the aid of liquid reagents, which are present in at least one reagent store of the analyzer, the automatic analyzer comprising
  cuvettes for receiving the liquid samples and reagents, wherein a plurality of cuvettes is arranged as a stationary, linear cuvette array in the analyzer, a first pipettor configured and arranged to be movable in an x-direction along the linear cuvette array, said pipettor being equipped with at least one pipetting needle which is designed to be lowerable in a z-direction into the cuvettes and which is designed to be movable in a y-direction, substantially normal to the x-direction, between the cuvettes, the sample store and the reagent store, a device with an optical measurement unit for performing photometric and/or turbidimetric measurements which, in order to obtain a measurement signal, is equipped with a light supply unit configured to irradiate light through measuring windows arranged laterally on the cuvettes, and with a detection unit in order to obtain the measurement signal, which is configured to receive measurement radiation emerging through measurement windows arranged laterally on the cuvettes, a device configured and arranged for carrying out heterogeneous immunoassays, comprising an optical detection device which can be moved along the stationary, linear cuvette array and is suitable for receiving measurement radiation emerging through measurement windows arranged laterally on the cuvettes;

a cuvette washing unit configured and arranged to be movable in the x-direction, for cleaning the cuvettes, a needle washing unit configured and arranged to clean the at least one pipetting needle, and a temperature control unit configured and arranged to set a measurement temperature in the cuvettes;

wherein the device for performing photometric and/or turbidimetric measurements has access to the cuvettes of a first region of the stationary linear cuvette array and the device for performing heterogeneous immunoassays has access to the cuvettes of a second region of the stationary linear cuvette array; and wherein the first pipettor, and the cuvette washing unit, are configured and arranged to be movable independently of one another along the first and the second region of the linear cuvette array and each have access to different cuvettes of the first and the second region in a freely selectable order.

2. The analyzer according to claim 1, wherein the analyzer includes a second pipettor, and the first and second pipettors are configured and arranged to be movable in the x-direction independently of one another.

3. The analyzer according to claim 1 wherein at least one of the first and second pipettors comprises two pipetting needles which are movable in the y-direction independently of one another and parallel to one another.

4. The analyzer according to claim 1, wherein the needle washing unit is arranged on the first pipettor and is configured and arranged to be movable therewith.

5. The analyzer according to claim 1, wherein the optical measurement unit includes a unit which is movable along the first region of the linear, stationary cuvette array, the unit having a light-supplying unit and a spectrometer.

6. The analyzer according to claim 1, wherein the optical measurement unit includes
a light-supplying unit with a plurality of LED light sources configured and arranged to emit in a spectrally different manner in a UV/VIS/NIR wavelength range, and
a stationary detection unit with at least one photodiode fixedly assigned to each cuvette of the first region of the cuvette array.

7. The analyzer according claim 1, wherein the temperature control unit includes heating foils which thermally contact individual cuvettes or groups of cuvettes and configured and arranged to receive different temperature levels.

8. The analyzer according to claim 1, wherein the temperature control unit includes a cuvette block configured and arranged to be regulated to a predefined target temperature, said cuvette block including a temperature control device and positioned in thermal contact with the individual cuvettes.

9. The analyzer according to claim 1, wherein the analyzer includes a mixer unit and wherein the mixer unit is assigned to the cuvettes in order to mix the samples and reagents, wherein the mixer unit is at least one ultrasonic transducer and is attached to each cuvette of the first region, the ultrasonic transducer configured and arranged to introduce ultrasonic energy into the cuvettes, and wherein the ultrasonic transducer is a piezoelectric vibrator and is connected to a control unit configured and arranged to actuate the ultrasonic transducer as a function of parameter values of the liquid media.

10. The analyzer according to claim 9, wherein the mixer unit and the temperature control unit are configured as a combined mixing and temperature control device.

11. The analyzer according to claim 1, wherein the device configured and arranged-for carrying out heterogeneous immunoassays includes the following:
at least one support arm configured and arranged to be movable along the second region of the cuvette array and lowerable toward the filling opening of a selected cuvette, said support arm having at least one aspirating needle configured and arranged to be lowerable toward the bottom of the cuvette, and also having at least one dispenser configured and arranged to be positioned above or in a respective filling opening, for dispensing the liquid media into the cuvette, wherein at least one dispenser is configured and arranged to dispense a washing solution for magnetic particles,
at least one magnet assembly configured and arranged to separate the magnetic particles on an inner surface of the cuvette, said magnet assembly configured and arranged to be movable along the second region of the cuvette array and to act on the contents of the selected cuvette, and
the optical detection device configured and arranged for receiving a measurement signal that is proportional to an analyte concentration in the selected cuvette, said optical detection device being alignable with the measurement window of the selected cuvette of the second region.

12. The analyzer according to claim 11, wherein the at least one dispenser is arranged in a dispenser platform which is configured and arranged to be lowered onto or into a filling opening of the cuvette, the lowerable aspirating needle configured and arranged to pass through said dispenser platform.

13. The analyzer according to claim 11, wherein the support arm arranged on a movable platform forms, along with the dispenser platform together with the magnet assembly and the detection device, a measurement and manipulation module which is configured and arranged to be movable along the cuvette array and which combines all the robotic, fluidic and metrological components for the process steps of a heterogeneous immunoassay.

14. A method for determining an antigen by means of a heterogeneous immunoassay, using an automatic analyzer according claim 1, wherein, in a first step sequence A, a sample for determining the antigen, a suspension of magnetic particles containing a capture antibody, and optionally a tracer antibody or a labeled antigen are pipetted into a selected cuvette of the second region of the stationary cuvette array, and in that the following steps B of an immunochemical analysis, such as a) separating the magnetic particles, b) introducing and aspirating a washing solution one or more times, c) adding a metered quantity of at least one trigger liquid, and d) carrying out a luminometric measurement of the sample, take place with the aid of a measurement and manipulation module which is movable along the second region of the cuvette array and which is stopped at the selected cuvette in order to carry out some or all of steps a) to d).

15. A method for automatic chemical, biochemical and/or immunochemical analysis of liquid samples, in order to determine at least one analyte concentration in the sample, using an automatic analyzer according to claim 1, comprising the following steps:

transferring a predetermined quantity of a liquid sample from a sample vessel in the sample store into a cuvette of the first region of the stationary, linear cuvette array by means of a first pipettor which is movable along the cuvette array;

transferring a predetermined quantity of a reagent liquid from a reagent vessel of the reagent store into the cuvette of the first region of the stationary, linear cuvette array by means of the first pipettor or by means of a second pipettor which is movable independently of the first;

mixing and controlling the temperature of the liquids in the cuvette;

optically measuring the contents of the cuvette by means of the optical measurement unit, and determining at least one measured value;

calculating and displaying the analyte concentration based on the measured values and on previously known or predetermined reference values and calibration values;

washing and drying the cuvette by means of a cuvette washing unit which is movable along the cuvette array; and providing the cuvette for subsequent analysis.

16. The method according to claim 15, wherein the following steps are carried out in mutual succession in order to mix and control the temperature of the contents of the cuvette:

a) heating the cuvette to a predefined target temperature with the aid of a temperature-controllable cuvette block, b) heating the liquid media with the aid of the temperature-controlled cuvette block in order to reach the predefined target temperature, c) in the heating phase according to point b), before the target temperature is reached, additionally introducing a predetermined quantity of ultrasonic energy with the aid of at least one ultrasonic transducer, which is attached to each cuvette, in order to increase the rate of heating, and d) simultaneously mixing the liquid media with the aid of the ultrasonic energy introduced in point c).

17. The method according to claim 15, wherein in order to assist the mixing process, at least a portion of the liquid volume introduced into the cuvette is aspirated and dispensed back into the cuvette at least once.

18. The method according to claim 14, wherein while steps for the immunochemical analysis are being carried out in the selected cuvette, the magnet assembly and the detection device arranged in a measurement and manipulation module are moved to at least one further cuvette of the cuvette array in order to carry out some or all of the steps B of an immunochemical analysis.

* * * * *